US006645168B2

(12) United States Patent
Demopulos et al.

(10) Patent No.: US 6,645,168 B2
(45) Date of Patent: *Nov. 11, 2003

(54) ARTHROSCOPIC IRRIGATION SOLUTION AND METHOD FOR INHIBITION OF PAIN AND INFLAMMATION

(75) Inventors: Gregory A. Demopulos, Mercer Island, WA (US); Pamela A. Pierce, Tiburon, CA (US); Jeffrey M. Herz, Mill Creek, WA (US)

(73) Assignee: Omeros Corporation, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/195,625

(22) Filed: Jul. 12, 2002

(65) Prior Publication Data
US 2003/0114355 A1 Jun. 19, 2003

Related U.S. Application Data

(63) Continuation of application No. 09/837,141, filed on Apr. 17, 2001, now Pat. No. 6,420,432, which is a continuation of application No. 09/072,913, filed on May 4, 1998, now Pat. No. 6,261,279, which is a continuation of application No. 08/670,699, filed on Jun. 26, 1996, now Pat. No. 5,820,583, which is a continuation-in-part of application No. PCT/US95/16028, filed on Dec. 12, 1995, which is a continuation-in-part of application No. 08/353,775, filed on Dec. 12, 1994, now abandoned.

(51) Int. Cl.[7] .................. A61M 31/00; A61K 31/135
(52) U.S. Cl. ................... 604/49; 604/500; 514/654
(58) Field of Search .................. 604/49, 500; 514/654

(56) References Cited

U.S. PATENT DOCUMENTS

| 4,490,379 | A | 12/1984 | Podos et al. |
|---|---|---|---|
| 4,504,493 | A | 3/1985 | Marshall et al. |
| 4,525,359 | A | 6/1985 | Greenway, III et al. |
| 4,640,912 | A | 2/1987 | Hausman |
| 4,659,714 | A | 4/1987 | Watt-Smith |
| 4,872,865 | A | 10/1989 | Bloebaum et al. |
| 4,880,791 | A | 11/1989 | Weithmann et al. |
| 4,938,970 | A | 7/1990 | Hustead et al. |
| 4,971,955 | A | 11/1990 | Soll et al. |
| 5,051,443 | A | 9/1991 | Neufeld et al. |
| 5,180,812 | A | 1/1993 | Dower et al. |
| 5,272,139 | A | 12/1993 | Cary |
| 5,288,725 | A | 2/1994 | Witherup et al. |
| 5,304,724 | A | 4/1994 | Newton |
| 5,350,761 | A | 9/1994 | Van Duzer et al. |
| 5,360,820 | A | 11/1994 | Hagan et al. |
| 5,411,743 | A | 5/1995 | Moore et al. |
| 5,446,070 | A | 8/1995 | Mantelle |
| 5,468,505 | A | 11/1995 | Hubbell et al. |
| 5,480,901 | A | 1/1996 | Baker et al. |
| 5,502,080 | A | 3/1996 | Hitzig |
| 5,502,082 | A | 3/1996 | Unger et al. |
| 5,512,055 | A | 4/1996 | Domb et al. |
| 5,523,316 | A | 6/1996 | Gan et al. |
| 5,536,241 | A | 7/1996 | Zapol |
| 5,605,690 | A | 2/1997 | Jacobs et al. |
| 5,610,184 | A | 3/1997 | Shahinian, Jr. |
| 5,616,688 | A | 4/1997 | Cerami et al. |
| 5,618,563 | A | 4/1997 | Berde et al. |
| 5,658,955 | A | 8/1997 | Hitzig |
| 5,667,764 | A | 9/1997 | Kopia et al. |
| 5,744,482 | A | 4/1998 | Cohen et al. |
| 5,767,105 | A | 6/1998 | Peyman |

(List continued on next page.)

FOREIGN PATENT DOCUMENTS

| EP | 0126315 A1 | 11/1984 |
|---|---|---|
| EP | 0351755 | 1/1990 |
| EP | 0364266 A2 | 4/1990 |
| EP | 0715855 A2 | 6/1996 |
| EP | WO 96/26738 | 9/1996 |
| EP | WO 96/29074 | 9/1996 |
| EP | 0710479 | 1/1999 |
| WO | WO 91/04058 | 4/1991 |
| WO | WO 92/04008 | 3/1992 |
| WO | WO 95/16435 | 6/1995 |
| WO | WO 95/27482 | 10/1995 |
| WO | WO 96/34599 | 11/1996 |
| WO | WO 97/24459 | 7/1997 |

OTHER PUBLICATIONS

Thulesius, O., et al., "Ketanserin in intermittent claudication: effect on walking distance, blood pressure, and cardiovascular complications," *J. Cardiovasc. Pharmacol.* 9:728–733 (1987).

Hedner, T., et al., "Effects of a new serotonin antagonist, ketanserin, in experimental and clinical hypertension," *Am. J. Hypertens.* 1:317S–323S (1988).

(List continued on next page.)

*Primary Examiner*—William R. A. Jarvis
(74) *Attorney, Agent, or Firm*—Christensen O'Connor Johnson Kindness PLLC

(57) ABSTRACT

A method and solution for perioperatively inhibiting a variety of pain and inflammation processes at wounds from general surgical procedures including oral/dental procedures. The solution preferably includes multiple pain and inflammation inhibitory at dilute concentration in a physiologic carrier, such as saline or lactated Ringer's solution. The solution is applied by continuous irrigation of a wound during a surgical procedure for preemptive inhibition of pain and while avoiding undesirable side effects associated with oral, intramuscular, subcutaneous or intravenous application of larger doses of the agents. One preferred solution to inhibit pain and inflammation includes a serotonin$_2$ antagonist, a serotonin$_3$ antagonist, a histamine antagonist, a serotonin agonist, a cyclooxygenase inhibitor, a neurokinin$_1$ antagonist, a neurokinin$_2$ antagonist, a purinoceptor antagonist, an ATP-sensitive potassium channel opener, a calcium channel antagonist, a bradykinin$_1$ antagonist, a bradykinin$_2$ antagonist and a $\mu$-opioid agonist.

36 Claims, 12 Drawing Sheets

U.S. PATENT DOCUMENTS

Figure 1:
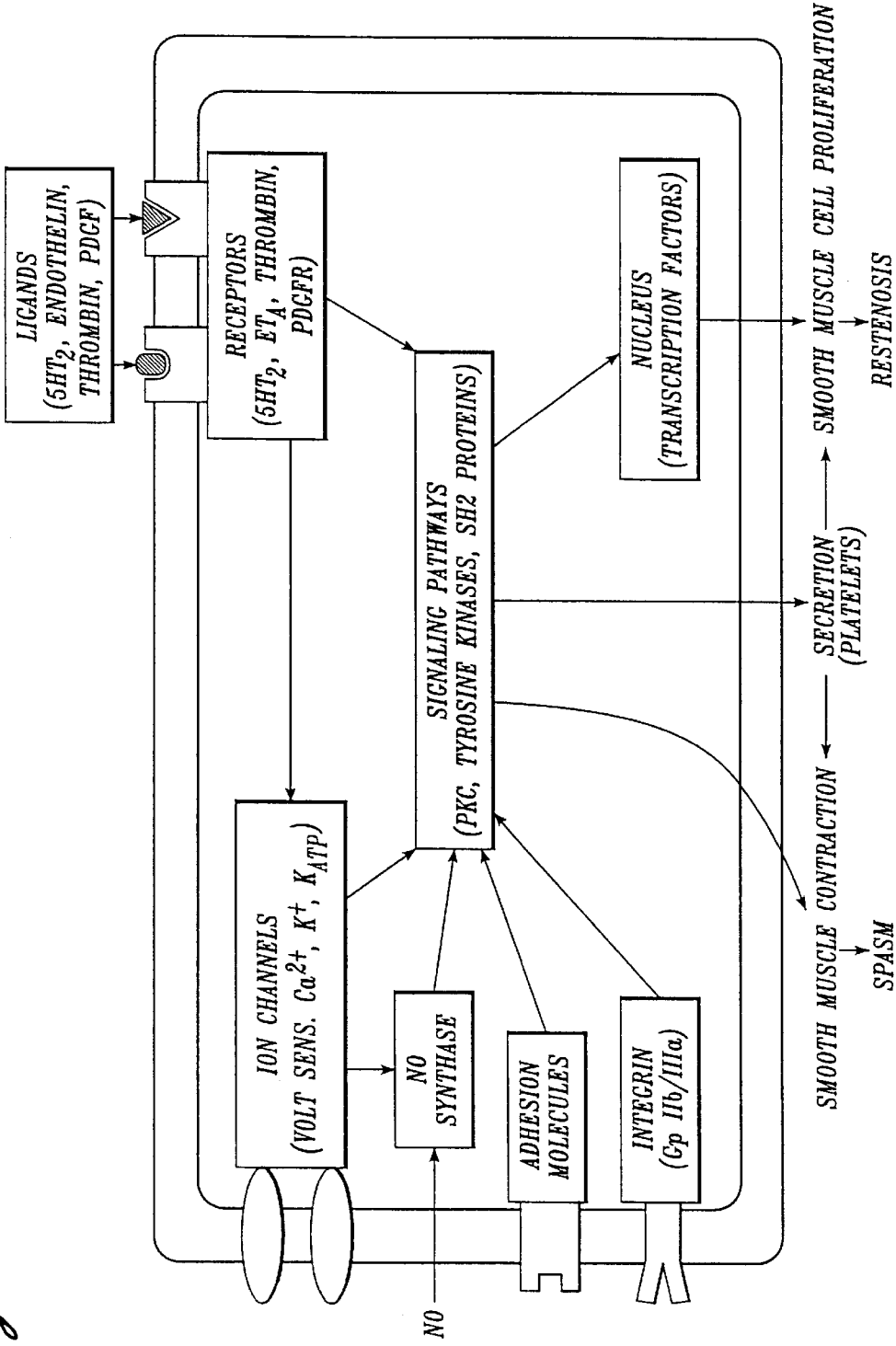

| | | | |
|---|---|---|---|
| 5,800,385 | A | 9/1998 | Demopulos et al. |
| 5,820,583 | A | 10/1998 | Demopulos et al. |
| 5,858,017 | A | 1/1999 | Demopulos et al. |
| 5,860,950 | A | 1/1999 | Demopulos et al. |
| 5,942,241 | A | 8/1999 | Chasin et al. |
| 5,942,530 | A | 8/1999 | Panetta et al. |
| 5,994,372 | A | 11/1999 | Yaksh |
| 6,056,715 | A | 5/2000 | Demopulos et al. |
| 6,210,394 | B1 | 4/2001 | Demopulos et al. |
| 6,242,447 | B1 | 6/2001 | Demopulos et al. |
| 6,254,585 | B1 | 7/2001 | Demopulos et al. |
| 6,261,279 | B1 | 7/2001 | Demopulos et al. |
| 6,306,820 | B1 | 10/2001 | Bendele et al. |

OTHER PUBLICATIONS

Hof, R.P., et al., "Antiarrhythmic and hemodynamic effects of tropisetron in anesthetized rabbits," *J. Cardiovasc. Pharmacol.* 22:499–505 (1993).

Naesh, O., et al., "Platelet activation in mental stress," *Clin. Physiol.* 13:299–307 (1993).

Evans, R.G., et al., "Effects of 5–HT–receptor and alpha 2–androceptor ligands on the haemodynamic response to acute central hypovolemia in conscious rabbits," *Br. J. Pharmacol.* 109:37–47 (1993).

Van Hemelrijck, J., et al., "Blood pressure management during aortic surgery: urapidil compared to isosorbide dinitrate," *J. Cardiothorac. Vasc. Anesth.* 7:273–278 (1993).

Evans, R.G., et al., "A CNS serotonergic mechanism in acute central hypovolemia in conscious rabbits?" *J. Cardiovasc. Pharmacol.* 19:1009–1017 (1992).

Vyssoulis, G.P., et al., "Left ventricular hypertrophy regression and function changes with ketanserin in elderly hypertensives," *Cardiovasc. Drugs Ther.* 4:81–84 (1990).

Sigal, S.L., et al., "Effects of Serotonin–Receptor Blockade on Angioplasty–Induced Vasospasm in an Atherosclerotic Rabbit Model," *Arterioscler. Thrombosis* 11:770–783 (1991).

Kalsner, S., et al., "Coronary arteries of cardiac patients are hyperreative and contain stores of amines: a mechanism for coronary spasm," *Science* 223:1435–1437 (1984).

Willerson, J.T., et al., "Specific Platelet mediators and unstable coronary artery lesions," *Circulaton* 80:198–205 (1989).

Saxena, P.R., et al., "Cardiovascular effects on serotonin agonists and antagonists," *J. Cardiovasc. Pharmacol.* 15:S17–S34 (1990).

Ashton, J.H., et al., "Serotonin as a mediator of cyclic flow variations in stenosed canine coronary arteries," *Circulation* 73:572–578 (1986).

Douglas, W.W. "Histamine and 5–hydroxytryptamine (serotonin) and their antagonists," In: *The Pharmacological Basis of Therapeutics* 605–638 (1985).

Kessler, W., et al., "Excitation of cutaneous afferent nerve endings in vitro by a combination of inflammatory mediators and conditioning effect of substance P," *Exp. Brain Res.* 91:467–476 (1992).

Lang, E., et al., "Chemosensitivity of fine afferents from rat skin in vitro," *J. Neurophysiol.* 63:887–901 (1990).

Levine, J.D., et al., "Desipramine enhances opiate postoperative analgesia," *Pain* 27:45–49 (1986).

Richardson, B.P., et al., "Identification of serotonin M–receptor subtypes and their specific blockade by a new class of drugs," *Nature* 316:126–131 (1985).

Ringkamp, M., et al., "Activated human platelets in plasma excite nociceptors in rat skin, in vitro," *Neurosci. Lett.* 170:103–106 (1994).

Buzzi, M.G., et al., "The antimigraine drug, sumatriptan (GR43175), selectively blocks neurogenic plasma extravasation from blood vessels in dura mater," *Br. J. Pharmacol.* 99:202–206 (1990).

Buzzi, M.G., et al., "5–Hydroxytryptamine receptor agonists for the abortive treatment of vascular headaches block mast cell, endothelial and platelet activation within the rat dura mater after trigeminal stimulation," *Brain Res.* 583:137–149 (1992).

Zochodne, D.W., et al., "Sumatriptan blocks neurogenic inflammation in the peripheral nerve trunk," *Neurology* 44:161–163 (1994).

Schwartz, M.M., et al., "Vascular leakage in the kidney and lower urinary tract: effects of histamine, serotonin and bradykinin," *Proc. Soc. Exp. Biol. Med.* 140:535–539 (1972).

Holliman, C.J., et al., "The effect of ketanserin, a specific serotonin antagonist, on burn shock hemodynamic parameters in a porcine burn model," *J. Trauma* 23:867–871 (1983).

Serruys, P.W., et al., "Evaluation of ketanserin in the prevention of restenosis after percutaneous transluminal coronary angioplasty; a multicenter randomized double–blind placebo–controlled trial," *Circulation* 88:1588–1601 (1993).

Cohen, B.M., et al., "Intracoronary cocktail infusion during rotational ablation: safety and efficacy," *Transcatheter Cardiovascular Therapeutics* (1995).

Berkenboom, G., et al., "Atherosclerosis and responses of human isolated coronary arteries to endothelium–dependent and –independent vasodilators," *J. Cardiovasc. Pharmacol.* 14:S35–S39 (1989).

Kaumann, A.J., et al., "Variable participation of 2HT1–like receptors and 5–HT1 receptors in serotonin–induced contraction of human isolated coronary arteries," *Circulation* 90:1141–1153 (1994).

Quast, U., et al., "Cellular Pharmacology of Potassium Channel Openers in Vascular Smooth Muscle," *Cardiovascular Research* 28:805–810 (1994).

Golino, P., et al., "Failure of nitroglycerine and diltiazem to reduce platelet–mediated vasoconstriction in dogs with coronary artery stenosis and endothelial injury: further evidence for thromboxane $A_2$ and serotonin as mediators of coronary artery vasoconstriction in vivo," *J. Am. Coll. Cardiol.* 15:718–726 (1990).

DeCaterina, R., et al., "A Double–blind, Placebo–controlled Study of Ketanserin in Patients with Prinzmetal's Angina," *Circulation* 69:889–894 (1984).

Golino, P., et al., "Divergent Effects of Serotonin on Coronary–Artery Dimensions and Blood Flow in Patients with Coronary Artherosclerosis and Control Patients," *New Engl. J. Med.* 324:641–648 (1991).

Golino, P., et al., "Local Effect of Serotonin Released During Coronary Angioplasty," *New Engl. J. Med.* 330:523–528 (1994).

Ashton, J.H., et al., "Serotonin $S_2$ and Thromboxane $A_2$–Prostaglandid $H_2$ Receptor Blockade Provide Protection Against Epinephrine–Induced Cyclic Flow Variations in Severly Narrowed Canine Coronary Arteries," *J. Am. Coll. Cardiol.* 13:755–763 (1989).

Yao, S., et al., "Combined ADP and Thromboxane $A_2$ Antagonism Prevents Cyclic Flow Variations is Stenosed and Endothelium–Injured Arteries in Nonhuman Primates," *Circulation* 88:2888–2893 (1993).

Cohen, B.M., et al., "Cocktail attenuation of rotational ablation flow effects (CARAFE) study: pilot," *Cathet. Cardiovasc. Diagn.* Suppl. 3:69–72 (1996).

Reuben, S. S., et al., "Postoperative analgesia for outpatient arthroscopic knee sugery with intraarticular bupivacaine and kerorolac," *Anesth. Analg.* 80:1154–1157 (1995).

Sosnowski, M., et al., "Spinal Administration of Receptor–Seletive Drugs as Analgesics: New Horizons," *J. Pain Symptom Manag.* 5:204–213 (1990).

Gyrn, J., et al., "Intra–articular Bupivacaine Plus Adrenaline for Arthroscopic Surgery of the Knee," *Acta Anaesthsiol. Scand.* 36:643–646 (1992).

Thomas, et al., "The Direct Perfusion of Surgical Wounds with Local Anaesthetic Solution: An Approach to Postoperative Pain?," *Annal R Coll Surg* 65:226–229 (1983).

Kuga, T., et al., "Inhibitory Effects of Aspirin on Coronary Hyperreactivity to Autacoids After Arterial Balloon Injury in Minature Pigs," *J. Cardiovasc. Pharmacol.* 25:273–281 (1995).

Reifart, et al., "Randomized Comparison of Angioplasty of Complex Coronary Lesions at a Single Cetner," *Circulation* 96:91–98 (1997).

Willerson, J.T., et al., "Pretreatment with Antagonists to Thromboxane A2, Serotonin and ADP Reduces Neointimal Proliferation in Canine Coronary Arteries after Endothelial Injury," *J. Am. Coll. Cardiol.* Incomplete Data:906–32(1994).

Knorr, A.M. "Why is Nisoldipine a Specific Agent in Ischemic Left Ventricular Dysfunction?"*Am. J. Cardiol.* 75:36E–40E (1995).

Pierce, P.A., et al., "Dual Effect of the Serotonin Agonist, Sumatriptan, on Peripheral Neurogenic Inflammation," *Reg. Anesth.* 21:219–225 (1996).

Herrman et al., "Pharmacological Approaches to the Prevention of Restenosis Following Angioplasty," *Drugs* 46:18–52 (1993).

Vahanian et al., "Role of Calcium Channel Blockers in Reducing Acute Ischemia and Preventing Restenosis in PCTA," *Drugs* 52:9–15 (1996).

Narayanan et al., "Recombinant Hirudin: Initial Observations in Reconstructive Microsurgery," *Haemostasis* 21:168–171 (1991).

el–Sanadiki, M.N., et al., "Reduction of Intimal Hyperplasia and Enhanced Reactivity of Experimental Vein Bypass Grafts with Verapamil Treatment," *Ann. Surg.* 212:87–96 (1990).

Blackham et al., "FPL 62064 a Topically Active 5–Lipoxygenase/Cycloxygenase Inhibitor," *Agents and Actions* 30:432–442(1991).

Hirayama et al., "NK, Receptors Mediate Tachykinin–Induced Plasma Extravasation in the Rat Knee," *Agents Actions* 40:171–175 (1994).

Khoury, G., et al., "Intraarticular morphine, bupivacaine, and morphine/bupivacaine for pain control after knee videoarthroscopy," *Anesthesiology* 77:263–266 (1992).

Allen, G., et al., "Postarthroscopy analgesia with intraarticular bupivacaine/morphine. A randomized clinical trial," *Anesthesiology* 79:475–480 (1993).

Uysalel, A., et al., "Comparison of intraarticular bupivacaine with the addition of morphine or fentanyl for analgesia after arthroscopic surgery," *Arthroscopy* 11:660–663 (1995).

Ruwe, P., et al., "The effect of intraarticular injection of morphine and bupivacaine on postarthroscopic pain control," *Am. J. Sports Med.* 23:59–64 (1995).

Jaureguito, J., et al., "A comparison of intraarticular morphine and bupivacaine for pain control after outpatient knee arthroscopy. A prospective, randomized, double–blinded study," *Am. J. Sports Med.* 23:350–353 (1995).

Reuben, S. S., et al., "Postarthroscopic meniscus repair analgesia with intraarticular ketorolac or morphine," *Anesth. Analg.* 82:1036–1039 (1996).

Reuben, S. S., et al., "Intraarticular morphine in the multimodal analgesic management of postoperative pain after ambulatory anterior cruciate ligament repair," *Anesth. Analg.* 86:374–378 (1998).

Bisla, K., et al., "Concentration–dependent effects of lidocaine on corneal epithelial wound healing," *Invest Ophthalmol. Vis. Sci.* 33: 3029–3033 (1992).

Massey, T., et al., "Serum lidocaine levels during arthroscopy using continuous irrigation with lidocaine," *Clin. Orthop.* 229:182–184 (1988).

Tsai, L., et al., "Arthroscopic surgery of the knee in local anaesthesia. An analysis of age–related pathology," *Arch. Orthop. Trauma Surg.* 112:136–138 (1993).

Klein, J.A., "Tumescent Liposuction and Improved Postoperative Care Using Tumescent Liposuction Garments," *Dermatologic Clinics* 13:329–338 (1995).

Klein, J.A., "Tumescent Technique for Local Anesthesia Improves Safety in Large–Volume Liposuction," *Plastic and Reconstr Surg* 92:1085–1100 (1993).

Klein, J.A., "The Tumescent Technique Anesthesia and Modified Liposuction Technique," *Dermatologic Clinics* 8:425–437 (1990).

Ostad et al., "Tumescent Anesthesia with a Lidocaine Dose of 55 mg/kg is Safe for Liposuction" *Dermatol Surg* 22:921–927 (1996).

Klein, J.A., "Anesthesia for Liposuction in Dermatologic Surgery," *J. Dermatol Surg and Oncol* 14:1124–1132 (1988).

Debruyne, D., et al., "Prilocaine in arthroscopy: clinical pharmacokinetics and rational use," *Clin. Pharmacol Ther.* 38: 549–553 (1985).

Wredmark, et al., "Arthroscopy Under Local Anaesthesia Using Controlled Pressure–Irrigation With Prilocaine," *J Bone Joint Surg* 64:583–585 (1982).

Talke, P., et al., "Effects of perioperative dexmedetomidine infusion in patients undergoing vascualr surgery. The Study of Perioperative Ischemia Research Group," *Anesthesiology* 82:620–633 (1995).

Ben–David et al., "Is Preoperative Ketorolac A Useful Adjunct To Regional Anesthesia For Inguinal Herniorrhaphy?," *Acta Anaesthesiol Scana* 40:358–363 (1996).

Hyrkäs et al., "Effective Postoperative Pain Prevention Through Administration Of Bupivacaine And Diclofenac," *Anesth Prog* 41:6–10 (1994).

Glasser et al., "The Perioperative Use Of Corticosteroids And Bupivacaine In The Management Of Lumbar Disc Disease," *J Neurosurg* 78: 383–387 (1993).

Dionne et al., "Suppression Of Postoperative Pain By The Combination Of A Nonsteroidal Anti–Inflammatory Drug, Flurbiprofen, And A Long–Acting Local Anesthetic, Etidocaine," *JADA* 108:598–601 (1984).

Sindelar, et al., "Randomised Trial Of Intraperitoneal Irrigation With Low Molecular Weight Providone–Iodine Solution To Reduce Intra–Abdominal Infectious Complications," *J Hosp Infect* 6:103–114 (1985).

Goldring, et al., "Etodolac Preserves Cartilage–Specific Phenotype in Human Chondrocytes: Effects On Type II Collagen Synthesis and Associated mRNA Levels," *Euro J Rheum & Inflamm* 10:10–21 (1990).

Jacobi, et al., "Inhibition of Peritoneal Tumor Cell Growth and Implantation in Laparoscopic Surgery in a Rat Model," *Am J Surg* 174:359–363 (1997).

Karczag, et al., "Mouse Peritoneal Cells Activated With a Combiniation of Indomethacin, Poly I: C and Syncumar Inhibit the Take of Lewis Lung Carcinoma, in Adoptive Transfer Assay," *Acta Microbiologia Hung* 34:207–214 (1987).

Capdevila, X., et al., "Effects of perioperative analgesic technique on the surgical outcome and duration of rehabilitation after major knee surgery," *Anesthesiology* 91:8–15 (1999).

McSwiney, M. M., et al., "Analgesia following arthroscopic knee surgery. A controlled study of intra–articular morphine, bupivacaine or both combined," *Anaesth. Intensive Care* 21:201–203 (1993).

Gatt, C.J., Jr., et al., "Preemptive analgesia: its role and efficacy in anterior cruciate ligament reconstruction," *Am. J. Sports Med.* 26:524–529 (1998).

Fig. 1 VASCULAR CELL MOLECULAR TARGETS & SIGNALING INFORMATION

Figure 2:
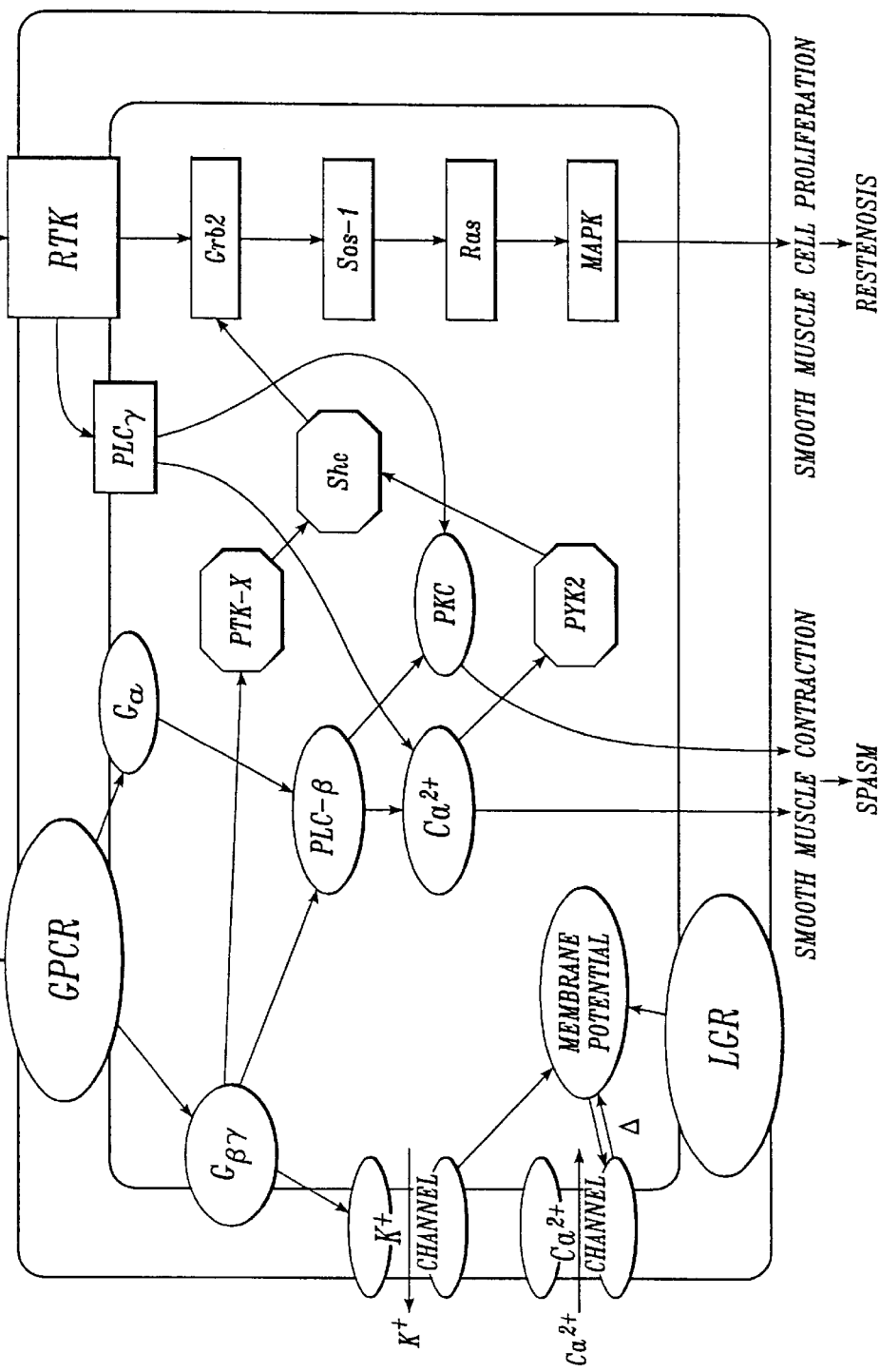

Fig. 2 DETAILED SIGNALING PATHWAYS IN A VASCULAR SMOOTH MUSCLE CELL

Figure 3:
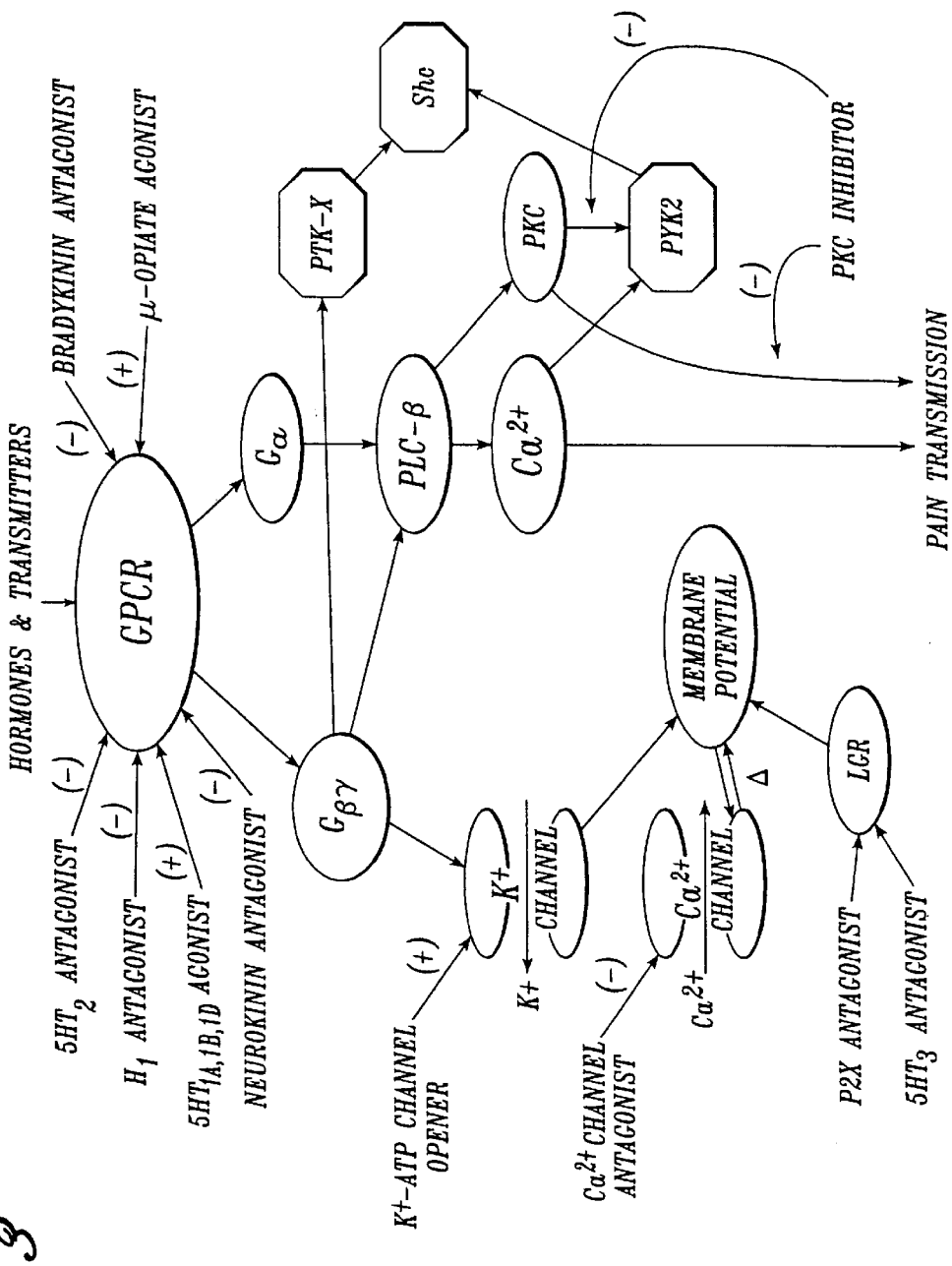

Fig. 3  MOLECULAR SITES OF DRUG ACTION IN PREFERRED ARTHROSCOPIC SOLUTION

Figure 4:
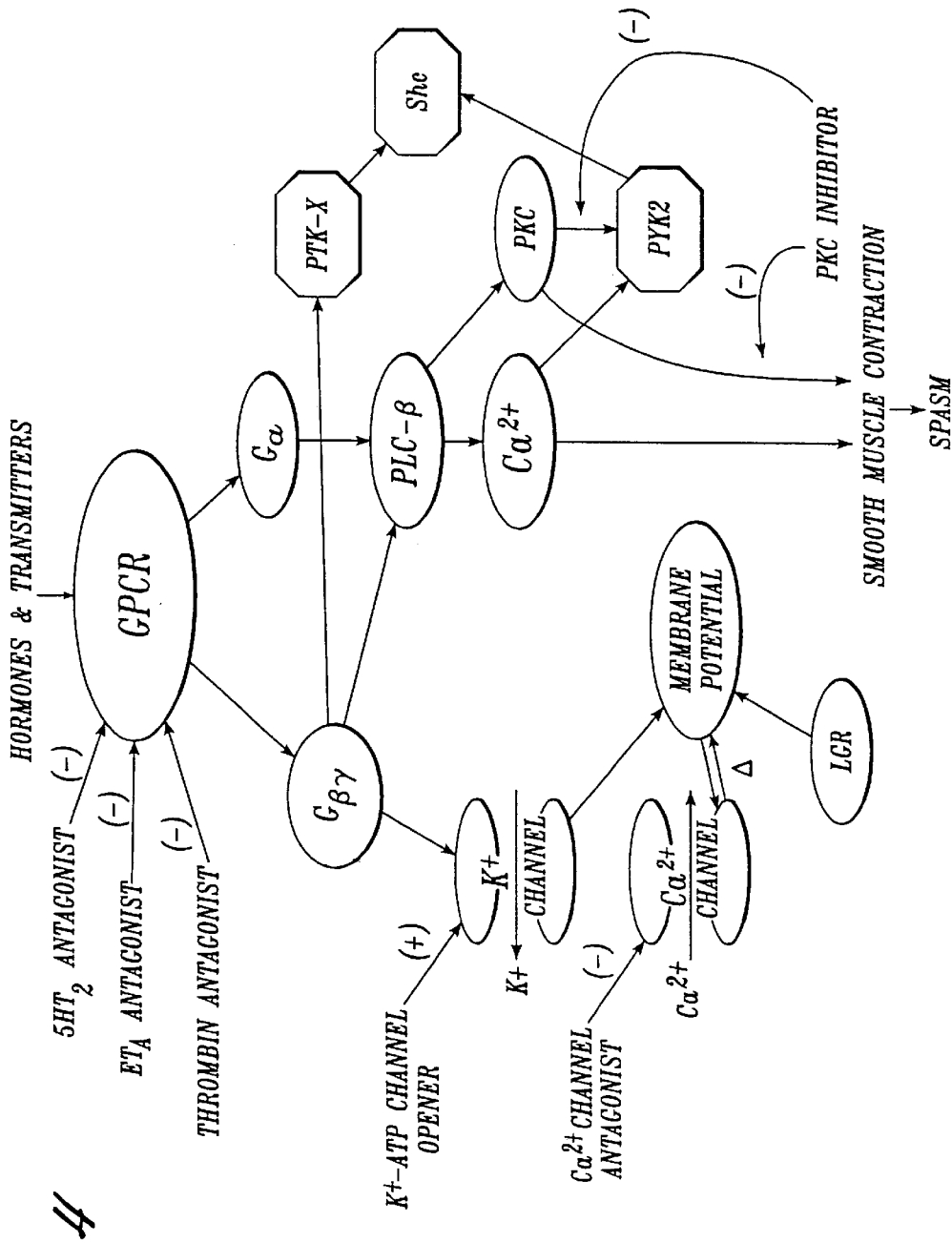

Fig. 4 MOLECULAR SITES OF DRUG ACTION IN PREFERRED CARDIOVASCULAR & GENERAL VASCULAR SOLUTION – I/II

MOLECULAR SITES OF DRUG ACTION IN PREFERRED CARDIOVASCULAR & GENERAL VASCULAR SOLUTION – II/II

Figure 7:
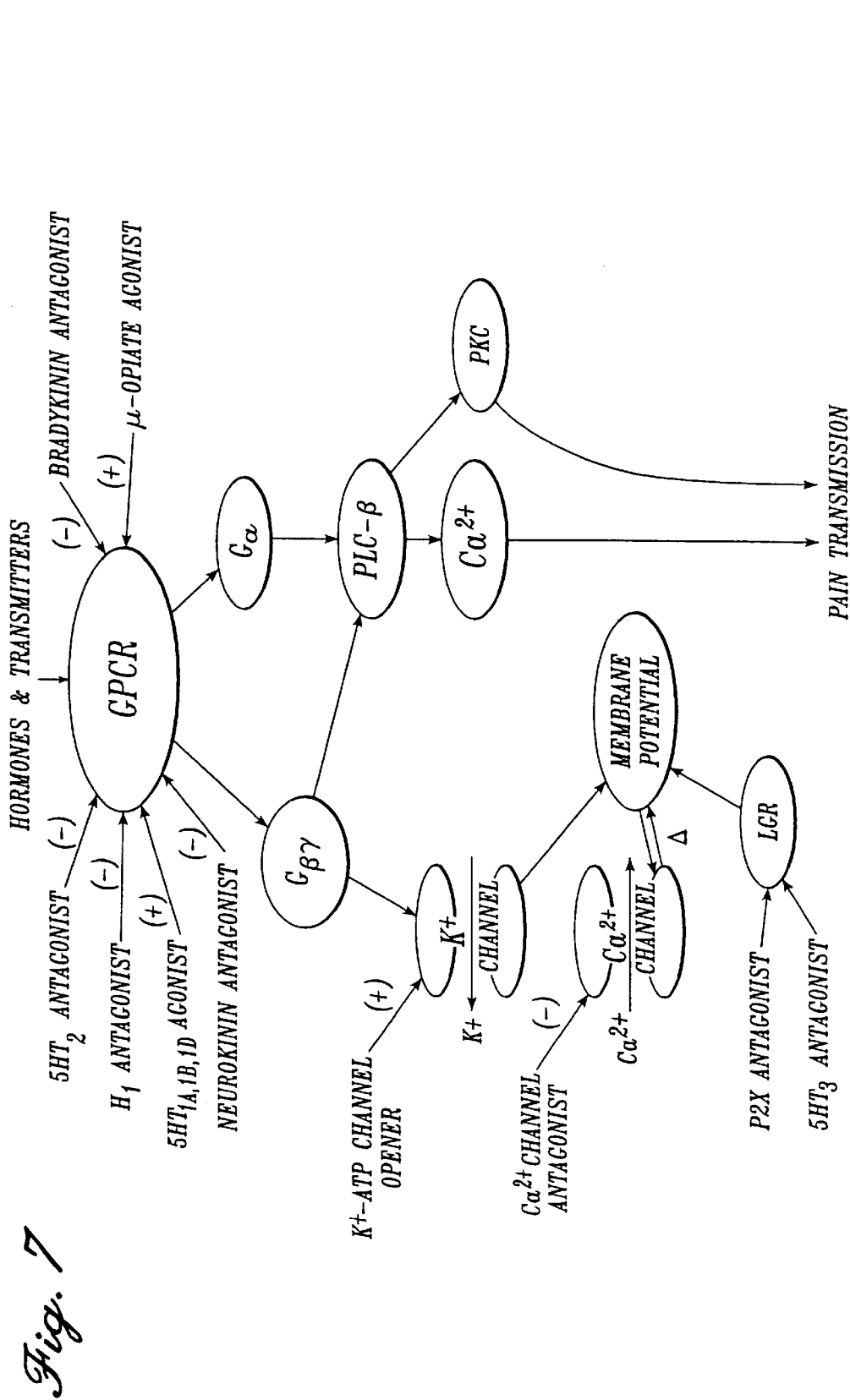

Fig. 7  MOLECULAR SITES OF DRUG ACTION IN PREFERRED GENERAL SURGICAL WOUND SOLUTION

ARTHROSCOPIC IRRIGATION SOLUTION AND METHOD FOR INHIBITION OF PAIN AND INFLAMMATION

CROSS REFERENCE TO RELATED APPLICATIONS

The present application is a continuation of U.S. patent application Ser. No. 09/837,141, filed Apr. 17, 2001, to issue as U.S. Pat. No. 6,420,432, which is a continuation of U.S. patent application Ser. No. 09/072,913, filed May 4, 1998, now U.S. Pat. No. 6,261,279, which is a continuation of U.S. patent application Ser. No. 08/670,699, filed Jun. 26, 1996, now U.S. Pat. No. 5,820,583, which is a continuation-in-part of International Patent Application No. PCT/US95/16028, filed Dec. 12, 1995, designating the United States and which is a continuation-in-part of co-pending U.S. patent application Ser. No. 08/353,775, filed Dec. 12, 1994, now abandoned, priority of the filing dates of which is hereby claimed under 35 U.S.C. §120.

I. FIELD OF THE INVENTION

The present invention relates to surgical irrigation solutions and methods, and particularly for anti-inflammatory, anti-pain, anti-spasm and anti-restenosis surgical irrigation solutions.

II. BACKGROUND OF THE INVENTION

Arthroscopy is a surgical procedure in which a camera, attached to a remote light source and video monitor, is inserted into an anatomic joint (e.g., knee, shoulder, etc.) through a small portal incision in the overlying skin and joint capsule. Through similar portal incisions, surgical instruments may be placed in the joint, their use guided by arthroscopic visualization. As arthroscopists' skills have improved, an increasing number of operative procedures, once performed by "open" surgical technique, now can be accomplished arthroscopically. Such procedures include, for example, partial meniscectomies and ligament reconstructions in the knee, shoulder acromioplasties and rotator cuff debridements and elbow synovectomies. As a result of widening surgical indications and the development of small diameter arthroscopes, wrist and ankle arthroscopies also have become routine.

Throughout each arthroscopy, physiologic irrigation fluid (e.g., normal saline or lactated Ringer's) is flushed continuously through the joint, distending the joint capsule and removing operative debris, thereby providing clearer intraarticular visualization. U.S. Pat. No. 4,504,493 to Marshall discloses an isomolar solution of glycerol in water for a non-conductive and optically clear irrigation solution for arthroscopy.

Irrigation is also used in other procedures, such as cardiovascular and general vascular diagnostic and therapeutic procedures, urologic procedures and the treatment of burns and any operative wounds. In each case, a physiologic fluid is used to irrigate a wound or body cavity or passage. Conventional physiologic irrigation fluids do not provide analgesic, anti-inflammatory, anti-spasm and anti-restenotic effects.

Alleviating pain and suffering in postoperative patients is an area of special focus in clinical medicine, especially with the growing number of out-patient operations performed each year. The most widely used agents, cyclooxygenase inhibitors (e.g., ibuprofen) and opioids (e.g., morphine, fentanyl), have significant side effects including gastrointestinal irritation/bleeding and respiratory depression. The high incidence of nausea and vomiting related to opioids is especially problematic in the postoperative period. Therapeutic agents aimed at treating postoperative pain while avoiding detrimental side effects are not easily developed because the molecular targets for these agents are distributed widely throughout the body and mediate diverse physiological actions. Despite the significant clinical need to inhibit pain and inflammation, as well as vasospasm, smooth muscle spasm and restenosis, methods for the delivery of inhibitors of pain, inflammation, spasm and restenosis at effective dosages while minimizing adverse systemic side effects have not been developed. As an example, conventional (i.e., intravenous, oral, subcutaneous or intramuscular) methods of administration of opiates in therapeutic doses frequently is associated with significant adverse side effects, including severe respiratory depression, changes in mood, mental clouding, profound nausea and vomiting.

Prior studies have demonstrated the ability of endogenous agents, such as serotonin (5-hydroxytryptamine, sometimes referred to herein as "5-HT"), bradykinin and histamine, to produce pain and inflammation. Sicuteri, F., et al., *Serotonin-Bradykinin Potentiation in the Pain Receptors in Man*, Life Sci. 4, pp. 309–316 (1965); Rosenthal, S. R., *Histamine as the Chemical Mediator for Cutaneous Pain*, J. Invest. Dermat. 69, pp. 98–105 (1977); Richardson, B. P., et al., *Identification of Serotonin M-Receptor Subtypes and their Specific Blockade by a New Class of Drugs*, Nature 316, pp. 126–131 (1985); Whalley, E. T., et al., *The Effect of Kinin Agonists and Antagonists*, Naunyn-Schmiedeb Arch. Pharmacol. 36, pp. 652–57 (1987); Lang, E., et al., *Chemo-Sensitivity of Fine Afferents from Rat Skin In Vitro*, J. Neurophysiol. 63, pp. 887–901 (1990).

For example, 5-HT applied to a human blister base (denuded skin) has been demonstrated to cause pain that can be inhibited by $5-HT_3$ receptor antagonists. Richardson et al., (1985). Similarly, peripherally-applied bradykinin produces pain which can be blocked by bradykinin receptor antagonists. Sicuteri et al., 1965; Whalley et al., 1987; Dray, A., et al., *Bradykinin and Inflammatory Pain*, Trends Neurosci. 16, pp. 99–104 (1993). Peripherally-applied histamine produces vasodilation, itching and pain which can be inhibited by histamine receptor antagonists. Rosenthal, 1977; Douglas, W. W., "Histamine and 5-Hydroxytryptamine (Serotonin) and their Antagonists", in Goodman, L. S., et al., ed., *The Pharmacological Basis of Therapeutics*, MacMillan Publishing Company, New York, pp. 605–638 (1985); Rumore, M. M., et al., *Analgesic Effects of Antihistaminics*, Life Sci 36, pp. 403–416 (1985). Combinations of these three agonists (5-HT, bradykinin and histamine) applied together have been demonstrated to display a synergistic pain-causing effect, producing a long-lasting and intense pain signal. Sicuteri et al., 1965; Richardson et al., 1985; Kessler, W., et al., *Excitation of Cutaneous Afferent Nerve Endings In Vitro by a Combination of Inflammatory Mediators and Conditioning Effect of Substance P*, Exp. Brain Res. 91, pp. 467–476 (1992).

In the body, 5-HT is located in platelets and in central neurons, histamine is found in mast cells, and bradykinin is produced from a larger precursor molecule during tissue trauma, pH changes and temperature changes. Because 5-HT can be released in large amounts from platelets at sites of tissue injury, producing plasma levels 20-fold greater than resting levels (Ashton, J. H., et al., *Serotonin as a Mediator of Cyclic Flow Variations in Stenosed Canine Coronary Arteries*, Circulation 73, pp. 572–578 (1986)), it is possible that endogenous 5-HT plays a role in producing postoperative pain, hyperalgesia and inflammation. In fact, activated platelets have been shown to excite peripheral nociceptors in vitro. Ringkamp, M., et al., *Activated Human Platelets in Plasma Excite Nociceptors in Rat Skin, In Vitro*, Neurosci. Lett. 170, pp. 103–106 (1994). Similarly, histamine and bradykinin also are released into tissues during trauma. Kimura, E., et al., *Changes in Bradykinin Level in Coronary Sinus Blood After the Experimental Occlusion of a Coronary Artery*, Am Heart J. 85, pp. 635–647 (1973); Douglas, 1985; Dray et al. (1993).

In addition, prostaglandins also are known to cause pain and inflammation. Cyclooxygenase inhibitors, e.g., ibuprofen, are commonly used in non-surgical and postoperative settings to block the production of prostaglandins, thereby reducing prostaglandin-mediated pain and inflammation. Flower, R. J., et al., *Analgesic-Antipyretics and Anti-Inflammatory Agents; Drugs Employed in the Treatment of Gout*, in Goodman, L. S., et al., ed., The Pharmacological Basis of Therapeutics, MacMillan Publishing Company, New York, pp. 674–715 (1985). Cyclooxygenase inhibitors are associated with some adverse systemic side effects when applied conventionally. For example, indomethacin or ketorolac have well recognized gastrointestinal and renal adverse side effects.

As discussed, 5-HT, histamine, bradykinin and prostaglandins cause pain and inflammation. The various receptors through which these agents mediate their effects on peripheral tissues have been known and/or debated for the past two decades. Most studies have, been performed in rats or other animal models. However, there are differences in pharmacology and receptor sequences between human and animal species. There have been no studies conclusively demonstrating the importance of 5-HT, bradykinin or histamine in producing postoperative pain in humans.

Furthermore, antagonists of these mediators currently are not used for postoperative pain treatment. A class of drugs, termed 5-HT and norepinephrine uptake antagonists, which includes amitriptyline, has been used orally with moderate success for chronic pain conditions. However, the mechanisms of chronic versus acute pain states are thought to be considerably different. In fact, two studies in the acute pain setting using amitriptyline perioperatively have shown no pain-relieving effect of amitriptyline. Levine, J. D., et al., *Desipramine Enhances Opiate Postoperative Analgesia*, Pain 27, pp. 45–49 (1986); Kerrick, J. M., et al., *Low-Dose Amitriptyline as an Adjunct to Opioids for Postoperative Orthopedic Pain: a Placebo-Controlled Trial Period*, Pain 52, pp. 325–30 (1993). In both studies the drug was given orally. The second study noted that oral amitriptyline actually produced a lower overall sense of well-being in postoperative patients, which may be due to the drug's affinity for multiple amine receptors in the brain.

Amitriptyline, in addition to blocking the uptake of 5-HT and norepinephrine, is a potent 5-HT receptor antagonist. Therefore, the lack of efficacy in reducing postoperative pain in the previously-mentioned studies would appear to conflict with the proposal of a role for endogenous 5-HT in acute pain. There are a number of reasons for the lack of acute pain relief found with amitriptyline in these two studies. (1) The first study (Levine et al., 1986) used amitriptyline preoperatively for one week up until the night prior to surgery, whereas the second study (Kerrick et al., 1993) only used amitriptyline postoperatively. Therefore, no amitriptyline was present in the operative site tissues during the actual tissue injury phase, the time at which 5-HT is purported to be released. (2) Amitriptyline is known to be extensively metabolized by the liver. With oral administration, the concentration of amitriptyline in the operative site tissues may not have been sufficiently high for a long enough time period to inhibit the activity of postoperatively released 5-HT in the second study. (3) Since multiple inflammatory mediators exist, and studies have demonstrated synergism between the inflammatory mediators, blocking only one agent (5-HT) may not sufficiently inhibit the inflammatory response to tissue injury.

There have been a few studies demonstrating the ability of extremely high concentrations (1% -3% solutions—i.e., 10–30 mg per milliliter) of histamine$_1$ (H$_1$) receptor antagonists to act as local anesthetics for surgical procedures. This anesthetic effect is not believed to be mediated via H$_1$ receptors but, rather, to be due to a non-specific interaction with neuronal membrane sodium channels (similar to the action of lidocaine). Given the side effects (e.g., sedation) associated with these high "anesthetic" concentrations of histamine receptor antagonists, local administration of histamine receptor antagonists currently is not used in the perioperative setting.

III. SUMMARY OF THE INVENTION

The present invention provides a solution constituting a mixture of multiple agents in low concentrations directed at inhibiting locally the mediators of pain, inflammation, spasm and restenosis in a physiologic electrolyte carrier fluid. The invention also provides a method for perioperative delivery of the irrigation solution containing these agents directly to a surgical site, where it works locally at the receptor and enzyme levels to preemptively limit pain, inflammation, spasm and restenosis at the site. Due to the local perioperative delivery method of the present invention, a desired therapeutic effect can be achieved with lower doses of agents than are necessary when employing other methods of delivery (i.e., intravenous, intramuscular, subcutaneous and oral). The anti-pain/anti-inflammation agents in the solution include agents selected from the following classes of receptor antagonists and agonists and enzyme activators and inhibitors, each class acting through a differing molecular mechanism of action for pain and inflammation inhibition: (1) serotonin receptor antagonists; (2) serotonin receptor agonists; (3) histamine receptor antagonists; (4) bradykinin receptor antagonists; (5) kallikrein inhibitors; (6) tachykinin receptor antagonists, including neurokinin$_1$ and neurokinin$_2$ receptor subtype antagonists; (7) calcitonin gene-related peptide (CGRP) receptor antagonists; (8) interleukin receptor antagonists; (9) inhibitors of enzymes active in the synthetic pathway for arachidonic acid metabolites, including (a) phospholipase inhibitors, including PLA$_2$ isoform inhibitors and PLC$_\gamma$ isoform inhibitors, (b) cyclooxygenase inhibitors, and (c) lipooxygenase inhibitors; (10) prostanoid receptor antagonists including eicosanoid EP-1 and EP-4 receptor subtype antagonists and thromboxane receptor subtype antagonists; (11) leukotriene receptor antagonists including leukotriene B$_4$ receptor subtype antagonists and leukotriene D$_4$ receptor subtype antagonists; (12) opioid receptor agonists, including $\mu$-opioid, $\delta$-opioid, and $\kappa$-opioid receptor subtype agonists; (13) purinoceptor agonists and antagonists including P$_{2X}$ receptor antagonists and P$_{2Y}$ receptor agonists; and (14) adenosine triphosphate (ATP)-sensitive potassium channel openers. Each of the above agents functions either as an anti-inflammatory agent and/or as an anti-nociceptive, i.e., anti-pain or analgesic, agent. The selection of agents from these classes of compounds is tailored for the particular application.

Several preferred embodiments of the solution of the present invention also include anti-spasm agents for particular applications. For example, anti-spasm agents may be included alone or in combination with anti-pain/anti-inflammation agents in solutions used for vascular procedures to limit vasospasm, and anti-spasm agents may be included for urologic procedures to limit spasm in the urinary tract and bladder wall. For such applications, anti-spasm agents are utilized in the solution. For example, an anti-pain/anti-inflammation agent which also serves as an anti-spasm agent may be included. Suitable anti-inflammatory/anti-pain agents which also act as anti-spasm agents include serotonin receptor antagonists, tachykinin receptor antagonists, and ATP-sensitive potassium channel openers. Other agents which may be utilized in the solution specifically for their anti-spasm properties include calcium channel antagonists, endothelin receptor antagonists and the nitric oxide donors (enzyme activators).

Specific preferred embodiments of the solution of the present invention for use in cardiovascular and general vascular procedures include anti-restenosis agents, which most preferably are used in combination with anti-spasm agents. Suitable anti-restenosis agents include: (1) antiplatelet agents including: (a) thrombin inhibitors and receptor antagonists, (b) adenosine disphosphate (ADP) receptor antagonists (also known as purinoceptor$_1$ receptor antagonists), (c) thromboxane inhibitors and receptor antagonists and (d) platelet membrane glycoprotein receptor antagonists; (2) inhibitors of cell adhesion molecules, including (a) selectin inhibitors and (b) integrin inhibitors; (3) anti-chemotactic agents; (4) interleukin receptor antagonists (which also serve as anti-pain/anti-inflammation agents); and (5) intracellular signaling inhibitors including: (a) protein kinase C (PKC) inhibitors and protein tyrosine kinase inhibitors, (b) modulators of intracellular protein tyrosine phosphatases, (c) inhibitors of src homology$_2$ (SH2) domains, and (d) calcium channel antagonists. Such agents are useful in preventing restenosis of arteries treated by angioplasty, rotational atherectomy or other cardiovascular or general vascular therapeutic or diagnostic procedures.

The present invention also provides a method for manufacturing a medicament compounded as a dilute irrigation solution for use in continuously irrigating an operative site or wound during an operative procedure. The method entails dissolving in a physiologic electrolyte carrier fluid a plurality of anti-pain/anti-inflammatory agents, and for some applications anti-spasm agents and/or anti-restenosis agents, each agent included at a concentration of preferably no more than 100,000 nanomolar, and more preferably no more than 10,000 nanomolar.

The method of the present invention provides for the delivery of a dilute combination of multiple receptor antagonists and agonists and enzyme inhibitors and activators directly to a wound or operative site, during therapeutic or diagnostic procedures for the inhibition of pain, inflammation, spasm and restenosis. Since the active ingredients in the solution are being locally applied directly to the operative tissues in a continuous fashion, the drugs may be used efficaciously at extremely low doses relative to those doses required for therapeutic effect when the same drugs are delivered orally, intramuscularly, subcutaneously or intravenously. As used herein, the term "local" encompasses application of a drug in and around a wound or other operative site, and excludes oral, subcutaneous, intravenous and intramuscular administration. The term "continuous" as used herein encompasses uninterrupted application, repeated application at frequent intervals (e.g., repeated intravascular boluses at frequent intervals intraprocedurally), and applications which are uninterrupted except for brief cessations such as to permit the introduction of other drugs or agents or procedural equipment, such that a substantially constant predetermined concentration is maintained locally at the wound or operative site.

The advantages of low dose applications of agents are three-fold. The most important is the absence of systemic side effects which often limit the usefulness of these agents. Additionally, the agents selected for particular applications in the solutions of the present invention are highly specific with regard to the mediators on which they work. This specificity is maintained by the low dosages utilized. Finally, the cost of these active agents per operative procedure is low.

The advantages of local administration of the agents via luminal irrigation or other fluid application are the following: (1) local administration guarantees a known concentration at the target site, regardless of interpatient variability in metabolism, blood flow, etc.; (2) because of the direct mode of delivery, a therapeutic concentration is obtained instantaneously and, thus, improved dosage control is provided; and (3) local administration of the active agents directly to a wound or operative site also substantially reduces degradation of the agents through extracellular processes, e.g., first- and second-pass metabolism, that would otherwise occur if the agents were given orally, intravenously, subcutaneously or intramuscularly. This is particularly true for those active agents that are peptides, which are metabolized rapidly. Thus, local administration permits the use of compounds or agents which otherwise could not be employed therapeutically. For example, some agents in the following classes are peptidic: bradykinin receptor antagonists; tachykinin receptor antagonists; opioid receptor agonists; CGRP receptor antagonists; and interleukin receptor antagonists. Local, continuous delivery to the wound or operative site minimizes drug degradation or metabolism while also providing for the continuous replacement of that portion of the agent that may be degraded, to ensure that a local therapeutic concentration, sufficient to maintain receptor occupancy, is maintained throughout the duration of the operative procedure.

Local administration of the solution perioperatively throughout a surgical procedure in accordance with the present invention produces a preemptive analgesic, anti-inflammatory, anti-spasmodic or anti-restenotic effect. As used herein, the term "perioperative" encompasses application intraprocedurally, pre- and intraprocedurally, intra- and postprocedurally, and pre-, intra- and postprocedurally. To maximize the preemptive anti-inflammatory, analgesic (for certain applications), antispasmodic (for certain applications) and antirestenotic (for certain applications) effects, the solutions of the present invention are most preferably applied pre-, intra- and postoperatively. By occupying the target receptors or inactivating or activating targeted enzymes prior to the initiation of significant operative trauma locally, the agents of the present solution modulate specific pathways to preemptively inhibit the targeted pathologic process. If inflammatory mediators and processes are preemptively inhibited in accordance with the present invention before they can exert tissue damage, the benefit is more substantial than if given after the damage has been initiated.

Inhibiting more than one inflammatory, spasm or restenosis mediator by application of the multiple agent solution of the present invention has been shown to dramatically reduce the degree of inflammation, pain, and spasm, and theoretically should reduce restenosis. The irrigation solutions of the present invention include combinations of drugs, each solution acting on multiple receptors or enzymes. The drug agents are thus simultaneously effective against a combination of pathologic processes, including pain and inflammation, vasospasm, smooth muscle spasm and restenosis. The action of these agents is considered to be synergistic, in that the multiple receptor antagonists and inhibitory agonists of the present invention provide a disproportionately increased efficacy in combination relative to the efficacy of the individual agents. The synergistic action of several of the agents of the present invention are discussed, by way of example, below in the detailed descriptions of those agents.

In addition to arthroscopy, the solution of the present invention may also be applied locally to any human body cavity or passage, operative wound, traumatic wound (e.g., burns) or in any operative/interventional procedure in which irrigation can be performed. These procedures include, but are not limited to, urological procedures, cardiovascular and general vascular diagnostic and therapeutic procedures, endoscopic procedures and oral, dental and periodontal procedures. As used hereafter, the term "wound", unless otherwise specified, is intended to include surgical wounds, operative/interventional sites, traumatic wounds and burns.

Used perioperatively, the solution should result in a clinically significant decrease in operative site pain and inflammation relative to currently-used irrigation fluids, thereby decreasing the patient's postoperative analgesic (i.e., opiate) requirement and, where appropriate, allowing earlier patient mobilization of the operative site. No extra effort on the part of the surgeon and operating room personnel is required to use the present solution relative to conventional irrigation fluids.

IV. BRIEF DESCRIPTION OF THE DRAWINGS

The present invention will now be described in greater detail, by way of example, with reference to the accompanying drawings in which:

FIG. 1 provides a schematic overview of a generic vascular cell showing molecular targets and flow of signaling information leading to contraction, secretion and/or proliferation. The integration of extrinsic signals through receptors, ion channels and other membrane proteins are common to platelets, neutrophils, endothelial cells and smooth muscle cells. Representative examples of molecular targets are included for major groups of molecules which are therapeutic targets of drugs included in the solutions of the present invention.

FIG. 2 provides a detailed diagram of the signaling pathways illustrating "crosstalk" between G-protein coupled receptor (GPCR) pathways and receptor tyrosine kinase (RTK) pathways in a vascular smooth muscle cell. Only representative proteins in each pathway have been shown to simplify the flow of information. Activation of GPCRs leads to increases in intracellular calcium and increased protein kinase C (PKC) activity and subsequent smooth muscle contraction or spasm. In addition, "crosstalk" to the RTK signaling pathway occurs through activation of PYK2 (a newly discovered protein tyrosine kinase) and PTK-X (an undefined protein tyrosine kinase), triggering proliferation. Conversely, while activation of RTKs directly initiates proliferation, "crosstalk" to the GPCR pathway occurs at the level of PKC activity and calcium levels. LGR designates ligand-gated receptor, and MAPK designates mitogen-activated protein kinase. These interactions define the basis for synergistic interactions between molecular targets mediating spasm and restenosis. The GPCR signaling pathway also mediates signal transduction (FIGS. 3 and 7) leading to pain transmission in other cell types (e.g., neurons).

FIG. 3 provides a diagram of the G-Protein Coupled Receptor (GPCR) pathway. Specific molecular sites of action for some drugs in a preferred arthroscopic solution of the present invention are identified.

FIG. 4 provides a diagram of the G-Protein Coupled Receptor (GPCR) pathway including the signaling proteins responsible for ""crosstalk"" with the Growth Factor Receptor signaling pathway. Specific molecular sites of action for some drugs in a preferred cardiovascular and general vascular solution of the present invention are identified. (See also FIG. 5).

Figure 5:
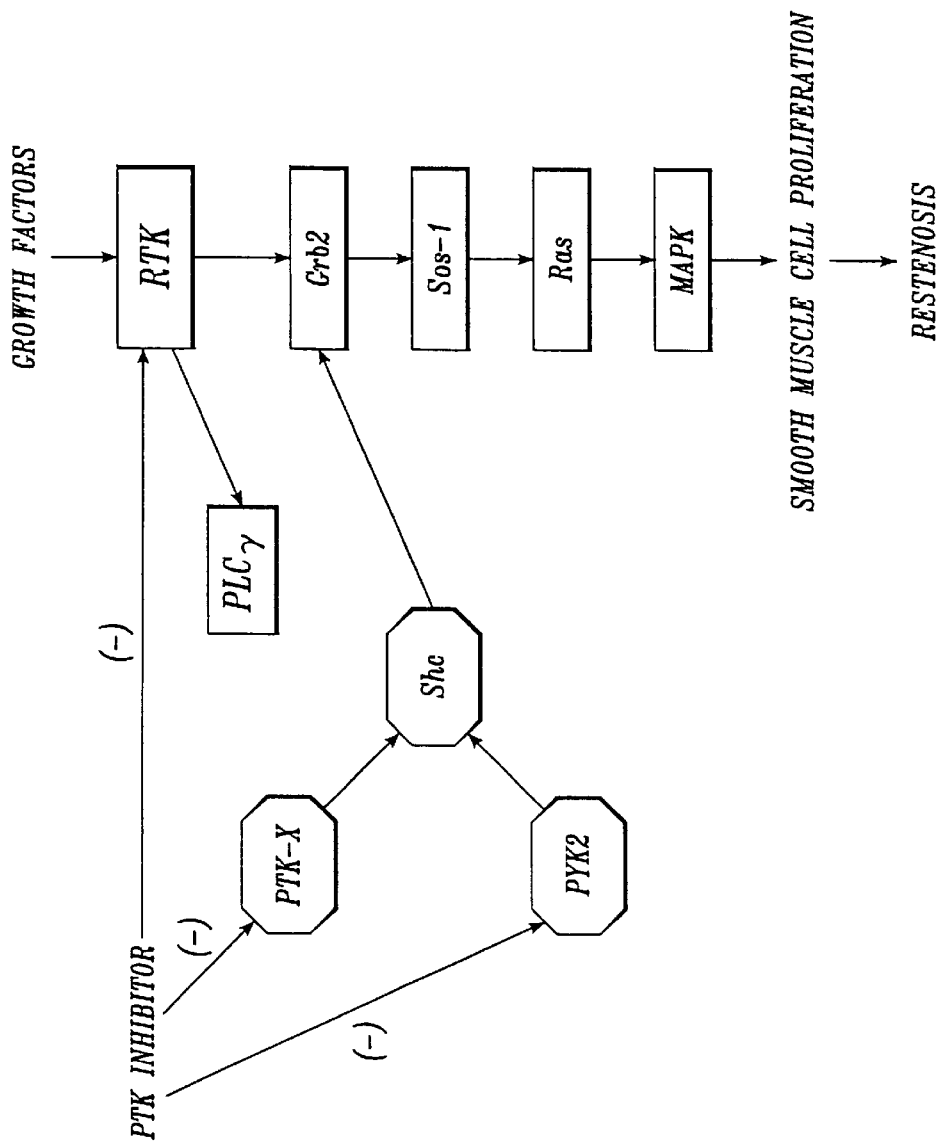

FIG. 5 provides a diagram of the Growth Factor Receptor signaling pathway including the signaling proteins responsible for ""crosstalk"" with the G-Protein Coupled Receptor signaling pathway. Specific molecular sites of action for some drugs in a preferred cardiovascular and general vascular solution of the present invention are identified. (See also FIG. 4).

Figure 6:
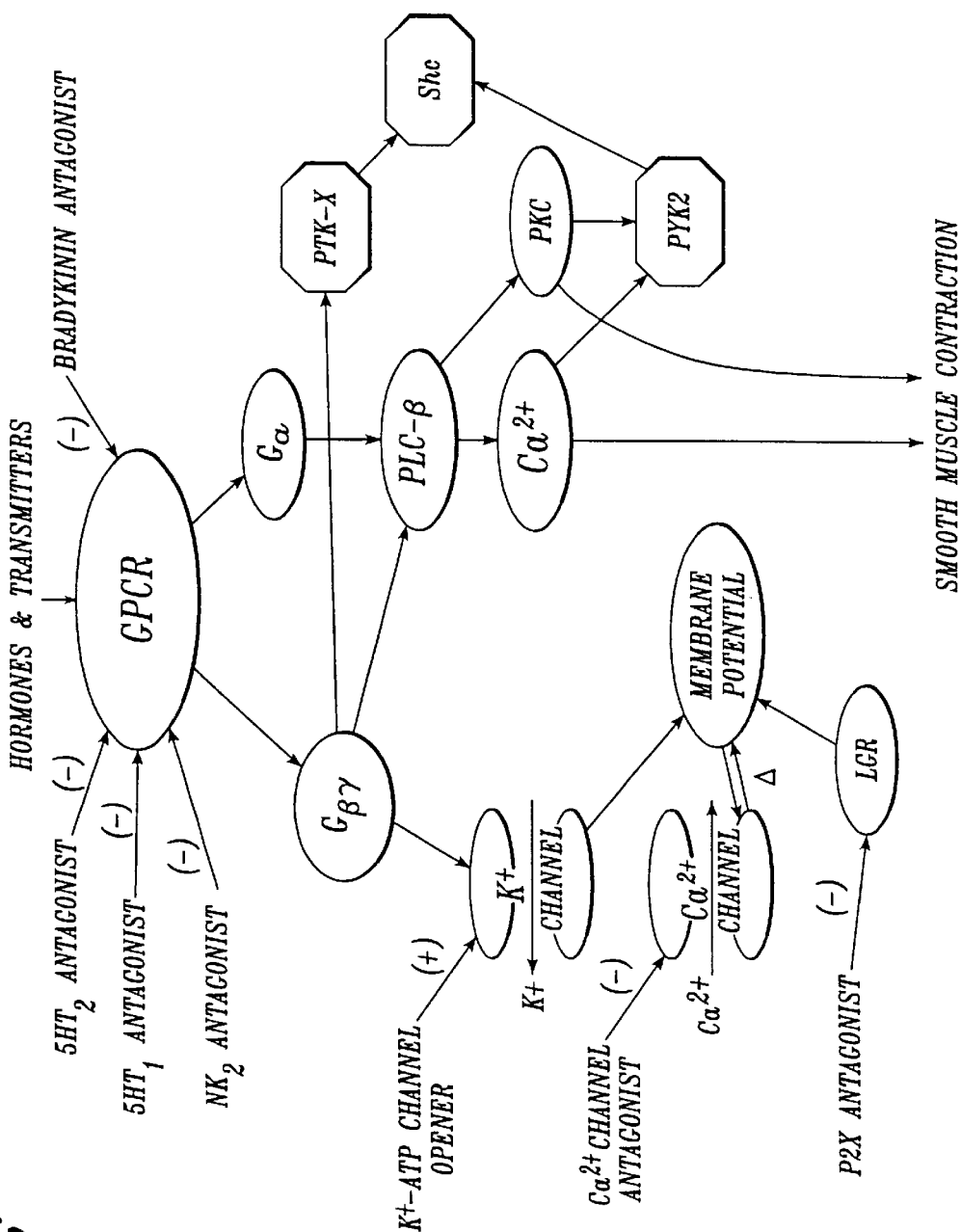

FIG. 6 provides a diagram of the G-Protein Coupled Receptor pathway including the signaling proteins responsible for ""crosstalk"" with the Growth Factor Receptor signaling pathway. Specific molecular sites of action for some drugs in a preferred urologic solution are identified.

FIG. 7 provides a diagram of the G-Protein Coupled Receptor pathway. Specific molecular sites of action for some drugs in a preferred general surgical wound solution of the present invention are identified.

Figure 8:
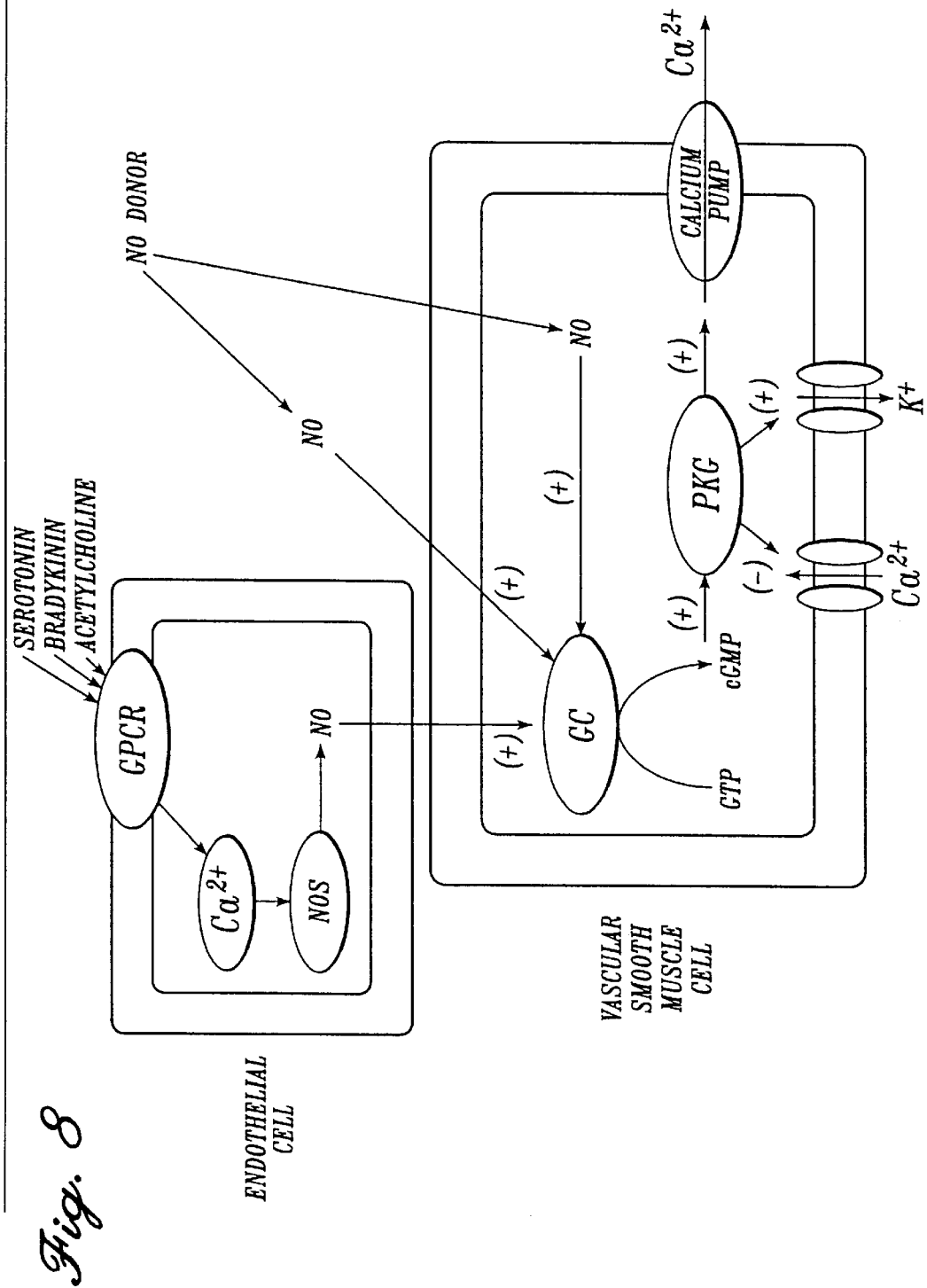

FIG. 8 provides a diagram of the mechanism of action of nitric oxide (NO) donor drugs and NO causing relaxation of vascular smooth muscle. Physiologically, certain hormones and transmitters can activate a form of NO synthase in the endothelial cell through elevated intracellular calcium resulting in increased synthesis of NO. NO donors may generate NO extracellularly or be metabolized to NO within the smooth muscle cell. Extracellular NO can diffuse across the endothelial cell or directly enter the smooth muscle cell. The primary target of NO is the soluble guanylate cyclase (GC), leading to activation of a cGMP-dependent protein kinase (PKG) and subsequent extrusion of calcium from the smooth muscle cell via a membrane pump. NO also hyperpolarizes the cell by opening potassium channels which in turn cause closure of voltage-sensitive calcium channels. Thus, the synergistic interactions of calcium channel antagonists, potassium channel openers and NO donors are evident from the above signal transduction pathway.

Figure 9:
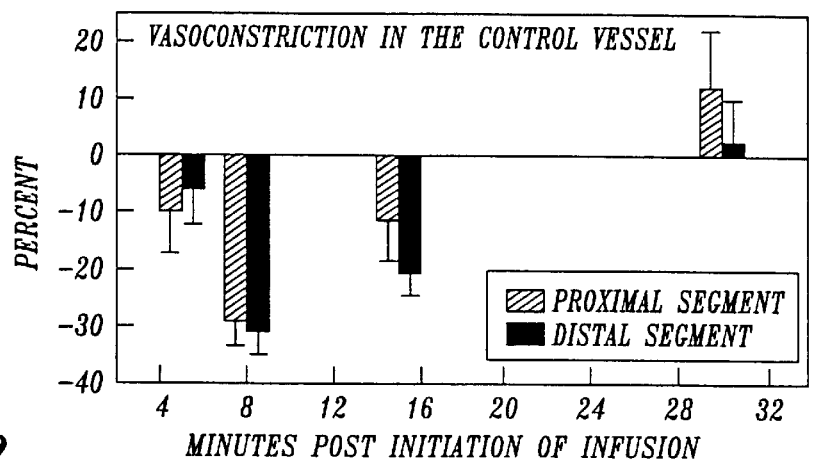
Figure 10A:
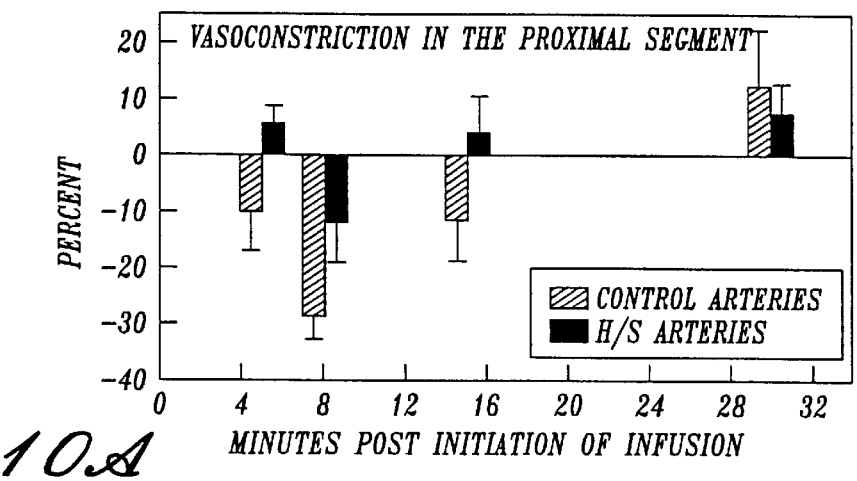
Figure 10B:
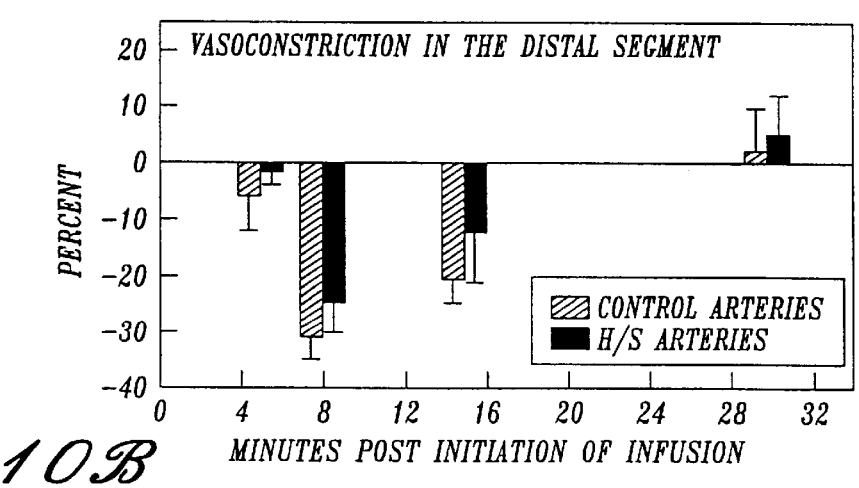

FIGS. 9, 10A and 10B provide charts of the percent of vasoconstriction versus time in control arteries, in the proximal segment of subject arteries, and in the distal segment of subject arteries, respectively, for the animal study described in EXAMPLE XI herein demonstrating the effect on vasoconstriction of infusion with histamine and serotonin antagonists, used in the solutions of the present invention, during balloon angioplasty.

Figure 11:
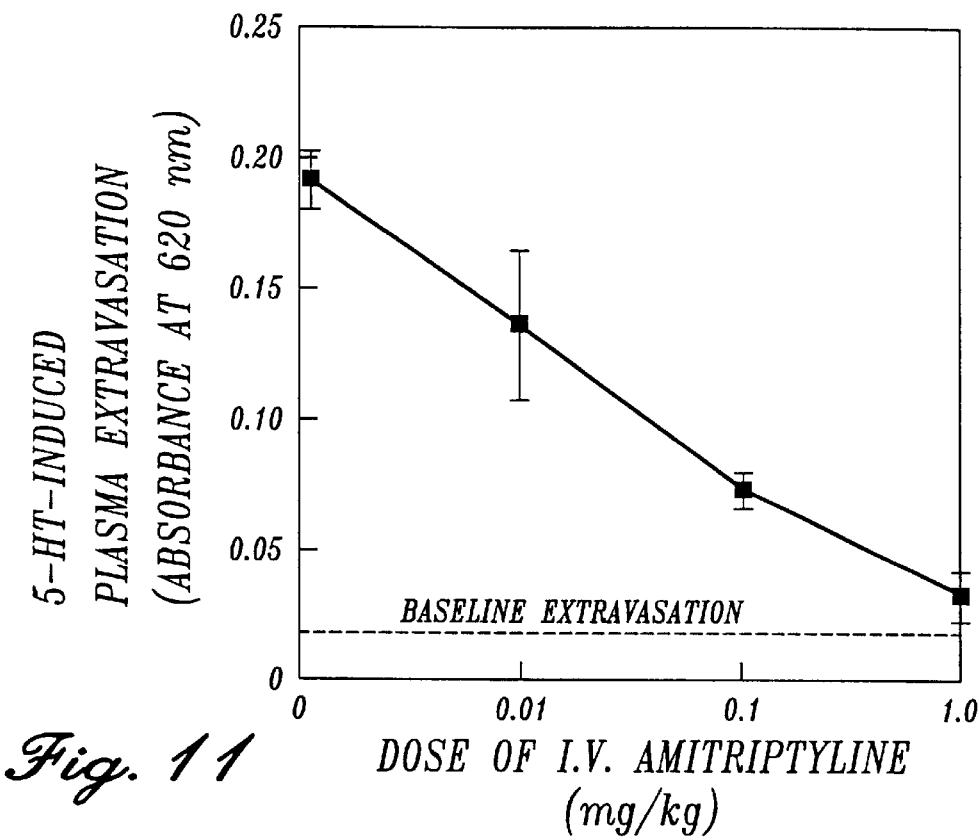
Figure 12:
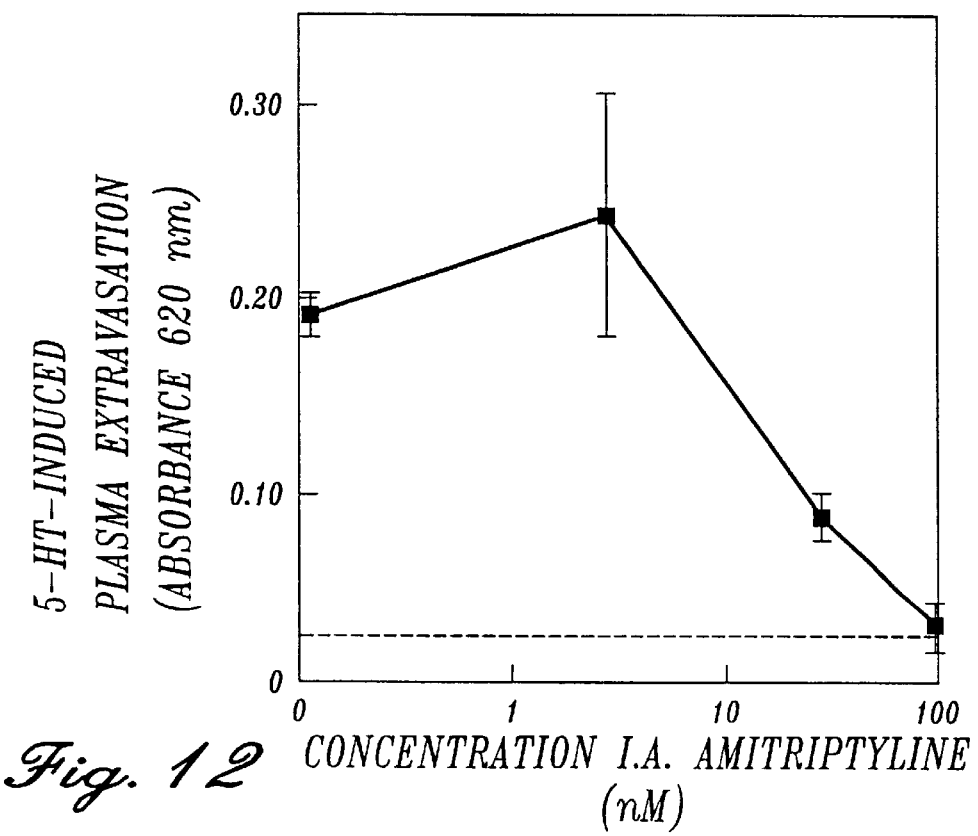

FIGS. 11 and 12 provide charts of plasma extravasation versus dosage of amitriptyline, used in the solutions of the present invention, delivered intravenously and intraarticularly, respectively, to knee joints in which extravasation has been induced by introduction of 5-hydroxytryptamine in the animal study described in EXAMPLE XII herein.

Figure 13:
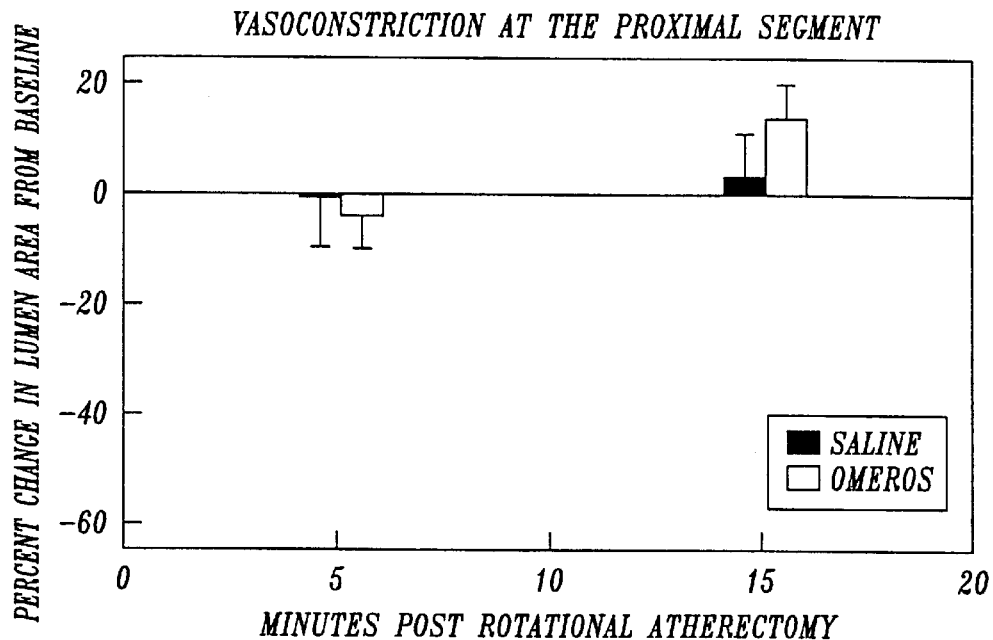
Figure 14:
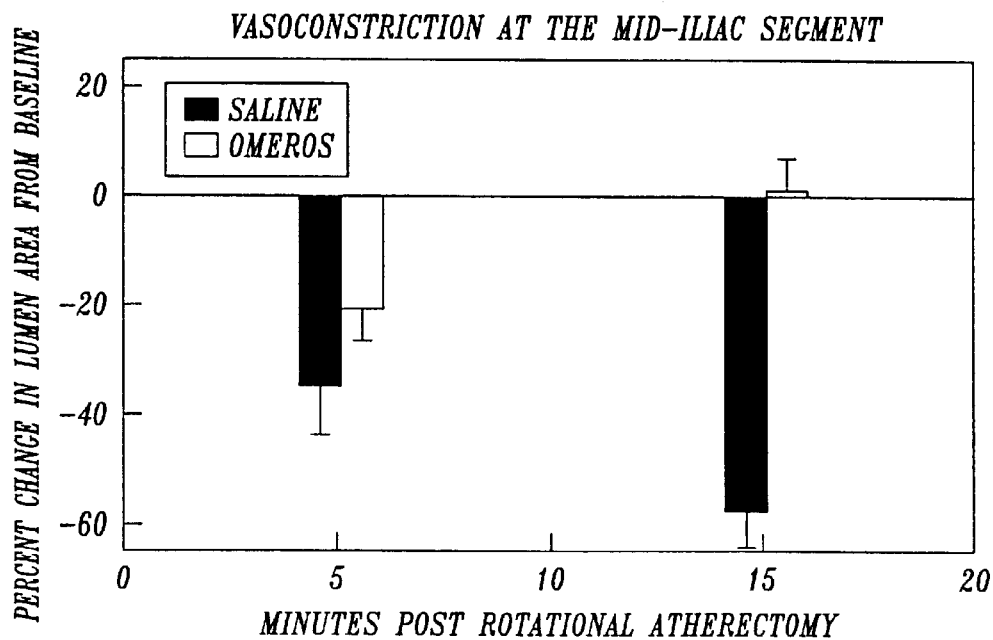
Figure 15:
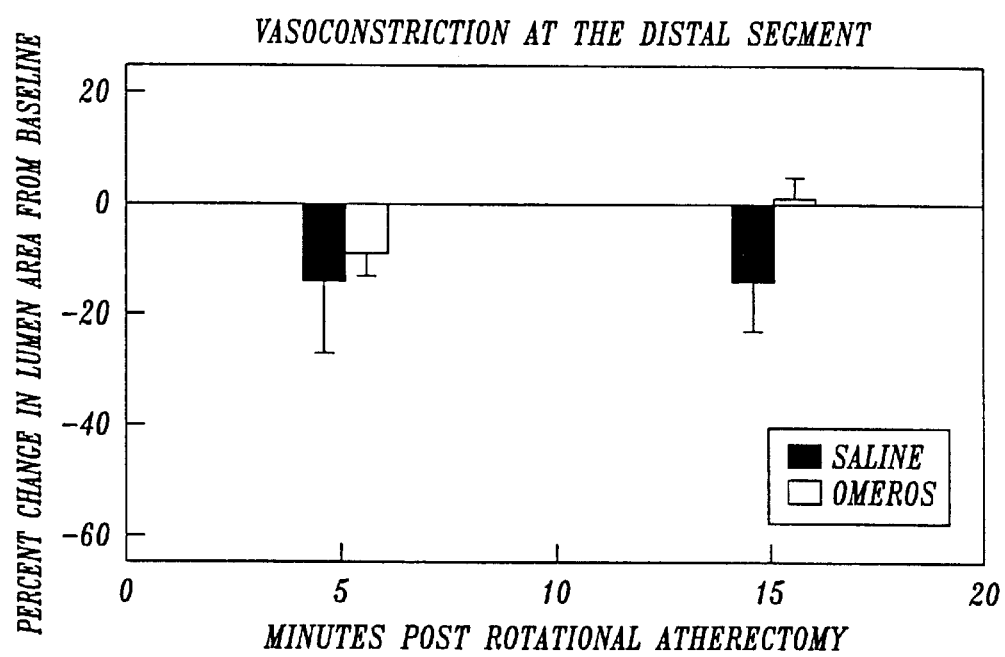

FIGS. 13, 14 and 15 provide charts of mean vasoconstriction (negative values) or vasodilation (positive values), ±1 standard error of the mean for the proximal (FIG. 13), mid (FIG. 14) and distal (FIG. 15) segments of arteries treated with saline (N=4) or with a solution formulated in accordance with the present invention (N=7), at the immediate and 15 minute post-rotational atherectomy time points in the animal study of Example XIII described herein.

V. DETAILED DESCRIPTION OF THE PREFERRED EMBODIMENT

The irrigation solution of the present invention is a dilute solution of multiple pain/inflammation inhibitory agents, anti-spasm agents and anti-restenosis agents in a physiologic carrier. The carrier is a liquid, which as used herein is intended to encompass biocompatible solvents, suspensions, polymerizable and non-polymerizable gels, pastes and salves. Preferably, the carrier is an aqueous solution which may include physiologic electrolytes, such as normal saline or lactated Ringer's solution.

The anti-inflammation/anti-pain agents are selected from the group consisting of: (1) serotonin receptor antagonists; (2) serotonin receptor agonists; (3) histamine receptor antagonists; (4) bradykinin receptor antagonists; (5) kallikrein inhibitors; (6) tachykinin receptor antagonists, including neurokinin$_1$ and neurokinin$_2$ receptor subtype antagonists; (7) calcitonin gene-related peptide (CGRP) receptor antagonists; (8) interleukin receptor antagonists; (9) inhibitors of enzymes active in the synthetic pathway for arachidonic acid metabolites, including (a) phospholipase inhibitors, including PLA$_2$ isoform inhibitors and PLC$_\gamma$ isoform inhibitors, (b) cyclooxygenase inhibitors, and (c) lipooxygenase inhibitors; (10) prostanoid receptor antagonists including eicosanoid EP-1 and EP-4 receptor subtype antagonists and thromboxane receptor subtype antagonists; (11) leukotriene receptor antagonists including leukotriene B$_4$ receptor subtype antagonists and leukotriene D$_4$ receptor subtype antagonists; (12) opioid receptor agonists, including $\mu$-opioid, $\delta$-opioid, and $\kappa$-opioid receptor subtype agonists; (13) purinoceptor agonists and antagonists including P$_{2X}$ receptor antagonists and P$_{2Y}$ receptor agonists; and (14) adenosine triphosphate (ATP)-sensitive potassium channel openers.

Suitable anti-inflammatory/anti-pain agents which also act as anti-spasm agents include serotonin receptor antagonists, tachykinin receptor antagonists, ATP-sensitive potassium channel openers and calcium channel antagonists. Other agents which may be utilized in the solution specifically for their anti-spasm properties include endothelin receptor antagonists, calcium channel antagonists and the nitric oxide donors (enzyme activators).

Specific preferred embodiments of the solution of the present invention for use in cardiovascular and general vascular procedures include anti-restenosis agents, which most preferably are used in combination with anti-spasm agents. Suitable anti-restenosis agents include: (1) antiplatelet agents including: (a) thrombin inhibitors and receptor antagonists, (b) adenosine disphosphate (ADP) receptor antagonists (also known as purinoceptor$_1$ receptor antagonists), (c) thromboxane inhibitors and receptor antagonists and (d) platelet membrane glycoprotein receptor antagonists; (2) inhibitors of cell adhesion molecules, including (a) selectin inhibitors and (b) integrin inhibitors; (3) anti-chemotactic agents; (4) interleukin receptor antagonists (which also serve as anti-pain/anti-inflammation agents); and (5) intracellular signaling inhibitors including: (a) protein kinase C (PKC) inhibitors and protein tyrosine phosphatases, (b) modulators of intracellular protein tyrosine kinase inhibitors, (c) inhibitors of src homology$_2$ (SH2) domains, and (d) calcium channel antagonists. Such agents are useful in preventing restenosis of arteries treated by angioplasty, rotational atherectomy or other cardiovascular or general vascular therapeutic procedure.

In each of the surgical solutions of the present invention, the agents are included in low concentrations and are delivered locally in low doses relative to concentrations and doses required with conventional methods of drug administration to achieve the desired therapeutic effect. It is impossible to obtain an equivalent therapeutic effect by delivering similarly dosed agents via other (i.e., intravenous, subcutaneous, intramuscular or oral) routes of drug administration since drugs given systemically are subject to first- and second-pass metabolism. The concentration of each agent is determined in part based on its dissociation constant, $K_d$. As used herein, the term "dissociation constant" is intended to encompass both the equilibrium dissociation constant for its respective agonist-receptor or antagonist-receptor interaction and the equilibrium inhibitory constant for its respective activator-enzyme or inhibitor-enzyme interaction. Each agent is preferably included at a low concentration of 0.1 to 10,000 times $K_d$ nanomolar, except for cyclooxygenase inhibitors, which may be required at larger concentrations depending on the particular inhibitor selected. Preferably, each agent is included at a concentration of 1.0 to 1,000 times $K_d$ nanomolar and most preferably at approximately 100 times $K_d$ nanomolar. These concentrations are adjusted as needed to account for dilution in the absence of metabolic transformation at the local delivery site. The exact agents selected for use in the solution, and the concentration of the agents, varies in accordance with the particular application, as described below.

A solution in accordance with the present invention can include just a single or multiple pain/inflammation inhibitory agent(s), a single or multiple anti-spasm agent(s), a combination of both anti-spasm and pain/inflammation inhibitory agents, or anti-restenosis agents from the enumerated classes, at low concentration. However, due to the aforementioned synergistic effect of multiple agents, and the desire to broadly block pain and inflammation, spasm and restenosis, it is preferred that multiple agents be utilized.

The surgical solutions constitute a novel therapeutic approach by combining multiple pharmacologic agents acting at distinct receptor and enzyme molecular targets. To date, pharmacologic strategies have focused on the development of highly specific drugs that are selective for individual receptor subtypes and enzyme isoforms that mediate responses to individual signaling neurotransmitters and hormones. As an example, endothelin peptides are some of the most potent vasoconstrictors known. Selective antagonists that are specific for subtypes of endothelin (ET) receptors are being sought by several pharmaceutical companies for use in the treatment of numerous disorders involving elevated endothelin levels in the body. Recognizing the potential role of the receptor subtype ET$_A$ in hypertension, these drug companies specifically are targeting the development of selective antagonists to the ET$_A$ receptor subtype for the anticipated treatment of coronary vasospasm. This standard pharmacologic strategy, although well accepted, is not optimal since many other vasoconstrictor agents (e.g., serotonin, prostaglandin, eicosanoid, etc.) simultaneously may be responsible for initiating and maintaining a vasospastic episode (see FIGS. 2 and 4). Furthermore, despite inactivation of a single receptor subtype or enzyme, activation of other receptor subtypes or enzymes and the resultant signal transmission often can trigger a cascade effect. This explains the significant difficulty in employing a single receptor-specific drug to block a pathophysiologic process in which multiple transmitters play a role. Therefore, targeting only a specific individual receptor subtype, such as ET$_A$, is likely to be ineffective.

In contrast to the standard approach to pharmacologic therapy, the therapeutic approach of the present surgical solutions is based on the rationale that a combination of drugs acting simultaneously on distinct molecular targets is required to inhibit the full spectrum of events that underlie the development of a pathophysiologic state. Furthermore, instead of targeting a specific receptor subtype alone, the surgical solutions are composed of drugs that target common molecular mechanisms operating in different cellular physiologic processes involved in the development of pain, inflammation, vasospasm, smooth muscle spasm and restenosis (see FIG. 1). In this way, the cascading of additional receptors and enzymes in the nociceptive, inflammatory, spasmodic and restenotic pathways is minimized by the surgical solutions. In these pathophysiologic pathways, the surgical solutions inhibit the cascade effect both "upstream" and "downstream".

An example of "upstream" inhibition is the cyclooxygenase antagonists in the setting of pain and inflammation. The cyclooxygenase enzymes ($COX_1$ and $COX_2$) catalyze the conversion of arachidonic acid to prostaglandin H which is an intermediate in the biosynthesis of inflammatory and nociceptive mediators including prostaglandins, leukotrienes, and thromboxanes. The cyclooxygenase inhibitors block "upstream" the formation of these inflammatory and nociceptive mediators. This strategy precludes the need to block the interactions of the seven described subtypes of prostanoid receptors with their natural ligands. A similar "upstream" inhibitor included in the surgical solutions is aprotinin, a kallikrein inhibitor. The enzyme kallikrein, a serine protease, cleaves the high molecular weight kininogens in plasma to produce bradykinins, important mediators of pain and inflammation. By inhibition of kallikrein, aprotinin effectively inhibits the synthesis of bradykinins, thereby providing an effective "upstream" inhibition of these inflammatory mediators.

The surgical solutions also make use of "downstream" inhibitors to control the pathophysiologic pathways. In vascular smooth muscle preparations that have been precontracted with a variety of neurotransmitters (e.g., serotonin, histamine, endothelin, and thromboxane) implicated in coronary vasospasm, ATP-sensitive potassium channel openers (KCOs) produce smooth muscle relaxation which is concentration dependent (Quast et al., 1994; Kashiwabara et al., 1994). The KCOs, therefore, provide a significant advantage to the surgical solutions in the settings of vasospasm and smooth muscle spasm by providing "downstream" antispasmodic effects that are independent of the physiologic combination of agonists initiating the spasmodic event (see FIGS. 2 and 4). Similarly, NO donors and voltage-gated calcium channel antagonists can limit vasospasm and smooth muscle spasm initiated by multiple mediators known to act earlier in the spasmodic pathway.

The following is a description of suitable drugs falling in the aforementioned classes of anti-inflammation/anti-pain agents, as well as suitable concentrations for use in solutions of the present invention. While not wishing to be limited by theory, the justification behind the selection of the various classes of agents which is believed to render the agents operative is also set forth.

A. Serotonin Receptor Antagonists

Serotonin (5-HT) is thought to produce pain by stimulating $serotonin_2$ ($5-HT_2$) and/or $serotonin_3$ ($5-HT_3$) receptors on nociceptive neurons in the periphery. Most researchers agree that $5-HT_3$ receptors on peripheral nociceptors mediate the immediate pain sensation produced by 5-HT (Richardson et al., 1985). In addition to inhibiting 5-HT-induced pain, $5-HT_3$ receptor antagonists, by inhibiting nociceptor activation, also may inhibit neurogenic inflammation. Barnes P. J., et al., *Modulation of Neurogenic Inflammation: Novel Approaches to Inflammatory Disease*, Trends in Pharmacological Sciences 11, pp. 185–189 (1990). A study in rat ankle joints, however, claims the $5-HT_2$ receptor is responsible for nociceptor activation by 5-HT. Grubb, B. D., et al., *A Study of 5-HT-Receptors Associated with Afferent Nerves Located in Normal and Inflamed Rat Ankle Joints*, Agents Actions 25, pp. 216–18 (1988). Therefore, activation of $5-HT_2$ receptors also may play a role in peripheral pain and neurogenic inflammation.

One goal of the solution of the present invention is to block pain and a multitude of inflammatory processes. Thus, $5-HT_2$ and $5-HT_3$ receptor antagonists are both suitably used, either individually or together, in the solution of the present invention, as shall be described subsequently. Amitriptyline (Elavil™) is a suitable $5-HT_2$ receptor antagonist for use in the present invention. Amitriptyline has been used clinically for numerous years as an anti-depressant, and is found to have beneficial effects in certain chronic pain patients. Metoclopramide (Reglan™) is used clinically as an anti-emetic drug, but displays moderate affinity for the $5-HT_3$ receptor and can inhibit the actions of 5-HT at this receptor, possibly inhibiting the pain due to 5-HT release from platelets. Thus, it also is suitable for use in the present invention.

Other suitable $5-HT_2$ receptor antagonists include imipramine, trazodone, desipramine and ketanserin. Ketanserin has been used clinically for its anti-hypertensive effects. Hedner, T., et al., *Effects of a New Serotonin Antagonist, Ketanserin, in Experimental and Clinical Hypertension*, Am J of Hypertension, pp. 317s–23s (Jul. 1988). Other suitable $5-HT_3$ receptor antagonists include cisapride and ondansetron. The cardiovascular and general vascular solution also may contain a $serotonin_{1B}$ (also known as $serotonin_{1D\beta}$) antagonist because serotonin has been shown to produce significant vascular spasm via activation of the $serotonin_{1B}$ receptors in humans. Kaumann, A. J., et al., *Variable Participation of 5-HT1-Like Receptors and 5-HT2 Receptors in Serotonin-Induced Contraction of Human Isolated Coronary Arteries*, Circulation 90, pp. 1141–53 (1994). Suitable $serotonin_{1B}$ receptor antagonists include yohimbine, N-[-methoxy-3-(4-methyl-1-piperanzinyl) phenyl]-2'-methyl-4'-(5-methyl-1,2,4-oxadiazol-3-yl)[1,1-biphenyl]-4-carboxamide ("GR127935") and methiothepin. Therapeutic and preferred concentrations for use of these drugs in the solution of the present invention are set forth in Table 1.

TABLE 1

Therapeutic and Preferred Concentrations of Pain/Inflammation Inhibitory Agents

| Class of Agent | Therapeutic Concentrations (Nanomolar) | Preferred Concentrations (Nanomolar) |
| --- | --- | --- |
| $Serotonin_2$ Receptor Antagonists: | | |
| amitriptyline | 0.1–1,000 | 50–500 |
| imipramine | 0.1–1,000 | 50–500 |
| trazodone | 0.1–2,000 | 50–500 |
| desipramine | 0.1–1,000 | 50–500 |
| ketanserin | 0.1–1,000 | 50–500 |
| $Serotonin_3$ Receptor Antagonists: | | |
| tropisetron | 0.01–100 | 0.05–50 |

TABLE 1-continued

Therapeutic and Preferred Concentrations
of Pain/Inflammation Inhibitory Agents

| Class of Agent | Therapeutic Concentrations (Nanomolar) | Preferred Concentrations (Nanomolar) |
| --- | --- | --- |
| metoclopramide | 10–10,000 | 200–2,000 |
| cisapride | 0.1–1,000 | 20–200 |
| ondansetron | 0.1–1,000 | 20–200 |
| Serotonin$_{1B}$ (Human 1D$_\beta$) Antagonists: | | |
| yohimbine | 0.1–1,000 | 50–500 |
| GR127935 | 0.1–1,000 | 10–500 |
| methiothepin | 0.1–500 | 1–100 |

B. Serotonin Receptor Agonists

5-HT$_{1A}$, 5-HT$_{1B}$ and 5-HT$_{1D}$ receptors are known to inhibit adenylate cyclase activity. Thus including a low dose of these serotonin$_{1A}$, serotonin$_{1B}$ and serotonin$_{1D}$ receptor agonists in the solution should inhibit neurons mediating pain and inflammation. The same action is expected from serotonin$_{1E}$ and serotonin$_{1F}$ receptor agonists because these receptors also inhibit adenylate cyclase.

Buspirone is a suitable 1A receptor agonist for use in the present invention. Sumatriptan is a suitable 1A, 1B, 1D and 1F receptor agonist. A suitable 1B and 1D receptor agonist is dihydroergotamine. A suitable 1E receptor agonist is ergonovine. Therapeutic and preferred concentrations for these receptor agonists are provided in Table 2.

TABLE 2

Therapeutic and Preferred Concentrations
of Pain/Inflammation Inhibitory Agents

| Class of Agent | Therapeutic Concentrations (Nanomolar) | Preferred Concentrations (Nanomolar) |
| --- | --- | --- |
| Serotonin$_{1A}$ Agonists: | | |
| buspirone | 1–1,000 | 10–200 |
| sumatriptan | 1–1,000 | 10–200 |
| Serotonin$_{1B}$ Agonists: | | |
| dihydroergotamine | 0.1–1,000 | 10–100 |
| sumatriptan | 1–1,000 | 10–200 |
| Serotonin$_{1D}$ Agonists: | | |
| dihydroergotamine | 0.1–1,000 | 10–100 |
| sumatriptan | 1–1,000 | 10–200 |
| Serotonin$_{1E}$ Agonists: | | |
| ergonovine | 10–2,000 | 100–1,000 |
| Serotonin$_{1F}$ Agonists: | | |
| sumatriptan | 1–1,000 | 10–200 |

C. Histamine Receptor Antagonists

Histamine receptors generally are divided into histamine$_1$ (H$_1$) and histamine$_2$ (H$_2$) subtypes. The classic inflammatory response to the peripheral administration of histamine is mediated via the H$_1$ receptor. Douglas, 1985. Therefore, the solution of the present invention preferably includes a histamine H$_1$ receptor antagonist. Promethazine (Phenergan™) is a commonly used anti-emetic drug which potently blocks H$_1$ receptors, and is suitable for use in the present invention. Interestingly, this drug also has been shown to possess local anesthetic effects but the concentrations necessary for this effect are several orders higher than that necessary to block H1 receptors, thus, the effects are believed to occur by different mechanisms. The histamine receptor antagonist concentration in the solution is sufficient to inhibit H$_1$ receptors involved in nociceptor activation, but not to achieve a "local anesthetic" effect, thereby eliminating the concern regarding systemic side effects.

Histamine receptors also are known to mediate vasomotor tone in the coronary arteries. In vitro studies in the human heart have demonstrated that the histamine$_1$ receptor subtype mediates contraction of coronary smooth muscle. Ginsburg, R., et al., *Histamine Provocation of Clinical Coronary Artery Spasm: Implications Concerning Pathogenesis of Variant Angina Pectoris*, American Heart J., Vol. 102, pp. 819–822, (1980). Some studies suggest that histamine-induced hypercontractility in the human coronary system is most pronounced in the proximal arteries in the setting of atherosclerosis and the associated denudation of the arterial endothelium. Keitoku, M. et al., *Different Histamine Actions in Proximal and Distal Human Coronary Arteries in Vitro*, Cardiovascular Research 24, pp. 614–622, (1990). Therefore, histamine receptor antagonists may be included in the cardiovascular irrigation solution.

Other suitable H$_1$ receptor antagonists include terfenadine, diphenhydramine, amitriptyline, mepyramine and tripolidine. Because amitriptyline is also effective as a serotonin$_2$ receptor antagonist, it has a dual function as used in the present invention. Suitable therapeutic and preferred concentrations for each of these H$_1$ receptor antagonists are set forth in Table 3.

TABLE 3

Therapeutic and Preferred Concentrations
of Pain/Inflammation Inhibitory Agents

| Class of Agent | Therapeutic Concentrations (Nanomolar) | Preferred Concentrations (Nanomolar) |
| --- | --- | --- |
| Histamine$_1$ Receptor Antagonists: | | |
| promethazine | 0.1–1,000 | 50–200 |
| diphenhydramine | 0.1–1,000 | 50–200 |
| amitriptyline | 0.1–1,000 | 50–500 |
| terfenadine | 0.1–1,000 | 50–500 |
| mepyramine (pyrilamine) | 0.1–1,000 | 5–200 |
| tripolidine | 0.01–100 | 5–20 |

D. Bradykinin Receptor Antagonists

Bradykinin receptors generally are divided into bradykinin$_1$ (B$_1$) and bradykinin$_2$ (B$_2$) subtypes. Studies have shown that acute peripheral pain and inflammation produced by bradykinin are mediated by the B$_2$ subtype, whereas bradykinin-induced pain in the setting of chronic inflammation is mediated via the B$_1$ subtype. Perkins, M. N., et al., *Antinociceptive Activity of the Bradykinin B1 and B2 Receptor Antagonists, des-Arg$^9$, [Leu$^8$]-BK and HOE 140, in Two Models of Persistent Hyperalgesia in the Rat*, Pain 53, pp. 191–97 (1993); Dray, A., et al., *Bradykinin and Inflammatory Pain*, Trends Neurosci 16, pp. 99–104 (1993), each of which references is hereby expressly incorporated by reference.

At present, bradykinin receptor antagonists are not used clinically. These drugs are peptides (small proteins), and thus they cannot be taken orally, because they would be digested. Antagonists to B$_2$ receptors block bradykinin-induced acute pain and inflammation. Dray et al., 1993. B$_1$ receptor antagonists inhibit pain in chronic inflammatory conditions. Perkins et al., 1993; Dray et al., 1993. Therefore, depending on the application, the solution of the present invention preferably includes either or both bradykinin B$_1$ and $B_2$ receptor antagonists. For example, arthroscopy is performed for both acute and chronic conditions, and thus an irrigation solution for arthroscopy could include both $B_1$ and $B_2$ receptor antagonists.

Suitable bradykinin receptor antagonists for use in the present invention include the following bradykinin$_1$ receptor antagonists: the [des-Arg$^{10}$] derivative of D-Arg-(Hyp$^3$-Thi$^5$-D-Tic$^7$-Oic$^8$)-BK ("the [des-Arg$^{10}$] derivative of HOE 140", available from Hoechst Pharmaceuticals); and [Leu$^8$] des-Arg$^9$-BK. Suitable bradykinin$_2$ receptor antagonists include: [D-Phe$^7$]-BK; D-Arg-(Hyp$^3$-Thi$^{5,8}$-D-Phe$^7$)-BK ("NPC 349"); D-Arg-(Hyp$^3$-D-Phe$^7$)-BK ("NPC 567"); and D-Arg-(Hyp$^3$-Thi$^5$-D-Tic$^7$-Oic$^8$)-BK ("HOE 140"). These compounds are more fully described in the previously incorporated Perkins et al. 1993 and Dray et al. 1993 references. Suitable therapeutic and preferred concentrations are provided in Table 4.

TABLE 4

Therapeutic and Preferred Concentrations of Pain/Inflammation Inhibitory Agents

| Class of Agent | Therapeutic Concentrations (Nanomolar) | Preferred Concentrations (Nanomolar) |
|---|---|---|
| Bradykinin$_1$ Receptor Antagonists: | | |
| [Leu$^8$] des-Arg$^9$-BK | 1–1,000 | 50–500 |
| [des-Arg$^{10}$] derivative of HOE 140 | 1–1,000 | 50–500 |
| [leu$^9$] [des-Arg$^{10}$] kalliden | 0.1–500 | 10–200 |
| Bradykinin$_2$ Receptor Antagonists: | | |
| [D-Phe$^7$]-BK | 100–10,000 | 200–5,000 |
| NPC 349 | 1–1,000 | 50–500 |
| NPC 567 | 1–1,000 | 50–500 |
| HOE 140 | 1–1,000 | 50–500 |

E. Kallikrein Inhibitors

The peptide bradykinin is an important mediator of pain and inflammation, as noted previously. Bradykinin is produced as a cleavage product by the action of kallikrein on high molecular weight kininogens in plasma. Therefore, kallikrein inhibitors are believed to be therapeutic in inhibiting bradykinin production and resultant pain and inflammation. A suitable kallikrein inhibitor for use in the present invention is aprotinin. Suitable concentrations for use in the solutions of the present invention are set forth below in Table 5.

TABLE 5

Therapeutic and Preferred Concentrations of Pain/Inflammation Inhibitory Agents

| Class of Agent | Therapeutic Concentrations (Nanomolar) | Preferred Concentrations (Nanomolar) |
|---|---|---|
| Kallikrein Inhibitor: | | |
| Aprotinin | 0.1–1,000 | 50–500 |

F. Tachykinin Receptor Antagonists

Tachykinins (TKs) are a family of structurally related peptides that include substance P, neurokinin A (NKA) and neurokinin B (NKB). Neurons are the major source of TKs in the periphery. An important general effect of TKs is neuronal stimulation, but other effects include endothelium-dependent vasodilation, plasma protein extravasation, mast cell recruitment and degranulation and stimulation of inflammatory cells. Maggi, C. A., *Gen. Pharmacol.*, Vol. 22, pp. 1–24 (1991). Due to the above combination of physiological actions mediated by activation of TK receptors, targeting of TK receptors is a reasonable approach for the promotion of analgesia and the treatment of neurogenic inflammation.

1. Neurokinin$_1$ Receptor Subtype Antagonists

Substance P activates the neurokinin receptor subtype referred to as NK$_1$. Substance P is an undecapeptide that is present in sensory nerve terminals. Substance P is known to have multiple actions which produce inflammation and pain in the periphery after C-fiber activation, including vasodilation, plasma extravasation and degranulation of mast cells. Levine, J. D., et al., *Peptides and the Primary Afferent Nociceptor*, J. Neurosci. 13, p. 2273 (1993). A suitable Substance P antagonist is ([D-Pro$^9$[spiro-gamma-lactam]Leu$^{10}$,Trp$^{11}$]physalaemin-(1–11)) ("GR 82334"). Other suitable antagonists for use in the present invention which act on the NK$_1$ receptor are: 1-imino-2-(2-methoxyphenyl)-ethyl)-7,7-diphenyl-4-perhydroisoindolone (3aR, 7aR) ("RP 67580"); and 2S,3S-cis-3-(2-methoxybenzylamino)-2-benzhydrylquinuclidine ("CP 96,345"). Suitable concentrations for these agents are set forth in Table 6.

TABLE 6

Therapeutic and Preferred Concentrations of Pain/Inflammation Inhibitory Agents

| Class of Agent | Therapeutic Concentrations (Nanomolar) | Preferred Concentrations (Nanomolar) |
|---|---|---|
| Neurokinin$_1$ Receptor Subtype Antagonists | | |
| GR 82334 | 1–1,000 | 10–500 |
| CP 96,345 | 1–10,000 | 100–1,000 |
| RP 67580 | 0.1–1,000 | 100–1,000 |

2. Neurokinin$_2$ Receptor Subtype Antagonists

Neurokinin A is a peptide which is colocalized in sensory neurons with substance P and which also promotes inflammation and pain. Neurokinin A activates the specific neurokinin receptor referred to as NK$_2$. Edmonds-Alt, S., et al., *A Potent and Selective Non-Peptide Antagonist of the Neurokinin A (NK$_2$) Receptor*, Life Sci. 50:PL101 (1992). In the urinary tract, TKs are powerful spasmogens acting through only the NK$_2$ receptor in the human bladder, as well as the human urethra and ureter. Maggi, C. A., *Gen. Pharmacol.*, Vol. 22, pp. 1–24 (1991). Thus, the desired drugs for inclusion in a surgical solution for use in urological procedures would contain an antagonist to the NK$_2$ receptor to reduce spasm. Examples of suitable NK$_2$ antagonists include: ((S)-N-methyl-N-[4-(4-acetylamino-4-phenylpiperidino)-2-(3,4-dichlorophenyl) butyl]benzamide ("(±)-SR 48968"); Met-Asp-Trp-Phe-Dap-Leu ("MEN 10,627"); and cyc(Gln-Trp-Phe-Gly-Leu-Met) ("L 659,877"). Suitable concentrations of these agents are provided in Table 7.

TABLE 7

Therapeutic and Preferred Concentrations
of Pain/Inflammation Inhibitory Agents

| Class of Agent | Therapeutic Concentrations (Nanomolar) | Preferred Concentrations (Nanomolar) |
|---|---|---|
| Neurokinin$_2$ Receptor Subtype Antagonists: | | |
| MEN 10,627 | 1–1,000 | 10–1,000 |
| L 659,877 | 10–10,000 | 100–10,000 |
| (±)-SR 48968 | 10–10,000 | 100–10,000 |

G. CGRP Receptor Antagonists

Calcitonin gene-related peptide (CGRP) is a peptide which is also colocalized in sensory neurons with substance P, and which acts as a vasodilator and potentiates the actions of substance P. Brain, S. D., et al., *Inflammatory Oedema Induced by Synergism Between Calcitonin Gene-Related Peptide (CGRP) and Mediators of Increased Vascular Permeability*, Br. J. Pharmacol. 99, p. 202 (1985). An example of a suitable CGRP receptor antagonist is α-CGRP-(8–37), a truncated version of CGRP. This polypeptide inhibits the activation of CGRP receptors. Suitable concentrations for this agent are provided in Table 8.

TABLE 8

Therapeutic and Preferred Concentrations
of Pain/Inflammation Inhibitory Agents

| Class of Agent | Therapeutic Concentrations (Nanomolar) | Preferred Concentrations (Nanomolar) |
|---|---|---|
| CGRP Receptor Antagonist: | | |
| α-CGRP-(8-37) | 1–1,000 | 10–500 |

H. Interleukin Receptor Antagonist

Interleukins are a family of peptides, classified as cytokines, produced by leukocytes and other cells in response to inflammatory mediators. Interleukins (IL) may be potent hyperalgesic agents peripherally. Ferriera, S. H., et al., *Interleukin-1β as a Potent Hyperalgesic Agent Antagonized by a Tripeptide Analogue*, Nature 334, p. 698 (1988). An example of a suitable IL-1β receptor antagonist is Lys-D-Pro-Thr, which is a truncated version of IL-1 β. This tripeptide inhibits the activation of IL-1β receptors. Suitable concentrations for this agent are provided in Table 9.

TABLE 9

Therapeutic and Preferred Concentrations
of Pain/Inflammation Inhibitory Agents

| Class of Agent | Therapeutic Concentrations (Nanomolar) | Preferred Concentrations (Nanomolar) |
|---|---|---|
| Interleukin Receptor Antagonist: | | |
| Lys-D-Pro-Thr | 1–1,000 | 10–500 |

I. Inhibitors of Enzymes Active in the Synthetic Pathway for Arachidonic Acid Metabolites 1. Phospholipase Inhibitors The production of arachidonic acid by phospholipase A$_2$ (PLA$_2$) results in a cascade of reactions that produces numerous mediators of inflammation, known as eicosanoids. There are a number of stages throughout this pathway that can be inhibited, thereby decreasing the production of these inflammatory mediators. Examples of inhibition at these various stages are given below.

Inhibition of the enzyme PLA$_2$ isoform inhibits the release of arachidonic acid from cell membranes, and therefore inhibits the production of prostaglandins and leukotrienes resulting in decreased inflammation and pain. Glaser, K. B., *Regulation of Phospholipase A2 Enzymes: Selective Inhibitors and Their Pharmacological Potential*, Adv. Pharmacol. 32, p. 31 (1995). An example of a suitable PLA$_2$ isoform inhibitor is manoalide. Suitable concentrations for this agent are included in Table 10. Inhibition of the phospholipase C$_\gamma$(PLC$_{65}$) isoform also will result in decreased production of prostanoids and leukotrienes, and, therefore, will result in decreased pain and inflammation. An example of a PLCγ isoform inhibitor is 1-[6-((17β-3-methoxyestra-1,3,5(10)-trien-17-yl)amino)hexyl]-1H-pyrrole-2,5-dione.

TABLE 10

Therapeutic and Preferred Concentrations
of Pain/Inflammation Inhibitory Agents

| Class of Agent | Therapeutic Concentrations (Nanomolar) | Preferred Concentrations (Nanomolar) |
|---|---|---|
| PLA$_2$ Isoform Inhibitor: | | |
| manoalide | 100–100,000 | 500–10,000 |

2. Cyclooxygenase Inhibitors

Nonsteroidal anti-inflammatory drugs (NSAIDs) are widely used as anti-inflammatory, anti-pyretic, anti-thrombotic and analgesic agents. Lewis, R. A., *Prostaglandins and Leukotrienes*, In: Textbook of Rheumatology, 3d ed. (Kelley W. N., et al., eds.), p. 258 (1989). The molecular targets for these drugs are type I and type II cyclooxygenases (COX-1 and COX-2). These enzymes are also known as Prostaglandin H Synthase (PGHS)-1 (constitutive) and -2 (inducible), and catalyze the conversion of arachidonic acid to Prostaglandin H which is an intermediate in the biosynthesis of prostaglandins and thromboxanes. The COX-2 enzyme has been identified in endothelial cells, macrophages, and fibroblasts. This enzyme is induced by IL-1 and endotoxin, and its expression is upregulated at sites of inflammation. Constitutive activity of COX-1 and induced activity of COX-2 both lead to synthesis of prostaglandins which contribute to pain and inflammation.

NSAIDs currently on the market (diclofenac, naproxen, indomethacin, ibuprofen, etc.) are generally nonselective inhibitors of both isoforms of COX, but may show greater selectively for COX-1 over COX-2, although this ratio varies for the different compounds. Use of COX-1 and 2 inhibitors to block formation of prostaglandins represents a better therapeutic strategy than attempting to block interactions of the natural ligands with the seven described subtypes of prostanoid receptors. Reported antagonists of the eicosanoid receptors (EP-1, EP-2, EP-3) are quite rare and only specific, high affinity antagonists of the thromboxane A2 receptor have been reported. Wallace, J. and Cirino, G. *Trends in Pharm. Sci.*, Vol. 15 pp. 405–406 (1994).

The oral, intravenous or intramuscular use of cyclooxygenase inhibitors is contraindicated in patients with ulcer disease, gastritis or renal impairment. In the United States, the only available injectable form of this class of drugs is ketorolac (Toradol™), available from Syntex Pharmaceuticals, which is conventionally used intramuscularly or intravenously in postoperative patients but, again, is contraindicated for the above-mentioned categories of patients. The use of ketorolac, or any other cyclooxygenase inhibitor(s), in the solution in substantially lower dosages than currently used perioperatively may allow the use of this drug in otherwise contraindicated patients. The addition of a cyclooxygenase inhibitor to the solutions of the present invention adds a distinct mechanism for inhibiting the production of pain and inflammation during arthroscopy or other therapeutic or diagnostic procedures.

Preferred cyclooxygenase inhibitors for use in the present invention are ketorolac and indomethacin. Of these two agents, indomethacin is less preferred because of the relatively high dosages required. Therapeutic and preferred concentrations for use in the solution are provided in Table 11.

TABLE 11

Therapeutic and Preferred Concentrations of Pain/Inflammation Inhibitory Agents

| Class of Agent | Therapeutic Concentrations (Nanomolar) | Preferred Concentrations (Nanomolar) |
| --- | --- | --- |
| Cyclooxygenase Inhibitors: | | |
| ketorolac | 100–10,000 | 500–5,000 |
| indomethacin | 1,000–500,000 | 10,000–200,000 |

3. Lipooxygenase Inhibitors

Inhibition of the enzyme lipooxygenase inhibits the production of leukotrienes, such as leukotriene $B_4$, which is known to be an important mediator of inflammation and pain. Lewis, R. A., *Prostaglandins and Leukotrienes*, In: Textbook of Rheumatology, 3d ed. (Kelley W. N., et al., eds.), p. 258 (1989). An example of a 5-lipooxygenase antagonist is 2,3,5-trimethyl-6-(12-hydroxy-5,10-dodecadiynyl)-1,4-benzoquinone ("AA 861"), suitable concentrations for which are listed in Table 12.

TABLE 12

Therapeutic and Preferred Concentrations of Pain/Inflammation Inhibitory Agents

| Class of Agent | Therapeutic Concentrations (Nanomolar) | Preferred Concentrations (Nanomolar) |
| --- | --- | --- |
| Lipooxygenase Inhibitor: | | |
| AA 861 | 100–10,000 | 500–5,000 |

J. Prostanoid Receptor Antagonists

Specific prostanoids produced as metabolites of arachidonic acid mediate their inflammatory effects through activation of prostanoid receptors. Examples of classes of specific prostanoid antagonists are the eicosanoid EP-1 and EP-4 receptor subtype antagonists and the thromboxane receptor subtype antagonists. A suitable prostaglandin $E_2$ receptor antagonist is 8-chlorodibenz[b,f][1,4]oxazepine-10 (11H)-carboxylic acid, 2-acetylhydrazide ("SC 19220"). A suitable thromboxane receptor subtype antagonist is [15-[1α, 2β(5Z), 3β, 4α]-7-[3-[2-(phenylamino)-carbonyl] hydrazino] methyl]-7-oxobicyclo-[2,2,1]-hept-2-yl]-5-heptanoic acid ("SQ 29548"). Suitable concentrations for these agents are set forth in Table 13.

TABLE 13

Therapeutic and Preferred Concentrations of Pain/Inflammation Inhibitory Agents

| Class of Agent | Therapeutic Concentrations (Nanomolar) | Preferred Concentrations (Nanomolar) |
| --- | --- | --- |
| Eicosanoid EP-1 Antagonist: | | |
| SC 19220 | 100–10,000 | 500–5,000 |

K. Leukotriene Receptor Antagonists

The leukotrienes ($LTB_4$, $LTC_4$, and $LTD_4$) are products of the 5-lipooxygenase pathway of arachidonic acid metabolism that are generated enzymatically and have important biological properties. Leukotrienes are implicated in a number of pathological conditions including inflammation. Specific antagonists are currently being sought by many pharmaceutical companies for potential therapeutic intervention in these pathologies. Halushka, P. V., et al., Annu. Rev. Pharmacol. Toxicol. 29: 213–239 (1989); Ford-Hutchinson, A. Crit. Rev. Immunol. 10: 1–12 (1990). The $LTB_4$ receptor is found in certain immune cells including eosinophils and neutrophils. $LTB_4$ binding to these receptors results in chemotaxis and lysosomal enzyme release, thereby contributing to the process of inflammation. The signal transduction process associated with activation of the $LTB_4$ receptor involves G-protein-mediated stimulation of phosphotidylinositol (PI) metabolism and elevation of intracellular calcium (see FIG. 2).

An example of a suitable leukotriene $B_4$ receptor antagonist is SC (+)-(S)-7-(3-(2-(cyclopropylmethyl)-3-methoxy-4-[(methylamino)-carbonyl]phenoxy(propoxy)-3,4-dihydro-8-propyl-2H-1-benzopyran-2-propanoic acid ("SC 53228"). Concentrations for this agent that are suitable for the practice of the present invention are provided in Table 14. Other suitable leukotriene $B_4$ receptor antagonists include [3-[-2(7-chloro-2-quinolinyl)ethenyl]phenyl] [[3-(dimethylamino-3-oxopropyl)thio]methyl]thiopropanoic acid ("MK 0571") and the drugs LY 66,071 and ICI 20,3219. MK 0571 also acts as a $LTD_4$ receptor subtype antagonist.

TABLE 14

Therapeutic and Preferred Concentrations of Pain/Inflammation Inhibitory Agents

| Class of Agent | Therapeutic Concentrations (Nanomolar) | Preferred Concentrations (Nanomolar) |
| --- | --- | --- |
| Leukotriene $B_4$ Antagonist: | | |
| SC 53228 | 100–10,000 | 500–5,000 |

L. Opioid Receptor Agonists

Activation of opioid receptors results in anti-nociceptive effects and, therefore, agonists to these receptors are desirable. Opioid receptors include the $\mu$-, $\delta$- and $\kappa$-opioid receptor subtypes. The $\mu$-receptors are located on sensory neuron terminals in the periphery and activation of these receptors inhibits sensory neuron activity. Basbaum, A. I., et al., *Opiate analgesia: How Central is a Peripheral Target?*, N. Engl. J. Med., 325:1168 (1991). $\delta$- and $\kappa$-receptors are located on sympathetic efferent terminals and inhibit the release of prostaglandins, thereby inhibiting pain and inflammation. Taiwo, Y. O., et al., *Kappa-and Delta-Opioids Block Sympathetically Dependent Hyperalgesia*, J. Neurosci., Vol. 11, page 928 (1991). The opioid receptor subtypes are members of the G-protein coupled receptor superfamily. Therefore, all opioid receptor agonists interact and initiate signaling through their cognate G-protein coupled receptor (see FIGS. 3 and 7). Examples of suitable μ-opioid receptor agonists are fentanyl and Try-D-Ala-Gly-[N-MePhe]-NH(CH$_2$)—OH ("DAMGO"). An example of a suitable δ-opioid receptor agonist is [D-Pen$^2$,D-Pen$^5$] enkephalin ("DPDPE"). An example of a suitable κ-opioid receptor agonist is (trans)-3,4-dichloro-N-methyl-N-[2-(1-pyrrolidnyl)cyclohexyl]-benzene acetamide ("U50,488"). Suitable concentrations for each of these agents are set forth in Table 15.

TABLE 15

Therapeutic and Preferred Concentrations of Pain/Inflammation Inhibitory Agents

| Class of Agent | Therapeutic Concentrations (Nanomolar) | Preferred Concentrations (Nanomolar) |
|---|---|---|
| μ-Opioid Agonist: | | |
| DAMGO | 0.1–100 | 0.5–20 |
| sufentanyl | 0.01–50 | 1–20 |
| fentanyl | 0.1–500 | 10–200 |
| PL 017 | 0.05–50 | 0.25–10 |
| δ-Opioid Agonist: | | |
| DPDPE | 0.1–500 | 1.0–100 |
| κ-Opioid Agonist: | | |
| U50,488 | 0.1–500 | 1.0–100 |

M. Purinoceptor Antagonists and Agonists

Extracellular ATP acts as a signaling molecule through interactions with P$_2$ purinoceptors. One major class of purinoceptors are the P$_{2X}$ purinoceptors which are ligand-gated ion channels possessing intrinsic ion channels permeable to Na$^+$, K$^+$, and Ca$^{2+}$. P$_{2X}$ receptors described in sensory neurons are important for primary afferent neurotransmission and nociception. ATP is known to depolarize sensory neurons and plays a role in nociceptor activation since ATP released from damaged cells stimulates P$_{2X}$ receptors leading to depolarization of nociceptive nerve-fiber terminals. The P2X$_3$ receptor has a highly restricted distribution (Chen, C. C., et al., Nature, Vol. 377, pp. 428–431 (1995)) since it is selectively expressed in sensory C-fiber nerves that run into the spinal cord and many of these C-fibers are known to carry the receptors for painful stimuli. Thus, the highly restricted localization of expression for the P2X$_3$ receptor subunits makes these subtypes excellent targets for analgesic action (see FIGS. 3 and 7).

Suitable antagonists of P$_{2X}$/ATP purinoceptors for use in the present invention include, by way of example, suramin and pyridoxylphosphate-6-azophenyl-2,4-disulfonic acid ("PPADS"). Suitable concentrations for these agents are provided in Table 16.

Agonists of the P$_{2Y}$ receptor, a G-protein coupled receptor, are known to effect smooth muscle relaxation through elevation of inositol triphosphate (IP$_3$) levels with a subsequent increase in intracellular calcium. An example of a P$_{2Y}$ receptor agonist is 2-me-S-ATP.

TABLE 16

Therapeutic and Preferred Concentrations of Pain/Inflammation Inhibitory Agents

| Class of Agent | Therapeutic Concentrations (Nanomolar) | Preferred Concentrations (Nanomolar) |
|---|---|---|
| Purinoceptor Antagonists: | | |
| suramin | 100–100,000 | 10,000–100,000 |
| PPADS | 100–100,000 | 10,000–100,000 |

N. Adenosine Triphosphate (ATP)-Sensitive Potassium Channel Openers

ATP-sensitive potassium channels have been discovered in numerous tissues, including vascular and non-vascular smooth muscle and brain, and binding studies using radio-labeled ligands have confirmed their existence. Opening of these channels causes potassium (K$^+$) efflux and hyperpolarizes the cell membrane (see FIG. 2). This hyperpolarization induces a reduction in intracellular free calcium through inhibition of voltage-dependent calcium (Ca$^{2+}$) channels and receptor operated Ca$^{2+}$ channels. These combined actions drive the cell (e.g., smooth muscle cell) into a relaxed state or one which is more resistant to activation and, in the case of vascular smooth muscle, results in vasorelaxation. K$^+$ channel openers (KCOs) have been characterized as having potent antihypertensive activity in vivo and vasorelaxant activity in vitro (see FIG. 4). K$^+$ channel openers (KCOs) also have been shown to prevent stimulus coupled secretion and are considered to act on prejunctional neuronal receptors and thus will inhibit effects due to nerve stimulation and release of inflammatory mediators. Quast, U., et al., *Cellular Pharmacology of Potassium Channel Openers in Vascular Smooth Muscle*, Cardiovasc. Res., Vol. 28, pp. 805–810 (1994).

Synergistic interactions between endothelin (ET$_A$) antagonists and openers of ATP-sensitive potassium channels (KCOs) are expected in achieving vasorelaxation or smooth muscle relaxation. A rationale for dual use is based upon the fact that these drugs have different molecular mechanisms of action in promoting relaxation of smooth muscle and prevention of vasospasm. An initial intracellular calcium elevation in smooth muscle cells induced by the ET$_A$ receptor subsequently triggers activation of voltage-dependent channels and the entry of extracellular calcium which is required for contraction. Antagonists of the ET$_A$ receptor will specifically block this receptor mediated effect but not block increases in calcium triggered by activation of other G-protein coupled receptors on the muscle cell.

Potassium-channel opener drugs, such as pinacidil, will open these channels causing K$^+$ efflux and hyperpolarization of the cell membrane. This hyperpolarization will act to reduce contraction mediated by other receptors by the following mechanisms: (1) it will induce a reduction in intracellular free calcium through inhibition of voltage-dependent Ca$^{2+}$ channels by reducing the probability of opening L-type or T-type calcium channels, (2) it will restrain agonist induced (receptor operated channels) Ca$^{2+}$ release from intracellular sources through inhibition of inositol triphosphate (IP$_3$) formation, and (3) it will lower the efficiency of calcium as an activator of contractile proteins. Consequently, combined actions of these two classes of drugs will clamp the target cells into a relaxed state or one which is more resistant to activation.

Suitable ATP-sensitive K$^+$ channel openers for the practice of the present invention include: (−)pinacidil; cromakalim; nicorandil; minoxidil; N-cyano-N'-[1,1-dimethyl-[2,2,3,3-³H]propyl]-N"-(3-pyridinyl)guanidine ("P 1075"); and N-cyano-N'-(2-nitroxyethyl)-3-pyridinecarboximidamide monomethansulphonate ("KRN 2391"). Concentrations for these agents are set forth in Table 17.

TABLE 17

Therapeutic and Preferred Concentrations of Pain/Inflammation Inhibitory Agents

| Class of Agent | Therapeutic Concentrations (Nanomolar) | Preferred Concentrations (Nanomolar) |
|---|---|---|
| ATP-Sensitive K⁺ Channel Opener: | | |
| cromakalim | 10–10,000 | 100–10,000 |
| nicorandil | 10–10,000 | 100–10,000 |
| minoxidil | 10–10,000 | 100–10,000 |
| P 1075 | 0.1–1,000 | 10–1,000 |
| KRN 2391 | 1–10,000 | 100–1,000 |
| (–)pinacidil | 1–10,000 | 100–1,000 |

O. Anti-Spasm Agents

1. Multifunction Agents

Several of the anti-pain/anti-inflammatory agents described above also serve to inhibit vasoconstriction or smooth muscle spasm. As such, these agents also perform the function of anti-spasm agents, and thus are beneficially used in vascular and urologic applications. Anti-inflammatory/anti-pain agents that also serve as anti-spasm agents include: serotonin receptor antagonists, particularly, serotonin$_2$ antagonists; tachykinin receptor antagonists and ATP-sensitive potassium channel openers.

2. Nitric Oxide Donors

Nitric oxide donors may be included in the solutions of the present invention particularly for their anti-spasm activity. Nitric oxide (NO) plays a critical role as a molecular mediator of many physiological processes, including vasodilation and regulation of normal vascular tone. Within endothelial cells, an enzyme known as NO synthase (NOS) catalyzes the conversion of L-arginine to NO which acts as a diffusible second messenger and mediates responses in adjacent smooth muscle cells (see FIG. 8). NO is continuously formed and released by the vascular endothelium under basal conditions which inhibits contractions and controls basal coronary tone and is produced in the endothelium in response to various agonists (such as acetylcholine) and other endothelium dependent vasodilators. Thus, regulation of NO synthase activity and the resultant levels of NO are key molecular targets controlling vascular tone (see FIG. 8). Muramatsu, K., et, al., Coron. Artery Dis., Vol. 5, pp. 815–820 (1994).

Synergistic interactions between NO donors and openers of ATP-sensitive potassium channels (KCOS) are expected to achieve vasorelaxation or smooth muscle relaxation. A rationale for dual use is based upon the fact that these drugs have different molecular mechanisms of action in promoting relaxation of smooth muscle and prevention of vasospasm. There is evidence from cultured coronary arterial smooth muscle cells that the vasoconstrictors: vasopressin, angotensin II and endothelin, all inhibit $K_{ATP}$ currents through inhibition of protein kinase A. In addition, it has been reported that $K_{ATP}$ current in bladder smooth muscle is inhibited by muscarinic agonists. The actions of NO in mediating smooth muscle relaxation occur via independent molecular pathways (described above) involving protein kinase G (see FIG. 8). This suggests that the combination of the two classes of agents will be more efficacious in relaxing smooth muscle than employing a single class of agent alone.

Suitable nitric oxide donors for the practice of the present invention include nitroglycerin, sodium nitroprusside, the drug FK 409, FR 144420, 3-morpholinosydnonimine, or linsidomine chlorohydrate, ("SIN-1"); and S-nitroso-N-acetylpenicillamine ("SNAP"). Concentrations for these agents are set forth in Table 18.

TABLE 18

Therapeutic and Preferred Concentrations of Spasm Inhibitory Agents

| Class of Agent | Therapeutic Concentrations (Nanomolar) | Preferred Concentrations (Nanomolar) |
|---|---|---|
| Nitric Oxide Donors: | | |
| Nitroglycerin | 10–10,000 | 100–1,000 |
| sodium nitroprusside | 10–10,000 | 100–1,000 |
| SIN-1 | 10–10,000 | 100–1,000 |
| SNAP | 10–10,000 | 100–1,000 |
| FK 409 (NOR-3) | 1–1,000 | 10–500 |
| FR 144420 (NOR-4) | 10–10,000 | 100–5,000 |

3. Endothelin Receptor Antagonists

Endothelin is a 21 amino acid peptide that is one of the most potent vasoconstrictors known. Three different human endothelin peptides, designated ET-1, ET-2 and ET-3 have been described which mediate their physiological effects through at least two receptor subtypes referred to as $ET_A$ and $ET_B$ receptors. The heart and vascular smooth muscle contain predominantly $ET_A$ receptors and this subtype is responsible for contraction in these tissues. Furthermore, $ET_A$ receptors have often been found to mediate contractile responses in isolated smooth muscle preparations. Antagonists of $ET_A$ receptors have been found to be potent antagonists of human coronary artery contractions. Thus, antagonists to the $ET_A$ receptor should be therapeutically beneficial in the perioperative inhibition of coronary vasospasm and may additionally be useful in inhibition of smooth muscle contraction in urological applications. Miller, R. C., et al., Trends in Pharmacol. Sci., Vol. 14, pp. 54–60 (1993).

Suitable endothelin receptor antagonists include: cyclo (D-Asp-Pro-D-Val-Leu-D-Trp) ("BQ 123"); (N,N-hexamethylene)-carbamoyl-Leu-D-Trp-(CHO)-D-Trp-OH ("BQ 610"); (R)2-([R-2-[(s)-2-([1-hexahydro-1H-azepinyl]-carbonyl]amino-4-methyl-pentanoyl) amino-3-(3-[1-methyl-1H-indodyl])propionylamino-3 (2-pyridyl) propionic acid ("FR 139317"); cyclo(D-Asp-Pro-D-Ile-Leu-D-Trp) ("JKC 301"); cyclo(D-Ser-Pro-D-Val-Leu-D-Trp) ("JK 302"); 5-(dimethylamino)-N-(3,4-dimethyl-5-isoxazolyl)-1-naphthalenesulphonamide ("BMS 182874"); and N-[1-Formyl-N-[N-[(hexahydro-1H-azepin-1-yl)carbonyl]-L-leucyl]-D-tryptophyl]-D-tryptophan ("BQ 610"). Concentrations for a representative three of these agents are set forth in Table 19.

TABLE 19

Therapeutic and Preferred Concentrations of Spasm Inhibitory Agents

| Class of Agent | Therapeutic Concentrations (Nanomolar) | Preferred Concentrations (Nanomolar) |
| --- | --- | --- |
| Endothelin Receptor Antagonists: | | |
| BQ 123 | 0.01–1,000 | 10–1,000 |
| FR 139317 | 1–100,000 | 100–10,000 |
| BQ 610 | 0.01 to 10,000 | 10–1,000 |

4. $Ca^{2+}$ Channel Antagonists

Calcium channel antagonists are a distinct group of drugs that interfere with the transmembrane flux of calcium ions required for activation of cellular responses mediating neuroinflammation. Calcium entry into platelets and white blood cells is a key event mediating activation of responses in these cells. Furthermore, the role of bradykinin receptors and neurokinin receptors ($NK_1$ and $NK_2$) in mediating the neuroinflammation signal transduction pathway includes increases in intracellular calcium, thus leading to activation of calcium channels on the plasma membrane. In many tissues, calcium channel antagonists, such as nifedipine, can reduce the release of arachidonic acid, prostaglandins, and leukotrienes that are evoked by various stimuli. Moncada, S., Flower, R. and Vane, J. in *Goodman's and Gilman's Pharmacological Basis of Therapeutics*, (7th ed.), MacMillan Publ. Inc., pp. 660–5 (1995).

Calcium channel antagonists also interfere with the transmembrane flux of calcium ions required by vascular smooth muscle for contractions. This effect provides the rationale for the use of calcium channel antagonists perioperatively during procedures in which the goal is to alleviate vasospasm and promote relaxation of smooth muscle. The dihydropyridines, including nisoldipine, act as specific inhibitors (antagonists) of the voltage-dependent gating of the L-type subtype of calcium channels. Systemic administration of the calcium channel antagonist nifedipine during cardiac surgery previously has been utilized to prevent or minimize coronary artery vasospasm. Seitelberger, R., et al., Circulation, Vol. 83, pp.460–468 (1991).

Calcium channel antagonists, which are among the antispasm agents useful in the present invention, exhibit synergistic effect when combined with other agents of the present invention. Calcium ($Ca^{2+}$) channel antagonists and nitric oxide (NO) donors interact in achieving vasorelaxation or smooth muscle relaxation, i.e., in inhibiting spasm activity. A rationale for dual use is based upon the fact that these two classes of drugs have different molecular mechanisms of action, may not be completely effective in achieving relaxation used alone, and may have different time periods of effectiveness. In fact, there are numerous studies showing that calcium channel antagonists alone cannot achieve complete relaxation of vascular muscle that has been precontracted with a receptor agonist.

The effect of nisoldipine, used alone and in combination with nitroglycerin, on spasm of the internal mammary artery (IMA) showed that the combination of the two drugs produced a large positive synergistic effect in the prevention of contraction (Liu et al., 1994). These studies provide a scientific basis for combination of a calcium channel antagonist and nitric oxide (NO) donor for the efficacious prevention of vasospasm and relaxation of smooth muscle. Examples of systemic administration of nitroglycerin and nifedipine during cardiac surgery to prevent and treat myocardial ischemia or coronary artery vasospasm have been reported (Cohen et al., 1983; Seitelberger et al., 1991).

Calcium channel antagonists also exhibit synergistic effect with endothelin receptor subtype A ($ET_A$) antagonists. Yanagisawa and coworkers observed that dihydropyridine antagonists blocked effects of ET-1, an endogenous agonist at the $ET_A$ receptor in coronary arterial smooth muscle, and hence speculated that ET-1 is an endogenous agonist of voltage-sensitive calcium channels. It has been found that the sustained phase of intracellular calcium elevation in smooth muscle cells induced by $ET_A$ receptor activation requires extracellular calcium and is at least partially blocked by nicardipine. Thus, the inclusion of a calcium channel antagonist would be expected to synergistically enhance the actions of an $ET_A$ antagonist when combined in a surgical solution.

Calcium channel antagonists and ATP-sensitive potassium channel openers likewise exhibit synergistic action. Potassium channels that are ATP-sensitive ($K_{ATP}$) couple the membrane potential of a cell to the cell's metabolic state via sensitivity to adenosine nucleotides. KATP channels are inhibited by intracellular ATP but are stimulated by intracellular nucleotide diphosphates. The activity of these channels is controlled by the electrochemical driving force to potassium and intracellular signals (e.g., ATP or a G-protein), but are not gated by the membrane potential per se. $K_{ATP}$ channels hyperpolarize the membrane and thus allow them to control the resting potential of the cell. ATP-sensitive potassium currents have been discovered in skeletal muscle, brain, and vascular and nonvascular smooth muscle. Binding studies with radiolabeled ligands have confirmed the existence of ATP-sensitive potassium channels which are the receptor targets for the potassium-channel opener drugs such as pinacidil. Opening of these channels causes potassium efflux and hyperpolarizes the cell membrane. This hyperpolarization (1) induces a reduction in intracellular free calcium through inhibition of voltage-dependent $Ca^{2+}$ channels by reducing the probability of opening L-type or T-type calcium channels, (2) restrains agonist induced (at receptor operated channels) $Ca^{2+}$ release from intracellular sources through inhibition of inositol triphosphate ($IP_3$) formation, and (3) lowers the efficiency of calcium as an activator of contractile proteins. The combined actions of these two classes of drugs (ATP-sensitive potassium channel openers and calcium channel antagonists) will clamp the target cells into a relaxed state or one which is more resistant to activation.

Finally, calcium channel antagonists and tachykinin and bradykinin antagonists exhibit synergistic effects in mediating neuroinflammation. The role of neurokinin receptors in mediating neuroinflammation has been established. The $neurokinin_1$($NK_1$) and $neurokinin_2$ ($NK_2$) receptor (members of the G-protein coupled superfamily) signal transduction pathway includes increases in intracellular calcium, thus leading to activation of calcium channels on the plasma membrane. Similarly, activation of $bradykinin_2$ ($BK_2$) receptors is coupled to increases in intracellular calcium. Thus, calcium channel antagonists interfere with a common mechanism involving elevation of intracellular calcium, part of which enters through L-type channels. This is the basis for synergistic interaction between calcium channel antagonists and antagonists to neurokinin and $bradykinin_2$ receptors.

Suitable calcium channel antagonists for the practice of the present invention include nisoldipine, nifedipine, nimodipine, lacidipine, isradipine and amlodipine. Suitable concentrations for these agents are set forth in Table 20.

TABLE 20

Therapeutic and Preferred Concentrations of Spasm Inhibitory Agents

| Class of Agent | Therapeutic Concentrations (Nanomolar) | Preferred Concentrations (Nanomolar) |
| --- | --- | --- |
| Calcium Channel Antagonists: | | |
| nisoldipine | 1–10,000 | 100–1,000 |
| nifedipine | 1–10,000 | 100–5,000 |
| nimodipine | 1–10,000 | 100–5,000 |
| lacidipine | 1–10,000 | 100–5,000 |
| isradipine | 1–10,000 | 100–5,000 |
| amlodipine | 1–10,000 | 100–5,000 |

P. Anti-Restenosis Agents

Solutions of the present invention utilized for cardiovascular and general vascular procedures may optionally also include an anti-restenosis agent, particularly for angioplasty, rotational atherectomy and other interventional vascular uses. The following drugs are suitable for inclusion in the previously described cardiovascular and general vascular irrigation solutions when limitation of restenosis is indicated. The following anti-restenosis agents would preferably be combined with anti-spasm, and still more preferably also with anti-pain/anti-inflammation agents, in the solutions of the present invention.

1. Antiplatelet Agents

At sites of arterial injury, platelets adhere to collagen and fibrinogen via specific cell surface receptors, and are then activated by several independent mediators. A variety of agonists are able to activate platelets, including collagen, ADP, thromboxane A2, epinephrine and thrombin. Collagen and thrombin serve as primary activators at sites of vascular injury, while ADP and thromboxane A2 act to recruit additional platelets into a growing platelet plug. The activated platelets degranulate and release other agents which serve as chemoattractants and vasoconstrictors, thus promoting vasospasm and platelet accumulation. Thus, antiplatelet agents can be antagonists drawn from any of the above agonist-receptor targets.

Since platelets play such an important role in the coagulation cascade, oral antiplatelet agents have been routinely administered to patients undergoing vascular procedures. Indeed, because of this multiplicity of activators and observations that single antiplatelet agents are not effective, some investigators have concluded that a combined treatment protocol is necessary for effectiveness. Recently, Willerson and coworkers reported the intravenous use of 3 combined agents, ridogrel (an antagonist of thromboxane A2), ketanserin (a serotonin antagonist) and clopidogrel (an ADP antagonist). They found that the combination of 3 antagonists inhibited several relevant platelet functions and reduced neointimal proliferation in a canine coronary angioplasty model (JACC Abstracts, Feb. 1995). It is still uncertain which approach to treatment of coronary thrombosis will be most successful. One possibility would be to include an antiplatelet agent and an antithrombotic agent in the cardiovascular and general vascular solutions of the present invention.

a. Thrombin Inhibitors and Receptor Antagonists

Thrombin plays a central role in vascular lesion formation and is considered the principal mediator of thrombogenesis. Thus, thrombus formation at vascular lesion sites during and after PTCA (percutaneous transluminal coronary angioplasty) or other vascular procedure is central to acute reocclusion and chronic restenosis. This process can be interrupted by application of direct anti-thrombins, including hirudin and its synthetic peptide analogs, as well as thrombin receptor antagonist peptides (Harker, et al., 1995, Am. J. Cardiol 75, 12B). Thrombin is also a potent growth factor which initiates smooth muscle cell proliferation at sites of vascular injury. In addition, thrombin also plays a role in modulating the effects of other growth factors such as PDGF (platelet-derived growth factor), and it has been shown that thrombin inhibitors reduce expression of PDGF mRNA subsequent to vascular injury induced by balloon angioplasty.

Hirudin is the prototypic direct antithrombin drug since it binds to the catalytic site and the substrate recognition site (exosite) of thrombin. Animal studies using baboons have shown that this proliferative response can be reduced 80% using recombinant hirudin (Ciba-Geigy). Hirulog (Biogen) is a dodecapeptide modeled after hirudin, and binds to the active site of thrombin via a Phe-Pro-Arg linker molecule. Large clinical trials of hirudin and hirulog are underway to test their efficacy in reducing vascular lesions after PTCA and Phase II data on these inhibitors to date is positive, and both drugs are believed to be suitable in the solutions of the present invention. Preliminary results of a 1,200 patient trial with repeat angiographic assessment at 6 months to detect restenosis indicated superior short-term suppression of ischemic events with hirudin vs. heparin. An advantage of this approach is that no significant bleeding complications were reported. A sustained-release local hirulog therapy was found to decrease early thrombosis but not neointimal thickening after arterial stenting in pigs. Muller, D. et al., *Sustained-Release Local Hirulog Therapy Decreases Early Thrombosis but not Neointimal Thickening After Arterial Stenting*, Am. Heart J. 133, No. 2, pp. 211–218, (1996). In this study, hirulog was released from an impregnated polymer placed around the artery.

Other active anti-thrombin agents being tested which are theorized to be suitable for the present invention are argatroban (Texas Biotechnology) and efegatran (Lilly).

TABLE 21

Therapeutic and Preferred Concentrations of Restenosis Inhibitory Agents

| Class of Agent | Therapeutic/Preferred Concentrations (Nanomolar) | More preferred (Nanomolar) |
| --- | --- | --- |
| Thrombin Inhibitors and Receptor Angtagonists: | | |
| hirudin | 0.00003–3/0.0003–0.3 | 0.03 |
| hirulog | 0.2–20,000/2–2,000 | 200 | b. ADP Receptor Antagonists (Purinoceptor Antagonists)

Ticlopidine, an analog of ADP, inhibits both thromboxane and ADP-induced platelet aggregation. It is likely that ticlopidine blocks interaction of ADP with its receptor, thereby inhibiting signal transduction by this G-protein coupled receptor on the surface of platelet membranes. A preliminary study showed it to be more effective than aspirin in combination with dipyridamole. However, the clinical use of ticlopidine has been limited because it causes neutropenia. Clopidogrel, a ticlopidine analog, is thought to have fewer adverse side effects than ticlopidine and is currently being studied for prevention of ischemic events. It is theorized that these agents may be suitable for use in the solutions of the present invention.

c. Thromboxane Inhibitors and Receptor Antagonists

Agents currently utilized for conventional methods of treatment of thrombosis rely upon aspirin, heparin and plasminogen activators. Aspirin irreversibly acetylates cyclooxygenase and inhibits the synthesis of thromboxane A2 and prostacyclin. While data support a benefit of aspirin for PTCA, the underlying efficacy of aspirin is considered as only partial or modest. This is likely due to platelet activation through thromboxane A2 independent pathways that are not blocked by aspirin induced acetylation of cyclooxygenase. Platelet aggregation and thrombosis may occur despite aspirin treatment. Aspirin in combination with dipyridamole has also been shown to reduce the incidence of acute complication during PTCA but not the incidence of restenosis.

Two thromboxane receptor antagonists appear to be more efficacious than aspirin and are believed suitable for use in the solutions and methods of the present invention. Ticlopidine inhibits both thromboxane and ADP-induced platelet aggregation. Ridogrel (R68060) is a combined thromboxane B2 synthetase inhibitor and thromboxane-prostaglandin endoperoxide receptor blocker. It has been compared with salicylate therapy in an open-pilot study of patients undergoing PTCA administered in combination with heparin. Timmermans, C., et al., Ridogrel in the Setting of Percutaneous Transluminal Coronary Angioplasty, Am. J. Cardiol. 68, pp. 463–466, (1991). Treatment consisted of administering a slow intravenous injection of 300 mg just prior to the start of the PTCA procedure and continued orally after 12 hrs with a dose of 300 mg/twice daily. From this study, ridogrel was found to be primarily successful since no early acute reocclusion occurred in 30 patients. Bleeding complications did occur in a significant number (34%) of patients, and this appears to be a complicating factor that would require special care. The study confirmed that ridogrel is a potent long-lasting inhibitor of thromboxane B2 synthetase.

2. Inhibitors of Cell Adhesion Molecules a. Selectin Inhibitors

Selectin inhibitors block the interaction of a selectin with its cognate ligand or receptor. Representative examples of selectin targets at which these inhibitors would act include, but are not limited to, E-selectin and P-selectin receptors. Upjohn Co. has licensed rights to a monoclonal antibody developed by Cytel Corps that inhibits the activity of P-selectin. The product, CY 1748, is in preclinical development, with a potential indication being restenosis.

b. Integrin Inhibitors

The platelet glycoprotein IIb/IIIa complex is present on the surface of resting as well as activated platelets. It appears to undergo a transformation during platelet activation which enables it to serve as a binding site for fibrinogen and other adhesive proteins. Most promising new antiplatelet agents are directed at this integrin cell surface receptor which represents a final common pathway for platelet aggregation. Several types of agents fit into the class of GPIIb/IIIa integrin antagonists. A monoclonal antibody, c7E3, (CentoRx; Centocor, Malvern, Pa.) has been intensively studied to date in a 3,000 patient PTCA study. It is a chimeric human/murine hybrid. A 0.25 mg/kg bolus of c7E3 followed by 10 µg/min intravenous infusion for 12 hrs produced greater than 80% blockade of GPIIb/IIIa receptors for the duration of the infusion. This was correlated with a greater than 80% inhibition of platelet aggregation. The antibody was coadministered with heparin and an increased risk of bleeding was noted. Additional information was obtained from the EPIC trial which showed a significant reduction in the primary end point, a composite of death rate, incidence of nonfatal myocardial infarction and need for coronary revascularization, and suggested a long term benefit. Tcheng, (1995) Am. Heart J. 130, 673–679. A phase IV study (EPILOG) designed to address safety and efficacy issues with c7E3 Fab is planned or in progress. This monoclonal antibody can also be classified as a platelet membrane glycoprotein receptor antagonist directed against the glycoprotein IIb/IIIa receptor.

The platelet glycoprotein IIb/IIIa receptor blocker, integrelin, is a cyclic heptapeptide that is highly specific for this molecular target. In contrast to the antibody, it has a short biologic half-life (about 10 minutes). The safety and efficacy of integrelin was first evaluated in the Phase II Impact trial. Either 4 or 12 hour intravenous infusions of 1.0 µg/kg/min of integrelin were utilized (Topol, E., 1995 Am. J. Cardiol, 27B-33B). It was provided in combination with other agents (heparin, aspirin) and was shown to exhibit potent antiplatelet aggregation properties (>80%). A phase III study, the IMPACT II trial, of 4000 patients showed that integrelin markedly reduced ischemic events in patients who had undergone Rotablator atherectomy (JACC Abstracts, 1996). Suitable concentrations of the drugs c7E3 and integrelin for use in the present invention are set forth below.

In addition, two peptidomimetics, MK-383 (Merck) and RO 4483 (Hoffmann-LaRoche), have been studied in Phase II clinicals. Since these are both small molecules, they have a short half-life and high potency. However, these seem to also have less specificity, interacting with other closely related integrins. It is theorized that these peptidomimetics may also be suitable for use in the present invention.

TABLE 22

Therapeutic and Preferred Concentrations of Restenosis Inhibitory Agents

| Class of Agent | Therapeutic/Preferred Concentrations (Nanomolar) | More preferred (Nanomolar) |
| --- | --- | --- |
| Cell Adhesion Inhibitors: | | |
| c7E3 | 0.5–50,000/5–5,000 | 500 |
| Integrelin | 0.1–10,000/1–1000 × $K_d$ | 100 × $K_d$ |

3. Anti-chemotactic Agents

Anti-chemotactic agents prevent the chemotaxis of inflammatory cells. Representative examples of anti-chemotactic targets at which these agents would act include, but are not limited to, F-Met-Leu-Phe receptors, IL-8 receptors, MCP-1 receptors, and MIP-1-α/RANTES receptors. Drugs within this class of agents are early in the development stage, but it is theorized that they may be suitable for use in the present invention.

4. Interleukin Receptor Antagonists

Interleukin receptor antagonists are agents which block the interaction of an interleukin with its cognate ligand or receptor. Specific receptor antagonists for any of the numerous interleukin receptors are early in the development process. The exception to this is the naturally occurring existence of a secreted form of the IL-1 receptor, referred to as IL-1 antagonist protein (IL-1AP). This antagonist binds IL-1 and has been shown to suppress the biological actions of IL-1, and is theorized to be suitable for the practice of the present invention.

5. Intracellular Signaling Inhibitors a. Protein Kinase Inhibitors i. Protein Kinase C (PKC) Inhibitors

Protein kinase C (PKC) plays a crucial role in cell-surface signal transduction for a number of physiological processes. PKC isozymes can be activated as downstream targets resulting from initial activation of either G-protein coupled receptors (e.g., serotonin, endothelin, etc.) or growth-factor receptors such as PDGF. Both of these receptor classes play important roles in mediating vascular spasm and restenosis subsequent to coronary balloon angioplasty procedures.

Molecular cloning analysis has revealed that PKC exists as a large family consisting of at least 8 subspecies (isozymes). These isozymes differ substantially in structure and mechanism for linking receptor activation to changes in the proliferative response of specific cells. Expression of specific isozymes is found in a wide variety of cell types, including platelets, neutrophils, myeloid cells, and smooth muscle cells. Inhibitors of PKC are therefore likely to effect signaling pathways in several cell types unless the inhibitor shows isozyme specificity. Thus, inhibitors of PKC can be predicted to be effective in blocking the proliferative response of smooth muscle cells and may also have an anti-inflammatory effect in blocking neutrophil activation and subsequent attachment. Several inhibitors have been described and initial reports indicate an $IC_{50}$ of 50 nM for calphostin C inhibitory activity. G-6203 (also known as Go 6976) is a new, potent PKC inhibitor with high selectivity for certain PKC isotypes with $IC_{50}$ values in the 2–10 nM range. Concentrations of these and another drug, GF 109203X, also known as Go 6850 or bisindoylmaleimide I (available from Warner-Lambert), that are believed to be suitable for use in the present invention are set forth below.

TABLE 23

Therapeutic and Preferred Concentrations of Restenosis Inhibitory Agents

| Class of Agent | Therapeutic/Preferred Concentrations (Nanomolar) | More preferred (Nanomolar) |
|---|---|---|
| Protein Kinase C Inhibitors | | |
| calphostin C | 0.5–50,000/100–5,000 | 500 |
| GF 109203X | 0.1–10,000/1–1,000 | 100 |
| G-6203 (Go 6976) | 0.1–10,000/1–1,000 | 100 | ii. Protein Tyrosine Kinase Inhibitors

Although there is a tremendous diversity among the numerous members of the receptors tyrosine-kinase (RTK) family, the signaling mechanisms used by these receptors share many common features. Biochemical and molecular genetic studies have shown that binding of the ligand to the extracellular domain of the RTK rapidly activates the intrinsic tyrosine kinase catalytic activity of the intracellular domain (see FIG. 5). The increased activity results in tyrosine-specific phosphorylation of a number of intracellular substrates which contain a common sequence motif. Consequently, this causes activation of numerous "downstream" signaling molecules and a cascade of intracellular pathways that regulate phospholipid metabolism, arachidonate metabolism, protein phosphorylation (involving mechanisms other than protein kinases), calcium mobilization and transcriptional activation (see FIG. 2). Growth-factor-dependent tyrosine kinase activity of the RTK cytoplasmic domain is the primary mechanism for generation of intracellular signals that lead to cellular proliferation. Thus, inhibitors have the potential to block this signaling and thereby prevent the proliferative response (see FIG. 5).

The platelet-derived growth factor (PDGF) receptor is of great interest as a target for inhibition in the cardiovascular field since it is believed to play a significant role both in atherosclerosis and restenosis. The release of PDGF by platelets at damaged surfaces of endothelium within blood vessels results in stimulation of PDGF receptors on vascular smooth muscle cells. As described above, this initiates a sequence of intracellular events leading to enhanced proliferation and neointimal thickening. An inhibitor of PDGF kinase activity would be expected to prevent proliferation and enhance the probability of success following cardiovascular and general vascular procedures. Any of several related tyrphostin compounds have potential as specific inhibitors of PDGF-receptor tyrosine kinase activity ($IC_{50}$s in vitro in the 0.5–1.0 μM range), since they have little effect on other protein kinases and other signal transduction systems. To date, only a few of the many tyrphostin compounds are commercially available, and suitable concentrations for these agents as used in the present invention are set forth below. In addition, staurosporine has been reported to demonstrate potent inhibitory effects against several protein tyrosine kinases of the src subfamily and a suitable concentration for this agent as used in the present invention also is set forth below.

TABLE 24

Therapeutic and Preferred Concentrations of Restenosis Inhibitory Agents

| Class of Agent | Therapeutic/Preferred Concentrations (Nanomolar) | More preferred (Nanomolar) |
|---|---|---|
| Protein Kinase Inhibitors | | |
| lavendustin A | 10–100,000/100–10,000 | 10,000 |
| tyrphostin AG1296 | 10–100,000/100–20,000 | 10,000 |
| tyrphostin AG1295 | 10–100,000/100–20,000 | 10,000 |
| staurosporine | 1–100,000/10–10,000 | 1,000 | b. Modulators of Intracellular Protein Tyrosine Phosphatases.

Non-transmembrane protein tyrosine phosphatases (PTPases) containing src-homology$_2$ SH2 domains are known and nomenclature refers to them as SH-PTP1 and SH-PTP2. In addition, SH-PTP1 is also known as PTP1C, HCP or SHP. SH-PTP2 is also known as PTP1D or PTP2C. Similarly, SH-PTP1 is expressed at high levels in hematopoietic cells of all lineages and all stages of differentiation, and the SH-PTP1 gene has been identified as responsible for the motheaten (me) mouse phenotype and this provides a basis for predicting the effects of inhibitors that would block its interaction with its cellular substrates. Stimulation of neutrophils with chemotactic peptides is known to result in the activation of tyrosine kinases that mediate neutrophil responses (Cui, et al., 1994 J. Immunol.) and PTPase activity modulates agonist induced activity by reversing the effects of tyrosine kinases activated in the initial phases of cell stimulation. Agents that could stimulate PTPase activity could have potential therapeutic applications as anti-inflammatory mediators.

These same PTPases have also been shown to modulate the activity of certain RTKs. They appear to counter-balance the effect of activated receptor kinases and thus may represent important drug targets. In vitro experiments show that injection of PTPase blocks insulin stimulated phosphorylation of tyrosyl residues on endogenous proteins. Thus, activators of PTPase activity could serve to reverse activation of PDGF-receptor action in restenosis, and are believed to be useful in the solutions of the present invention. In addition, receptor-linked PTPases also function as extracellular ligands, similar to those of cell adhesion molecules. The functional consequences of the binding of a ligand to the extracellular domain have not yet been defined, but it is reasonable to assume that binding would serve to modulate phosphatase activity within cells (Fashena and Zinn, 1995, Current Biology, 5, 1367–1369). Such actions could block adhesion mediated by other cell surface adhesion molecules (NCAM) and provide an anti-inflammatory effect. No drugs have been developed yet for these applications.

c. Inhibitors of SH2 Domains (src Homology$_2$ Domains).

SH2 domains, originally identified in the src subfamily of protein tyrosine kinases (PTKs), are noncatalytic protein sequences and consist of about 100 amino acids conserved among a variety of signal transducing proteins (Cohen, et al., 1995). SH2 domains function as phosphotyrosine-binding modules and thereby mediate critical protein—protein associations in signal transduction pathways within cells (Pawson, Nature, 573–580, 1995). In particular, the role of SH2 domains has been clearly defined as critical for receptor tyrosine kinase (RTK) mediated signaling such as in the case of the platelet-derived growth factor (PDGF) receptor. Phosphotyrosine-containing sites on autophosphorylated RTKs serve as binding sites for SH2-proteins and thereby mediate the activation of biochemical signaling pathways (see FIG. 2) (Carpenter, G., FASEB J. 6:3283–3289, 1992; Sierke, S. and Koland, J. Biochem. 32:10102–10108, 1993). The SH2 domains are responsible for coupling the activated growth-factor receptors to cellular responses which include alterations in gene expression, and ultimately cellular proliferation (see FIG. 5). Thus, inhibitors that will selectively block the effects of activation of specific RTKs expressed on the surface of vascular smooth muscle cells are predicted to be effective in blocking proliferation and the restenosis process after PTCA or other vascular procedure. One RTK target of current interest is the PDGF receptor.

At least 20 cytosolic proteins have been identified that contain SH2 domains and function in intracellular signaling. The distribution of SH2 domains is not restricted to a particular protein family, but found in several classes of proteins, protein kinases, lipid kinases, protein phosphatases, phospholipases, Ras-controlling proteins and some transcription factors. Many of the SH2-containing proteins have known enzymatic activities while others (Grb2 and Crk) function as "linkers" and "adapters" between cell surface receptors and "downstream" effector molecules (Marengere, L., et al., Nature 369:502–505, 1994).

Examples of proteins containing SH2 domains with enzymatic activities that are activated in signal transduction include, but are not limited to, the src subfamily of protein tyrosine kinases (src (pp60$^{c\text{-}src}$), abl, lck, fyn, fgr and others), phospholipaseCγ (PLCγ), phosphatidylinositol 3-kinase (PI-3-kinase), p21-ras GTPase activating protein (GAP) and SH2 containing protein tyrosine phosphatases (SH-PTPases) (Songyang, et al., Cell 72, 767–778, 1993). Due to the central role these various SH2-proteins occupy in transmitting signals from activated cell surface receptors into a cascade of additional molecular interactions that ultimately define cellular responses, inhibitors which block specific SH2 protein binding are desirable as agents for a variety of potential therapeutic applications.

In addition, the regulation of many immune/inflammatory responses is mediated through receptors that transmit signals through non-receptor tyrosine kinases containing SH2 domains. T-cell activation via the antigen specific T-cell receptor (TCR) initiates a signal transduction cascade leading to lymphokine secretion and T-cell proliferation. One of the earliest biochemical responses following TCR activation is an increase in tyrosine kinase activity. In particular, neutrophil activation is in part controlled through responses of the cell surface immunoglobulin G receptors. Activation of these receptors mediates activation of unidentified tyrosine kinases which are known to possess SH2 domains. Additional evidence indicates that several src-family kinases (lck, blk, fyn) participate in signal transduction pathways leading from cytokine and integrin receptors and hence may serve to integrate stimuli received from several independent receptor structures. Thus, inhibitors of specific SH2 domains have the potential to block many neutrophil functions and serve as anti-inflammatory mediators.

Efforts to develop drugs targeted to SH2 domains currently are being conducted at the biochemical in vitro and cellular levels. Should such efforts be successful, it is theorized that the resulting drugs would be useful in the practice of the present invention.

d. Calcium Channel Antagonists

Calcium channel antagonists, previously described with relation to spasm inhibitory function, also can be used as anti-restenotic agents in the cardiovascular and general vascular solutions of the present invention. Activation of growth factor receptors, such as PDGF, is known to result in an increase in intracellular calcium (see FIG. 2). Studies at the cellular level have shown that actions of calcium channel antagonists are effective at inhibiting mitogenesis of vascular smooth muscle cells.

6. Synergistic Interactions Derived From Therapeutic Combinations Of Anti-Restenosis Agents And Other Agents Used In Cardiovascular and General Vascular Solutions Given the complexity of the disease process associated with restenosis after PTCA or other cardiovascular or general vascular therapeutic procedures and the multiplicity of molecular targets involved, blockade or inhibition of a single molecular target is unlikely to provide adequate efficacy in preventing vasospasm and restenosis (see FIG. 2). Indeed, a number of animal studies targeting different individual molecular receptors and/or enzymes have not proven effective in animal models or have not yielded efficacy for both pathologies in clinical trials to date. (Freed, M., et al., *An Intensive Poly-pharmaceutical Approach to the Prevention of Restenosis: the Mevacor, Ace Inhibitor, Colchicine (BIG-*

MAC) *Pilot Trial*, J. Am. Coll. of Cardiol. 21, p. 33A, (1993). Serruys, P., et al., *PARK: the Post Angioplasty Restenosis Ketanserin Trial*, J. Am. Coll. of Cardiol. 21, p. 322A, (1993). Therefore, a therapeutic combination of drugs acting on distinct molecular targets and delivered locally appears necessary for clinical effectiveness in the therapeutic approach to vasospasm and restenosis. As described below, the rationale for this synergistic molecular targeted therapy is derived from recent advances in understanding fundamental biochemical mechanisms by which vascular smooth muscle cells in the vessel wall transmit and integrate stimuli to which they are exposed during PTCA or other vascular interventional procedures.

a. "Crosstalk" and Convergence in Major Signaling Pathways

The molecular switches responsible for cell signaling have been traditionally divided into two major discrete signaling pathways, each comprising a distinct set of protein families that act as transducers for a particular set of extracellular stimuli and mediating distinct cell responses. One such pathway transduces signals from neurotransmitters and hormones through G-protein coupled receptors (GPCRs) to produce contractile responses using intracellular targets of trimeric G proteins and $Ca^{2+}$ (see FIG. 2). These stimuli and their respective receptors mediate smooth muscle contraction and may induce vasospasm in the context of PTCA or other cardiovascular or general vascular therapeutic or diagnostic procedure. Examples of signaling molecules involved in mediating spasm through the GPCR pathway are 5-HT and endothelin for which antagonists have been included acting via their respective G-protein coupled receptors.

A second major pathway transduces signals from growth factors, such as PDGF, through tyrosine kinases, adaptor proteins and the Ras protein into regulation of cell proliferation and differentiation (see FIGS. 2 and 5). This pathway may also be activated during PTCA or other cardiovascular or general vascular procedure leading to a high incidence of vascular smooth muscle cell proliferation. An example of a restenosis drug target is the PDGF-receptor.

Signals transmitted from neurotransmitters and hormones stimulate either of two classes of receptors: G-protein-coupled receptors, composed of seven-helix transmembrane regions, or ligand-gated ion channels. "Downstream" signals from both kinds of receptors converge on controlling the concentration of cytoplasmic $Ca^{2+}$ which triggers contraction in smooth muscle cells (see FIG. 2). Each GPCR transmembrane receptor activates a specific class of trimeric G proteins, including $G_q$, $G_i$ or many others. $GC_\alpha$ and/or $G_{\beta\gamma}$ subunits activate phospholipase $C_\beta$ resulting in activation of protein kinase C (PKC) and an increase in the levels of cytoplasmic calcium by release of calcium from intracellular stores.

Growth factor signaling, such as mediated by PDGF, converges on regulation of cell growth. This pathway depends upon phosphorylation of tyrosine residues in receptor tyrosine kinases and "downstream" enzymes (phospholipase $C_\gamma$ discussed above with regard to tyrosine kinases). Activation of the PDGF-receptor also leads to stimulation of PKC and elevation of intracellular calcium, common steps shared by the GPCRs (see FIG. 2). It is now recognized that ligand-independent "crosstalk" can transactivate tyrosine kinase receptor pathways in response to stimulation of GPCRs. Recent work has identified Shc, an adaptor protein in the tyrosine kinase/Ras pathway, as a key intermediary protein that relays messages from the GPCR pathway described above to the tyrosine kinase pathway (see FIG. 2) (Lev et al., 1995, Nature 376:737). Activation of Shc is calcium dependent. Thus, a combination of selective inhibitors which blocks transactivation of a common signaling pathway leading to vascular smooth muscle cell proliferation will act synergistically to prevent spasm and restenosis after PTCA or other cardiovascular or general vascular procedure. Specific examples are briefly detailed below.

b. Synergistic Interactions between PKC Inhibitors and Calcium Channel Antagonists In this case synergistic interactions among PKC inhibitors and calcium channel antagonists in achieving vasorelaxation and inhibition of proliferation occur due to "crosstalk" between GPCR and tyrosine kinase signaling pathways (see FIG. 2). A rationale for dual use is based upon the fact that these drugs have different molecular mechanisms of action. As described above, GPCR stimulation results in activation of protein kinase C and an increase in the levels of cytoplasmic calcium by release of calcium from intracellular stores. Calcium-activated PKC is a central control point in the transmission of extracellular responses. "Crosstalk" from GPCR stimulated pathways through PKC can lead to mitogenesis of vascular smooth muscle cells and thus calcium channel antagonists will have the dual action of directly blocking spasm and further preventing activation of proliferation by inhibiting Shc activation. Conversely, the PKC inhibitor acts on part of the pathway leading to contraction.

c. Synergistic Effects of PKC Inhibitors, 5-HT$_2$ Antagonists and ET$_A$ Antagonists The 5-HT$_2$ receptor family contains three members designated 5-HT$_{2A}$, 5-HT$_{2B}$, and 5-HT$_{2C}$, all of which share the common property of being coupled to phosphotidylinositol turnover and increases in intracellular calcium (Hoyer et al., 1988, Hartig et al., 1989). The distribution of these receptors includes vascular smooth muscle and platelets and, due to their localization, these 5-HT receptors are important in mediating spasm, thrombosis and restenosis. It has been found that the sustained phase of intracellular calcium elevation in smooth muscle cells induced by ET$_A$ receptor activation requires extracellular calcium and is at least partially blocked by nicardipine. Since activation of both 5-HT$_2$ receptors and ET$_A$ receptors is mediated through calcium, the inclusion of a PKC inhibitor is expected to synergistically enhance the actions of antagonists to both of these receptors when combined in a surgical solution (see FIGS. 2 and 4).

d. Synergistic Effects of Protein Tyrosine Kinase Inhibitors and Calcium Channel Antagonists The mitogenic effect of PDGF (or basic fibroblast growth factor or insulin-like-growth-factor-1) is mediated through receptors that possess intrinsic protein tyrosine kinase activity. The substrates for PDGF phosphorylation are many and lead to activation of mitogen-activated protein kinases (MAPK) and ultimately proliferation (see FIG. 5). The endothelin, 5-HT and thrombin receptors, which are members of the G-protein coupled superfamily, trigger a signal transduction pathway which includes increases in intracellular calcium, leading to activation of calcium channels on the plasma membrane. Thus, calcium channel antagonists interfere with a common mechanism employed by these GPCRs. It has recently been shown that activation of certain GPCRs, including endothelin and bradykinin, leads to a rapid increase in tyrosine phosphorylation of a number of intracellular proteins. Some of the proteins phosphorylated parallel those known necessary for mitogenic stimulation. The rapidity of the process was such that changes were detectable in seconds and the targets acted upon likely play a role in mitogenesis. These tyrosine phosphorylation events were not blocked by a selective PKC inhibitor or apparently mediated by increased intracellular calcium. Thus, since two independent pathways, the GPCR and tyrosine phosphorylation pathways, can drive the vascular smooth muscle cells into a proliferative state, it is necessary to block both independent signaling arms. This is the basis for the synergistic interaction between calcium channel antagonists and tyrosine kinase inhibitors in the surgical solution. Because the actions of the protein tyrosine kinase inhibitors in preventing vascular smooth muscle cell proliferation occur via independent molecular pathways (described above) from those involving calcium and protein kinase C, the combination of the two classes of drugs, calcium channel antagonists and protein tyrosine kinase inhibitors, is expected to be more efficacious in inhibiting spasm and restenosis than employing either single class of drug alone.

e. Synergistic Effects of Protein Tyrosine Kinase Inhibitors and Thrombin Receptor Antagonists Thrombin mediates its action via the thrombin receptor, another member of the GPCR superfamily. Binding to the receptor stimulates platelet aggregation, smooth muscle cell contraction and mitogenesis. Signal transduction occurs through multiple pathways: activation of phospholipse (PLC) through G proteins and activation of tyrosine kinases. The activation of tyrosine kinase activity is also essential for mitogenesis of the vascular smooth muscle cells. Experiments have shown that inhibition with a specific tyrosine kinase inhibitor was effective in blocking thrombin-induced mitosis, although there were no effects on the PLC pathway as monitored by measurement of intracellular calcium (Weiss and Nucitelli, 1992, J. Biol. Chem. 267:5608–5613). Because the actions of the protein tyrosine kinase inhibitors in preventing vascular smooth muscle cell proliferation occur via independent molecular pathways (described above) from those involving calcium and protein kinase C, the combination of protein tyrosine kinase inhibitors and thrombin receptor antagonists is anticipated to be more efficacious in inhibiting platelet aggregation, spasm and restenosis than employing either class of agent alone.

VI. Method of Application

The solution of the present invention has applications for a variety of operative/interventional procedures, including surgical, diagnostic and therapeutic techniques. The irrigation solution is perioperatively applied during arthroscopic surgery of anatomic joints, urological procedures, cardiovascular and general vascular diagnostic and therapeutic procedures and for general surgery. As used herein, the term "perioperative" encompasses application intraprocedurally, pre- and intraprocedurally, intra- and postprocedurally, and pre-, intra- and postprocedurally. Preferably, the solution is applied preprocedurally and/or postprocedurally as well as intraprocedurally. Such procedures conventionally utilize physiologic irrigation fluids, such as normal saline or lactated Ringer's, applied to the surgical site by techniques well known to those of ordinary skill in the art. The method of the present invention involves substituting the anti-pain/anti-inflammatory/anti-spasm/anti-restenosis irrigation solutions of the present invention for conventionally applied irrigation fluids. The irrigation solution is applied to the wound or surgical site prior to the initiation of the procedure, preferably before tissue trauma, and continuously throughout the duration of the procedure, to preemptively block pain and inflammation, spasm and restenosis. As used herein throughout, the term "irrigation" is intended to mean the flushing of a wound or anatomic structure with a stream of liquid. The term "application" is intended to encompass irrigation and other methods of locally introducing the solution of the present invention, such as introducing a gellable version of the solution to the operative site, with the gelled solution then remaining at the site throughout the procedure. As used herein throughout, the term "continuously" is intended to also include situations in which there is repeated and frequent irrigation of wounds at a frequency sufficient to maintain a predetermined therapeutic local concentration of the applied agents, and applications in which there may be intermittent cessation of irrigation fluid flow necessitated by operating technique.

The concentrations listed for each of the agents within the solutions of the present invention are the concentrations of the agents delivered locally, in the absence of metabolic transformation, to the operative site in order to achieve a predetermined level of effect at the operative site. It is understood that the drug concentrations in a given solution may need to be adjusted to account for local dilution upon delivery. For example, in the cardiovascular application, if one assumes an average human coronary artery blood flow rate of 80 cc per minute and an average delivery rate for the solution of 5 cc per minute via a local delivery catheter (i.e., a blood flow-to-solution delivery ratio of 16 to 1), one would require that the drug concentrations within the solution be increased 16-fold over the desired in vivo drug concentrations. Solution concentrations are not adjusted to account for metabolic transformations or dilution by total body distribution because these circumstances are avoided by local delivery, as opposed to oral, intravenous, subcutaneous or intramuscular application.

Arthroscopic techniques for which the present solution may be employed include, by way of non-limiting example, partial meniscectomies and ligament reconstructions in the knee, shoulder acromioplasties, rotator cuff debridements, elbow synovectomies, and wrist and ankle arthroscopies. The irrigation solution is continuously supplied intraoperatively to the joint at a flow rate sufficient to distend the joint capsule, to remove operative debris, and to enable unobstructed intra-articular visualization.

A suitable irrigation solution for control of pain and edema during such arthroscopic techniques is provided in Example I herein below. For arthroscopy, it is preferred that the solution include a combination, and preferably all, or any of the following: a serotonin$_2$ receptor antagonist, a serotonin$_3$ receptor antagonist, a histamine$_1$ receptor antagonist, a serotonin receptor agonist acting on the 1A, 1B, 1D, 1F and/or 1E receptors, a bradykinin$_1$ receptor antagonist, a bradykinin$_2$ receptor antagonist, and a cyclooxygenase inhibitor.

This solution utilizes extremely low doses of these pain and inflammation inhibitors, due to the local application of the agents directly to the operative site during the procedure. For example, less than 0.05 mg of amitriptyline (a suitable serotonin$_2$ and histamine$_1$ "dual" receptor antagonist) are needed per liter of irrigation fluid to provide the desired effective local tissue concentrations that would inhibit 5-HT$_2$ and H$_1$ receptors. This dosage is extremely low relative to the 10–25 mg of oral amitriptyline that is the usual starting dose for this drug. This same rationale applies to the anti-spasm and anti-restenosis agents which are utilized in the solution of the present invention to reduce spasm associated with urologic, cardiovascular and general vascular procedures and to inhibit restenosis associated with cardiovascular and general vascular procedures. For example, less than 0.2 mg of nisoldipine (a suitable calcium channel antagonist) is required per liter of irrigation fluid to provide the desired effective local tissue concentrations that would inhibit the voltage-dependent gating of the L-subtype of calcium channels. This dose is extremely low compared to the single oral dose of nisoldipine which is 20 to 40 mg.

In each of the surgical solutions of the present invention, the agents are included in low concentrations and are delivered locally in low doses relative to concentrations and doses required with conventional methods of drug administration to achieve the desired therapeutic effect. It is impossible to obtain an equivalent therapeutic effect by delivering similarly dosed agents via other (i.e., intravenous, subcutaneous, intramuscular or oral) routes of drug administration since drugs given systemically are subject to first- and second-pass metabolism.

For example, using a rat model of arthroscopy, the inventors examined the ability of amitriptyline, a 5-HT$_2$ antagonist, to inhibit 5-HT-induced plasma extravasation in the rat knee in accordance with the present invention. This study, described more fully below in Example XII, compared the therapeutic dosing of amitriptyline delivered locally (i.e., intra-articularly) at the knee and intravenously. The results demonstrated that intra-articular administration of amitriptyline required total dosing levels approximately 200-fold less than were required via the intravenous route to obtain the same therapeutic effect. Given that only a small fraction of the drug delivered intra-articularly is absorbed by the local synovial tissue, the difference in plasma drug levels between the two routes of administration is much greater than the difference in total amitriptyline dosing levels.

Practice of the present invention should be distinguished from conventional intra-articular injections of opiates and/or local anesthetics at the completion of arthroscopic or "open" joint (e.g., knee, shoulder, etc.) procedures. The solution of the present invention is used for continuous infusion throughout the surgical procedure to provide preemptive inhibition of pain and inflammation. In contrast, the high concentrations necessary to achieve therapeutic efficacy with a constant infusion of local anesthetics, such as lidocaine (0.5–2% solutions), would result in profound systemic toxicity.

Upon completion of the procedure of the present invention, it may be desirable to inject or otherwise apply a higher concentration of the same pain and inflammation inhibitors as used in the irrigation solution at the operative site, as an alternative or supplement to opiates.

The solution of the present invention also has application in cardiovascular and general vascular diagnostic and therapeutic procedures to potentially decrease vessel wall spasm, platelet aggregation, vascular smooth muscle cell proliferation and nociceptor activation produced by vessel manipulation. Reference herein to arterial treatment is intended to encompass the treatment of venous grafts harvested and placed in the arterial system. A suitable solution for such techniques is disclosed in Example II herein below. The cardiovascular and general vascular solution preferably includes any combination, and preferably all, of the following: a 5-HT$_2$ receptor antagonist (Saxena, P. R., et al., *Cardiovascular Effects of Serotonin Inhibitory Agonists and Antagonists*, J Cardiovasc Pharmacol 15 (Suppl. 7), pp. SI 7-S34 (1990); Douglas, 1985); a 5-HT$_3$ receptor antagonist to block activation of these receptors on sympathetic neurons and C-fiber nociceptive neurons in the vessel walls, which has been shown to produce brady- and tachycardia (Saxena et al. 1990); a bradykinin$_1$ receptor antagonist; and a cyclooxygenase inhibitor to prevent production of prostaglandins at tissue injury sites and thereby decrease pain and inflammation. In addition, the cardiovascular and general vascular solution also preferably will contain a serotonin$_{1B}$ (also known as serotonin$_{1D\beta}$) antagonist because serotonin has been shown to produce significant vascular spasm via activation of the serotonin$_{1B}$ receptors in humans. Kaumann, A. J., et al., *Variable Participation of 5-HT1-Like Receptors and 5-HT2 Receptors in Serotonin-Induced Contraction of Human Isolated Coronary Arteries*, Circulation 90, pp. 1141–53 (1994). This excitatory action of serotonin$_{1B}$ receptors in vessel walls, resulting in vasoconstriction, is in contrast to the previously-discussed inhibitory action of serotonin$_{1B}$ receptors in neurons. The cardiovascular and general vascular solution of the present invention also may suitably include one or more of the anti-restenosis agents disclosed herein that reduce the incidence and severity of post-procedural restenosis resulting from, for example, angioplasty or rotational atherectomy.

The solution of the present invention also has utility for reducing pain and inflammation associated with urologic procedures, such as trans-urethral prostate resection and similar urologic procedures. References herein to application of solution to the urinary tract or to the urological structures is intended to include application to the urinary tract per se, bladder and prostate and associated structures. Studies have demonstrated that serotonin, histamine and bradykinin produce inflammation in lower urinary tract tissues. Schwartz, M. M., et al., *Vascular Leakage in the Kidney and Lower Urinary Tract: Effects of Histamine, Serotonin and Bradykinin*, Proc Soc Exp Biol Med 140, pp. 535–539 (1972). A suitable irrigation solution for urologic procedures is disclosed in Example III herein below. The solution preferably includes a combination, and preferably all, of the following: a histamine$_1$ receptor antagonist to inhibit histamine-induced pain and inflammation; a 5-HT$_3$ receptor antagonist to block activation of these receptors on peripheral C-fiber nociceptive neurons; a bradykinin$_1$ antagonist; a bradykinin$_2$ antagonist; and a cyclooxygenase inhibitor to decrease pain/inflammation produced by prostaglandins at the tissue injury sites. Preferably an anti-spasm agent is also included to prevent spasm in the urethral canal and bladder wall.

Some of the solutions of the present invention may suitably also include a gelling agent to produce a dilute gel. This gellable solution may be applied, for example, within the urinary tract or an arterial vessel to deliver a continuous, dilute local predetermined concentration of agents.

The solution of the present invention may also be employed perioperatively for the inhibition of pain and inflammation in surgical wounds, as well as to reduce pain and inflammation associated with burns. Burns result in the release of a significant quantity of biogenic amines, which not only produce pain and inflammation, but also result in profound plasma extravasation (fluid loss), often a life-threatening component of severe burns. Holliman, C. J., et al., *The Effect of Ketanserin, a Specific Serotonin Antagonist, on Burn Shock Hemodynamic Parameters in a Porcine Burn Model*, J Trauma 23, pp. 867–871 (1983). The solution disclosed in Example I for arthroscopy may also be suitably applied to a wound or burn for pain and inflammation control, and for surgical procedures such as arthroscopy. The agents of the solution of Example I may alternately be included in a paste or salve base, for application to the burn or wound.

VII. EXAMPLES

The following are several formulations in accordance with the present invention suitable for certain operative procedures followed by a summary of three clinical studies utilizing the agents of the present invention.

A. Example I

Irrigation Solution for Arthroscopy

The following composition is suitable for use in anatomic joint irrigation during arthroscopic procedures. Each drug is solubilized in a carrier fluid containing physiologic electrolytes, such as normal saline or lactated Ringer's solution, as are the remaining solutions described in subsequent examples.

TABLE 25

| Class of Agent | Drug | Concentration (Nanomolar): | | |
|---|---|---|---|---|
| | | Therapeutic | Preferred | Most Preferred |
| serotonin$_2$ antagonist | amitriptyline | 0.1–1,000 | 50–500 | 100 |
| serotonin$_3$ antagonist | metoclopramide | 10–10,000 | 200–2,000 | 1,000 |
| histamine$_1$ antagonist | amitriptyline | 0.1–1,000 | 50–500 | 200 |
| serotonin$_{1A, 1B, 1D, 1F}$ agonist | sumatriptan | 1–1,000 | 10–200 | 50 |
| bradykinin$_1$ antagonist | [des-Arg$^{10}$] derivative of HOE 140 | 1–1,000 | 50–500 | 200 |
| bradykinin$_2$ antagonist | HOE 140 | 1–1,000 | 50–500 | 200 |

B. Example II

Irrigation Solution for Cardiovascular and General Vascular Therapeutic and Diagnostic Procedures The following drugs and concentration ranges in solution in a physiologic carrier fluid are suitable for use in irrigating operative sites during cardiovascular and general vascular procedures.

TABLE 26

| Class of Agent | Drug | Concentration (Nanomolar): | | |
|---|---|---|---|---|
| | | Therapeutic | Preferred | Most Preferred |
| serotonin$_2$ antagonist | trazodone | 0.1–2,000 | 50–500 | 200 |
| serotonin$_3$ antagonist | metoclopramide | 10–10,000 | 200–2,000 | 1,000 |
| serotonin$_{1B}$ antagonist | yohimbine | 0.1–1,000 | 50–500 | 200 |
| bradykinin$_1$ antagonist | [des-Arg$^{10}$] derivative of HOE 140 | 1–1,000 | 50–500 | 200 |
| cyclooxygenase inhibitor | ketorolac | 100–10,000 | 500–5,000 | 3,000 |

C. Example III

Irrigation Solution for Urologic Procedures

The following drugs and concentration ranges in solution in a physiologic carrier fluid are suitable for use in irrigating operative sites during urologic procedures.

TABLE 27

| Class of Agent | Drug | Concentration (Nanomolar): | | |
|---|---|---|---|---|
| | | Therapeutic | Preferred | Most Preferred |
| histamine$_1$ antagonist | terfenadine | 0.1–1,000 | 50–500 | 200 |
| serotonin$_3$ antagonist | metoclopramide | 10–10,000 | 200–2,000 | 1,000 |
| bradykinin$_1$ antagonist | [des-Arg$^{10}$] derivative of HOE 140 | 1–1,000 | 50–500 | 200 |
| bradykinin$_2$ antagonist | HOE 140 | 1–1,000 | 50–500 | 200 |
| cyclooxygenase inhibitor | | 100–10,000 | 500–5,000 | 3,000 |

D. Example IV

Irrigation Solution for Arthroscopy, Burns, General Surgical Wounds and Oral/Dental Applications The following composition is preferred for use in anatomic irrigation during arthroscopic and oral/dental procedures and the management of burns and general surgical wounds. While the solution set forth in Example I is suitable for use with the present invention, the following solution is even more preferred because of expected higher efficacy.

TABLE 28

| Class of Agent | Drug | Therapeutic | Preferred | Most Preferred |
|---|---|---|---|---|
| serotonin$_2$ antagonist | amitriptyline | 0.1–1,000 | 50–500 | 200 |
| serotonin$_3$ antagonist | metoclopramide | 10–10,000 | 200–2,000 | 1,000 |
| histamine$_1$ antagonist | amitriptyline | 0.1–1,000 | 50–500 | 200 |
| serotonin$_{1A, 1B, 1D, 1F}$ agonist | sumatriptan | 1–1,000 | 10–200 | 100 |
| cyclooxygenase inhibitor | ketorolac | 100–10,000 | 500–5,000 | 3,000 |
| neurokinin$_1$ antagonist | GR 82334 | 1–1,000 | 10–500 | 200 |
| neurokinin$_2$ antagonist | (±) SR 48968 | 1–1,000 | 10–500 | 200 |
| purine$_{2X}$ antagonist | PPADS | 100–100,000 | 10,000–100,000 | 50,000 |
| ATP-sensitive K$^+$ channel agonist | (–) pinacidil | 1–10,000 | 100–1,000 | 500 |
| Ca$^{2+}$ channel antagonist | nifedipine | 1–10,000 | 100–5,000 | 1,000 |
| kallikrein inhibitor | aprotinin | 0.1–1,000 | 50–500 | 200 |

E. Example V

Alternate Irrigation Solution for Cardiovascular and General Vascular Therapeutic and Diagnostic Procedures The following drugs and concentration ranges in solution in a physiologic carrier fluid are preferred for use in irrigating operative sites during cardiovascular and general vascular procedures. Again, this solution is preferred relative to the solution set forth in Example II above for higher efficacy.

TABLE 29

| Class of Agent | Drug | Therapeutic | Preferred | Most Preferred |
|---|---|---|---|---|
| serotonin$_2$ antagonist | trazodone | 0.1–2,000 | 50–500 | 200 |
| cyclooxygenase inhibitor | ketorolac | 100–10,000 | 500–5,000 | 3,000 |
| endothelin antagonist | BQ 123 | 0.01–1,000 | 10–1,000 | 500 |
| ATP-sensitive K$^+$ channel agonist | (–) pinacidil | 1–10,000 | 100–1,000 | 500 |
| Ca$^{2+}$ channel antagonist | nisoldipine | 1–10,000 | 100–1,000 | 500 |
| nitric oxide donor | SIN-1 | 10–10,000 | 100–1,000 | 500 |

F. Example VI

Alternate Irrigation Solution for Urologic Procedures

The following drugs and concentration ranges in solution in a physiologic carrier fluid are preferred for use in irrigating operative sites during urologic procedures. The solution is believed to have even higher efficacy than the solution set forth in prior Example III.

TABLE 30

| Class of Agent | Drug | Therapeutic | Preferred | Most Preferred |
|---|---|---|---|---|
| serotonin$_2$ antagonist | LY 53857 | 0.1–500 | 1–100 | 50 |
| histamine$_1$ antagonist | terfenadine | 0.1–1,000 | 50–500 | 200 |

TABLE 30-continued

| Class of Agent | Drug | Concentration (Nanomolar): | | |
|---|---|---|---|---|
| | | Therapeutic | Preferred | Most Preferred |
| cyclooxygenase inhibitor | ketorolac | 100–10,000 | 500–5,000 | 3,000 |
| neurokinin$_2$ antagonist | SR 48968 | 1–1,000 | 10–500 | 200 |
| purine$_{2X}$ antagonist | PPADS | 100–100,000 | 10,000–100,000 | 50,000 |
| ATP-sensitive K$^+$ channel agonist | (−) pinacidil | 1–10,000 | 100–1,000 | 500 |
| Ca$^{2+}$ channel antagonist | nifedipine | 1–10,000 | 100–5,000 | 1,000 |
| kallikrein inhibitor | aprotinin | 0.1–1,000 | 50–500 | 200 |
| nitric oxide donor | SIN-1 | 10–10,000 | 100–1,000 | 500 |

G. Example VII

Cardiovascular and General Vascular Anti-Restenosis Irrigation Solution

The following drugs and concentration ranges in solution in a physiologic carrier fluid are preferred for use in irrigation during cardiovascular and general vascular therapeutic and diagnostic procedures. The drugs in this preferred solution may also be added at the same concentration to the cardiovascular and general vascular irrigation solutions of Examples II and V described above or Example VIII described below for preferred anti-spasmodic, anti-restenosis, anti-pain/anti-inflammation solutions.

TABLE 31

| Class of Agent | Drug | Concentration (Nanomolar): | | |
|---|---|---|---|---|
| | | Therapeutic | Preferred | Most Preferred |
| thrombin inhibitor | hirulog | 0.2–20,000 | 2–2,000 | 200 |
| glycoprotein IIb/IIIa receptor blocker | integrelin | 0.1–10,000 × Kd | 1–1000 × Kd | 100 × Kd |
| PKC inhibitor | GF 109203X* | 0.1–10,000 | 1–1,000 | 200 |
| protein tyrosine kinase inhibitor | tyrphostin AG1296 | 10–100,000 | 100–20,000 | 10,000 |

*Also known as Go 6850 or Bisindoylmaleimide I (available from Warner-Lambert)

TABLE 32

| Class of Agent | Drug | Concentration (Nanomolar): | | |
|---|---|---|---|---|
| | | Therapeutic | Preferred | Most Preferred |
| NO donor | FK 409 (NOR-3) | 1–1,000 | 10–500 | 250 |
| NO donor | FR 144420 (NOR-4) | 10–10,000 | 100–5,000 | 1,000 |

H. Example VIII

Alternate Irrigation Solution for Cardiovascular and General Vascular Therapeutic and Diagnostic Procedures An additional preferred solution for use in cardiovascular and general vascular therapeutic and diagnostic procedures is formulated the same as the previously described formulation of Example V, except that the nitric oxide (NO donor) SIN-1 is replaced by a combination of two agents, FK 409 (NOR-3) and FR 144420 (NOR-4), at the concentrations set forth below:

I. Example IX

Alternate Irrigation Solution for Arthroscopy, General Surgical Wounds, Burns and Oral/Dental Applications An alternate preferred solution for use in irrigation of arthroscopic, general surgical and oral/dental applications is formulated the same as in the previously described Example IV, with the following substitution, deletion and additions at the concentrations set forth below:
1) amitryptyline is replaced by mepyramine as the H$_1$ antagonist;
2) the kallikrein inhibitor, aprotinin, is deleted;
3) a bradykinin$_1$ antagonist, [leu$^9$][des-Arg$^{10}$] kalliden, is added;
4) a bradykinin$_2$ antagonist, HOE 140, is added; and
5) a µ-opoid antagonist, fentanyl, is added.

TABLE 33

| Class of Agent | Drug | Concentration (Nanomolar): | | |
|---|---|---|---|---|
| | | Therapeutic | Preferred | Most Preferred |
| $H_1$ antagonist | mepyramine | 0.1–1,000 | 5–200 | 100 |
| bradykinin$_1$ antagonist | [leu$^9$][des-Arg$^{10}$] kalliden | 0.1–500 | 10–200 | 100 |
| bradykinin$_2$ antagonist | HOE 140 | 1–1,000 | 50–500 | 200 |
| $\mu$-opioid agonist | fentanyl | 0.1–500 | 10–200 | 100 |

J. Example X

Alternate Irrigation Solution for Urologic Procedures

An alternate preferred solution for use in irrigation during urologic procedures is formulated the same as in the previously described Example VI with the following substitution, deletion and additions at the concentrations set forth below:

1) SIN-1 is replaced by a combination of two agents;
   a) FK 409 (NOR-3); and
   b) FR 144420 (NOR-4);
2) the kallikrein inhibitor, aprotinin, is deleted;
3) a bradykinin$_1$ antagonist, [leu$^9$][des-Arg$^{10}$] kalliden, is added; and
4) a bradykinin$_2$ antagonist, HOE 140, is added.

TABLE 34

| Class of Agent | Drug | Concentration (Nanomolar): | | |
|---|---|---|---|---|
| | | Therapeutic | Preferred | Most Preferred |
| NO donor | FK 409 (NOR-3) | 1–1,000 | 10–500 | 250 |
| NO donor | FR 144420 (NOR-4) | 10–10,000 | 100–5,000 | 1,000 |
| bradykinin$_1$ antagonist | [leu$^9$][des-Arg$^{10}$] kalliden | 0.1–500 | 10–200 | 100 |
| bradykinin$_2$ antagonist | HOE 140 | 1–1,000 | 50–500 | 200 |

K. Example XI

Balloon Dilatation of Normal Iliac Arteries in the New Zealand White Rabbit and the Influence of Histamine/Serotonin Receptor Blockade on the Response The purpose of this study was twofold. First, a new in vivo model for the study of arterial tone was employed. The time course of arterial dimension changes before and after balloon angioplasty is described below. Second, the role of histamine and serotonin together in the control of arterial tone in this setting was then studied by the selective infusion of histamine and serotonin receptor blocking agents into arteries before and after the angioplasty injury.

1. Design Considerations

This study was intended to describe the time course of change in arterial lumen dimensions in one group of arteries and to evaluate the effect of histamine/serotonin receptor blockade on these changes in a second group of similar arteries. To facilitate the comparison of the two different groups, both groups were treated in an identical manner with the exception of the contents of an infusion performed during the experiment. In control animals (arteries), the infusion was normal saline (the vehicle for test solution). The histamine/serotonin receptor blockade treated arteries received saline containing the receptor antagonists at the same rate and at the same part of the protocol as control animals. Specifically, the test solution included: (a) the serotonin$_3$ antagonist metoclopramide at a concentration of 16.0 $\mu$M; (b) the serotonin$_2$ antagonist trazodone at a concentration of 1.6 $\mu$M; and (c) the histamine antagonist promethazine at concentrations of 1.0 $\mu$M, all in normal saline. Drug concentrations within the test solution were 16-fold greater than the drug concentrations delivered at the operative site due to a 16 to 1 flow rate ratio between the iliac artery (80 cc per minute) and the solution delivery catheter (5 cc per minute). This study was performed in a prospective, randomized and blinded manner. Assignment to the specific groups was random and investigators were blinded to infusion solution contents (saline alone or saline containing the histamine/serotonin receptor antagonists) until the completion of the angiographic analysis.

2. Animal Protocol

This protocol was approved by the Seattle Veteran Affairs Medical Center Committee on Animal Use and the facility is fully accredited by the American Association for Accreditation of Laboratory Animal Care. The iliac arteries of 3–4 kg male New Zealand white rabbits fed a regular rabbit chow were studied. The animals were sedated using intravenous xylazine (5 mg/kg) and ketamine (35 mg/kg) dosed to effect and a cutdown was performed in the ventral midline of the neck to isolate a carotid artery. The artery was ligated distally, an arteriotomy performed and a 5 French sheath was introduced into the descending aorta. Baseline blood pressure and heart rate were recorded and then an angiogram of the distal aorta and bilateral iliac arteries was recorded on 35 mm cine film (frame rate 15 per second) using hand injection of iopamidol 76% (Squibb Diagnostics, Princeton, N.J.) into the descending aorta. For each angiogram, a calibration object was placed in the radiographic field of view to allow for correction for magnification when diameter measurements were made. A 2.5 French infusion catheter (Advanced Cardiovascular Systems, Santa Clara, Calif.) was placed through the carotid sheath and positioned 1–2 cm above the aortic bifurcation. Infusion of the test solution—either saline alone or saline containing the histamine/serotonin receptor antagonists—was started at a rate of 5 cc per minute and continued for 15 minutes. At 5 minutes into the infusion, a second angiogram was performed using the previously described technique, then a 2.5 mm balloon angioplasty catheter (the Lightning, Cordis Corp., Miami, Fla.) was rapidly advanced under fluoroscopic guidance into the left and then the right iliac arteries. In each iliac the balloon catheter was carefully positioned between the proximal and distal deep femoral branches using bony landmarks and the balloon was inflated for 30 seconds to 12 ATM of pressure. The balloon catheter was inflated using a dilute solution of the radiographic contrast agent so that the inflated balloon diameter could be recorded on cine film. The angioplasty catheter was rapidly removed and another angiogram was recorded on cine film at a mean of 8 minutes after the infusion was begun. The infusion was continued until the 15 minute time point and another angiogram (the fourth) was performed. Then the infusion was stopped (a total of 75 cc of solution had been infused) and the infusion catheter was removed. At the 30 minute time point (15 minutes after the infusion was stopped), a final angiogram was recorded as before. Blood pressure and heart rate were recorded at the 15 and 30 minute time points immediately before the angiograms. After the final angiogram, the animal was euthanized with an overdose of the anesthetic agents administered intravenously and the iliac arteries were retrieved and immersion fixed in formation for histologic analysis.

3. Angiographic Analysis

The angiograms were recorded on 35 mm cine film at a frame rate of 15 per second. For analysis, the angiograms were projected from a Vanguard projector at a distance of 5.5 feet. Iliac artery diameters at prespecified locations relative to the balloon angioplasty site were recorded based on hand held caliper measurement after correction for magnification by measurement of the calibration object. Measurements were made at baseline (before test solution infusion was begun), 5 minutes into the infusion, immediately post balloon angioplasty (a mean of 8 minutes after the test solution was begun), at 15 minutes (just before the infusion was stopped) and at 30 minutes (15 minutes after the infusion was stopped). Diameter measurements were made at three sites in each iliac artery: proximal to the site of balloon dilatation, at the site of balloon dilatation and just distal to the site of balloon dilatation.

The diameter measurements were then converted to area measurements by the formula:

$$\text{Area} = (Pi)(\text{Diameter}^2)/4.$$

For calculation of vasoconstriction, baseline values were used to represent the maximum area of the artery and percent vasoconstriction was calculated as: % Vasoconstriction={(Baseline area−Later time point area)/Baseline area}×100.

4. Statistical Methods

All values are expressed as mean ±1 standard error of the mean. The time course of vasomotor response in control arteries was assessed using one way analysis of variance with correction for repeated measures. Post hoc comparison of data between specific time points was performed using the Scheffe test. Once the time points at which significant vasoconstriction occurred had been determined in control arteries, the control and histamine/serotonin receptor antagonist treated arteries were compared at those time points where significant vasoconstriction occurred in control arteries using multiple analysis of variance with treatment group identified as an independent variable. To compensate for the absence of a single a priori stated hypothesis, a p value <0.01 was considered significant. Statistics were performed using Statistica for Windows, version 4.5, (Statsoft, Tulsa, Okla.).

5. Results

The time course of arterial dimension changes before and after balloon angioplasty in normal arteries receiving saline infusion was evaluated in 16 arteries from 8 animals (Table 35). Three segments of each artery were studied: the proximal segment immediately upstream from the balloon dilated segment, the balloon dilated segment and the distal segment immediately downstream from the balloon dilated segment. The proximal and distal segments demonstrated similar patterns of change in arterial dimensions: in each, there was significant change in arterial diameter when all time points were compared (proximal segment, p=0.0002 and distal segment, p<0.001, ANOVA). Post hoc testing indicated that the diameters at the immediate post angioplasty time point were significantly less than the diameters at baseline or at the 30 minute time point in each of these segments. On the other hand, the arterial diameters in each segment at the 5 minute, 15 minute and 30 minute time points were similar to the baseline diameters. The balloon dilated segment showed lesser changes in arterial dimension than the proximal and distal segments. The baseline diameter of this segment was 1.82±0.05 mm; the nominal inflated diameter of the balloon used for angioplasty was 2.5 mm and the actual measured inflated diameter of the balloon was 2.20±0.03 mm (p<0.0001 vs. baseline diameter of the balloon treated segment). Thus, the inflated balloon caused circumferential stretch of the balloon dilated segment, but there was only slight increase in lumen diameter from baseline to the 30 minute time point (1.82±0.05 mm to 1.94±0.07 mm, p=NS by post hoc testing).

TABLE 35

Angiographically determined lumen diameters at the specified times before and after balloon dilatation of normal iliac arteries.

| Segment | Baseline | 5 Minute | Immediate Post PTA | 15 Minute | 30 Minute |
|---|---|---|---|---|---|
| Proximal[1] | 2.18 ± 0.7 | 2.03 ± 0.7 | 1.81 ± 0.08* | 2.00 ± .08 | 2.23 ± .08 |
| Balloon[2] | 1.82 ± .05 | 1.77 ± .03 | 1.79 ± .05 | 1.70 ± .04 | 1.94 ± .07 |
| Distal[3] | 1.76 ± .04 | 1.68 ± .04** | 1.43 ± .04* | 1.54 ± .03 | 1.69 ± .06 |

All measurements in mm. Means ± SEM. PTA = percutaneous transluminal angioplasty.
[1]p = 0.0002 (ANOVA within group comparison),
[2]p = 0.03 (ANOVA within group comparison),
[3]p < 0.0001 (ANOVA within group comparison). N = 16 at all time points.
*p < 0.01 versus baseline and 30 minute diameter measurements (Scheffe test for post hoc comparisons).
**p < 0.01 versus immediate post PTA measurements (Scheffe test for post hoc comparisons). All other post hoc comparisons were not significant using the p < 0.01 threshold.

Arterial lumen diameters were used to calculate lumen area then the area measurements were used to calculate percent vasoconstriction by comparison of the 5 minute, immediate post angioplasty, 15 and 30 minute data to the baseline measurements. The proximal and distal segment data expressed as percent vasoconstriction are shown in FIG. 9; the changes in the amount of vasoconstriction over time are significant (in the proximal segment, p=0.0008; in the distal segment, p=0.0001, ANOVA). Post hoc testing identifies the vasoconstriction at the immediate post angioplasty time point as significantly different from that present at the 30 minute time point (P<0.001 in both segments). In the distal segment, the immediate post angioplasty vasoconstriction was also significantly less than that at 5 minutes (p<0.01); no other differences in intra-time point comparisons were significant by post hoc testing.

The luminal changes in control arteries can be summarized as follows: 1) Vasoconstriction with loss of approximately 30% of baseline luminal area occurs in the segments of artery proximal and distal to the balloon dilated segment immediately after balloon dilatation. There are trends to smaller amounts of vasoconstriction in the proximal and distal segments before dilatation and at the 15 minute time point (approximately 7 minutes after dilatation) also, but by the 30 minute time point (approximately 22 minutes after dilatation), a trend towards vasodilatation has replaced the previous vasoconstriction; 2) In the balloon dilated segment, only minor changes in lumen dimensions are present, and, despite the use of a balloon with a significantly larger inflated diameter than was present in this segment at baseline, there was no significant increase in lumen diameter of the dilated segment. These findings lead to a conclusion that any effects of the putative histamine/serotonin treatment would only be detectable in the proximal and distal segments at the time points where vasoconstriction was present.

The histamine/serotonin receptor blockade solution was infused into 16 arteries (8 animals); angiographic data was available at all time points in 12 arteries. Heart rate and systolic blood pressure measurements were available in a subset of animals (Table 36). There were no differences in heart rate or systolic blood pressure when the two animal groups were compared within specific time points. Histamine/serotonin treated animals showed trends toward a decrease in the systolic blood pressure from baseline to 30 minutes (−14±5 mm Hg, p=0.04) and a lower heart rate (−26±10, p=0.05). Within the control animals, there was no change in heart rate or systolic blood pressure over the duration of the experiment.

TABLE 36

Systolic blood pressure and heart rate measurements in control and histamine/serotonin treated animals.

| Group | Baseline (N) | 5 Minute (N) | 15 Minute (N) | 30 Minute (N) |
| --- | --- | --- | --- | --- |
| Systolic Blood Pressure | | | | |
| Control | 83 ± 4 (8) | 84 ± 4 (8) | 82 ± 6 (8) | 80 ± 4 (8) |
| Histamine/Serotonin | 93 ± 5 (6) | 87 ± 9 (4) | 82 ± 9 (6) | 80 ± 8 (6)* |
| Heart Rate | | | | |
| Control | 221 ± 18 (5) | 234 ± 18 (4) | 217 ± 23 (5) | 227 ± 22 (5) |
| Histamine/Serotonin | 232 ± 8 (5) | 232 ± 8 (5) | 209 ± 14 (5) | 206 ± 12 (5)** |

Systolic blood pressure in mm Hg and heart rate in beats per minute. Mean ± SEM.
*p = 0.04 for decrease in systolic blood pressure from baseline to 30 minutes and
**p = 0.05 for decrease in heart rate from baseline to 30 minutes within the histamine/serotonin treated animals.

The proximal and distal segments of histamine/serotonin treated arteries were compared to control arteries using the percent vasoconstriction measurement. FIG. 10A shows the effects of the histamine/serotonin infusion on proximal segment vasoconstriction relative to the vasoconstriction present in the control arteries. When the findings in the two treatment groups were compared at the baseline, immediate post angioplasty and 15 minute time points, histamine/serotonin infusion resulted in significantly less vasoconstriction compared to the control saline infusion (p=0.003. 2-way ANOVA). Comparison of the two treatment groups in the distal segment is illustrated in FIG. 10B. Despite observed differences in mean diameter measurements in the distal segment, solution treated vessels exhibited less vasoconstriction than saline treated control vessels at baseline, immediate post-angioplasty and 15 minute time points, this pattern did not achieve statistical significance (p=0.32, 2-way ANOVA). Lack of statistical significance may be attributed to smaller than expected vasoconstriction values in the control vessels.

L. Example XII

Amitriptyline Inhibition of 5-Hydroxytryptamine-Induced Knee Joint Plasma Extravasation—Comparison of Intra-Articular Versus Intravenous Routes of Administration The following study was undertaken in order to compare two routes of administration of the 5-HT$_2$ receptor antagonist, amitriptyline: 1) continuous intra-articular infusion; versus 2) intravenous injection, in a rat knee synovial model of inflammation. The ability of amitriptyline to inhibit 5-HT-induced joint plasma extravasation by comparing both the efficacy and total drug dose of amitriptyline delivered via each route was determined.

1. Animals

Approval from the Institutional Animal Care Committee at the University of California, San Francisco was obtained for these studies. Male Sprague-Dawley rats (Bantin and Kingman, Fremont, Calif.) weighing 300–450 g were used in these studies. Rats were housed under controlled lighting conditions (lights on 6 A.M. to 6 P.M.), with food and water available ad libitum.

2. Plasma Extravasation

Rats were anesthetized with sodium pentobarbital (65 mg/kg) and then given a tail vein injection of Evans Blue dye (50 mg/kg in a volume of 2.5 ml/kg), which is used as a marker for plasma protein extravasation. The knee joint capsule was exposed by excising the overlying skin, and a 30-gauge needle was inserted into the joint and used for the infusion of fluid. The infusion rate (250 μl/min) was controlled by a Sage Instruments Syringe pump (Model 341B, Orion Research Inc., Boston, Mass.). A 25-gauge needle was also inserted into the joint space and perfusate fluid was extracted at 250 μl/min, controlled by a Sage Instruments Syringe pump (Model 351).

The rats were randomly assigned to three groups: 1) those receiving only intra-articular (IA) 5-HT (1 μM), 2) those receiving amitriptyline intravenously (IV) (doses ranging from 0.01 to 1.0 mg/kg) followed by IA 5-HT (1 mM), and 3) those receiving amitriptyline intra-articularly (IA) (concentrations ranging from 1 to 100 nM) followed by IA 5-HT (1 μM) plus IA amitriptyline. In all groups, baseline plasma extravasation levels were obtained at the beginning of each experiment by perfusing 0.9% saline intra-articularly and collecting three perfusate samples over a 15 min period (one every 5 min). The first group was then administered 5-HT IA for a total of 25 min. Perfusate samples were collected every 5 min for a total of 25 min. Samples were then analyzed for Evans Blue dye concentration by spectrophotometric measurement of absorbance at 620 nm, which is linearly related to its concentration (Carr and Wilhelm, 1964). The IV amitriptyline group was administered the drug during the tail vein injection of the Evans Blue dye. The knee joints were then perfused for 15 min with saline (baseline), followed by 25 min perfusion with 5-HT (1 μM). Perfusate samples were collected every 5 min for a total of 25 min. Samples were then analyzed using spectrophotometry. In the IA amitriptyline group, amitriptyline was perfused intra-articularly for 10 min after the 15 min saline perfusion, then amitriptyline was perfused in combination with 5-HT for an additional 25 min. Perfusate samples were collected every 5 min and analyzed as above.

Some rat knees were excluded from the study due to physical damage of knee joint or inflow and outflow mismatch (detectable by presence of blood in perfusate and high baseline plasma extravasation levels or knee joint swelling due to improper needle placement).

a. 5-HT-Induced Plasma Extravasation

Baseline plasma extravasation was measured in all knee joints tested (total n=22). Baseline plasma extravasation levels were low, averaging 0.022±0.003 absorbance units at 620 nm (average±standard error of the mean). This baseline extravasation level is shown in FIGS. 11 and 12 as a dashed line.

5-HT (1 μM) perfused into the rat knee joint produces a time-dependent increase in plasma extravasation above baseline levels. During the 25 min perfusion of 5-HT intra-articularly, maximum levels of plasma extravasation were achieved by 15 min and continued until the perfusion was terminated at 25 min (data not shown). Therefore, 5-HT-induced plasma extravasation levels reported are the average of the 15, 20 and 25 min time points during each experiment. 5-HT-induced plasma extravasation averaged 0.192±0.011, approximately an 8-fold stimulation above baseline. This data is graphed in FIGS. 11 and 12, corresponding to the "0" dose of IV amitriptyline and the "0" concentration of IA amitriptyline, respectively.

b. Effect of Intravenous Amitriptyline on 5-HT-Induced Plasma Extravasation

Amitriptyline administered via tail vein injection produced a dose-dependent decrease in 5-HT-induced plasma extravasation as shown in FIG. 11. The $IC_{50}$ for IV amitriptyline inhibition of 5-HT-induced plasma extravasation is approximately 0.025 mg/kg. 5-HT-induced plasma extravasation is completely inhibited by an IV amitriptyline dose of 1 mg/kg, the plasma extravasation averaging 0.034±0.010.

c. Effect of Intra-articular Amitriptyline on 5-HT-Induced Plasma Extravasation Amitriptyline administered alone in increasing concentrations intra-articularly did not affect plasma extravasation levels relative to baseline, with the plasma extravasation averaging 0.018±0.002 (data not shown). Amitriptyline co-perfused in increasing concentrations with 5-HT produced a concentration-dependent decrease in 5-HT-induced plasma extravasation as shown in FIG. 12. 5-HT-induced plasma extravasation in the presence of 3 nM IA amitriptyline was not significantly different from that produced by 5-HT alone; however, 30 nM amitriptyline co-perfused with 5-HT produced a greater than 50% inhibition, while 100 nM amitriptyline produced complete inhibition of 5-HT-induced plasma extravasation. The $IC_{50}$ for IA amitriptyline inhibition of 5-HT-induced plasma extravasation is approximately 20 nM.

The major finding of the present study is that 5-HT (1 μM) perfused intra-articularly in the rat knee joint produces a stimulation of plasma extravasation that is approximately 8-fold above baseline levels and that either intravenous or intra-articular administration of the 5-$HT_2$ receptor antagonist, amitriptyline, can inhibit 5-HT-induced plasma extravation. The total dosage of administered amitriptyline, however, differs dramatically between the two methods of drug delivery. The $IC_{50}$ for IV amitriptyline inhibition of 5-HT-induced plasma extravasation is 0.025 mg/kg, or 7.5× $10^{-3}$ mg in a 300 g adult rat. The $IC_{50}$ for IA amitriptyline inhibition of 5-HT-induced plasma extravasation is approximately 20 nM. Since 1 ml of this solution was delivered every five minutes for a total of 35 min during the experiment, the total dosage perfused into the knee was 7 ml, for a total dosage of $4.4\times10^{-5}$ mg perfused into the knee. This IA amitriptyline dose is approximately 200-fold less than the IV amitriptyline dose. Furthermore, it is likely that only a small fraction of the IA perfused drug is systemically absorbed, resulting in an even greater difference in the total delivered dose of drug.

Since 5-HT may play an important role in surgical pain and inflammation, as discussed earlier, 5-HT antagonists such as amitriptyline may be beneficial if used during the perioperative period. A recent study attempted to determine the effects of oral amitriptyline on post-operative orthopedic pain (Kerrick et al., 1993). An oral dose as low as 50 mg produced undesirable central nervous system side-effects, such as a "decreased feeling of well-being". Their study, in addition, also showed that oral amitriptyline produced higher pain scale scores than placebo (P<0.05) in the post-operative patients. Whether this was due to the overall unpleasantness produced by oral amitriptyline is not known. In contrast, an intra-articular route of administration allows an extremely low concentration of drug to be delivered locally to the site of inflammation, possibly resulting in maximal benefit with minimal side-effects.

M. Example XIII

Effects Of Cardiovascular and General Vascular Solution On Rotational Atherectomy-Induced Vasospasm In Rabbit Arteries

1. Solution Tested

This study utilized an irrigation solution consisting of the agents set forth in Example V. above, with the following exceptions. Nitroprusside replaced SIN-1 as the nitric oxide donor and nicardipine replaced nisoldipine as the $Ca^{2+}$ channel antagonist.

The concentration of nitroprusside was selected based on its previously-defined pharmacological activity ($EC_{50}$). The concentrations of the other agents in this test solution were determined based on the binding constants of the agents with their cognate receptors. Furthermore, all concentrations were adjusted based on a blood flow rate of 80 cc per minute in the distal aorta of the rabbit and a flow rate of 5 cc per minute in the solution delivery catheter. Three components were mixed in one cc or less DMSO, and then these components and the remaining three components were mixed to their final concentrations in normal saline. A control solution consisting of normal saline was utilized. The test solution or the control solution was infused at a rate of 5 cc per minute for 20 minutes. A brief pause in the infusion was necessary at the times blood pressure measurements were made, so each animal received about 95 cc of the solution in the 20 minute treatment period.

2. Animal Protocol

This protocol was approved by the Seattle Veteran Affairs Medical Center Committee on Animal Use, which is accredited by the American Association for Accreditation of Laboratory Animal Care. The iliac arteries of 3–4 kg male New Zealand white rabbits fed a 2% cholesterol rabbit chow for 3–4 weeks were studied. The animals were sedated using intravenous xylazine (5 mg/kg) and ketamine (35 mg/kg) dosed to effect and a cutdown was performed in the ventral midline of the neck to isolate a carotid artery. The artery was ligated distally, an arteriotomy performed and a 5 French sheath was introduced into the descending aorta and positioned at the level of the renal arteries. Baseline blood pressure and heart rate were recorded. An angiogram of the distal aorta and bilateral iliac arteries was recorded on 35 mm cine film (frame rate 15 per second) using hand injection of iopamidol 76% (Squibb Diagnostics, Princeton, N.J.) into the descending aorta.

For each angiogram, a calibration object was placed in the radiographic field of view to allow for correction for magnification when diameter measurements were made. Infusion of either the above described test solution or a saline control solution was started through the side arm of the 5 French sheath (and delivered to the distal aorta) at a rate of 5 cc per minute and continued for 20 minutes. At 5 minutes into the infusion, a second angiogram was performed using the previously described technique. Then a 1.25 mm or a 1.50 mm rotational atherectomy burr (Heart Technology/Boston Scientific Inc.) was advanced to the iliac arteries. The rotational atherectomy burr was advanced three times over a guide wire in each of the iliac arteries at a rotation rate of 150,000 to 200,000 RPM. In each iliac, the rotational atherectomy burr was advanced from the distal aorta to the mid portion of the iliac artery between the first and second deep femoral branches. The rotational atherectomy burr was rapidly removed and another angiogram was recorded on cine film at a mean of 8 minutes after the infusion was begun.

The infusion was continued until the 20 minute time point, and another angiogram (the fourth) was performed. Then the infusion was stopped. A total of about 95 cc of the control or test solution had been infused. At the 30 minute time point (15 minutes after the infusion was stopped), a final angiogram was recorded as before. Blood pressure and heart rate were recorded at the 15 and 30 minute time points immediately before the angiograms. After the final angiogram, the animal was euthanized with an overdose of the anesthetic agents administered intravenously.

3. Angiographic Analysis

The angiograms were recorded on 35 mm cine film at a frame rate of 15 per second. Angiograms were reviewed in random order without knowledge of treatment assignment. For analysis, the angiograms were projected from a Vanguard projector at a distance of 5.5 feet. The entire angiogram for each animal was reviewed to identify the anatomy of the iliac arteries and to identify the sites of greatest spasm in the iliac arteries. A map of the iliac anatomy was prepared to assist in consistently identifying sites for measurement. Measurements were made on the 15 minute post rotational atherectomy angiogram first, then in random order on the remaining angiograms from that animal. Measurements were made using an electronic hand-held caliper (Brown & Sharpe, Inc., N. Kingston, R.I.). Iliac artery diameters were measured at three locations: proximal to the first deep femoral branch of the iliac artery; at the site of most severe spasm (this occurred between the first and second deep femoral artery branches in all cases); and at a distal site (near or distal to the origin of the second deep femoral artery branch of the iliac artery). Measurements were made at baseline (before test solution infusion was begun), 5 minutes into the infusion, immediately post rotational atherectomy (a mean of 8 minutes after the test solution was begun), at 20 minutes just after the infusion was stopped (this was 15 minutes after the rotational atherectomy was begun) and at 15 minutes after the infusion was stopped (30 minutes after the rotational atherectomy was begun). The calibration object was measured in each angiogram.

The diameter measurements were then converted to area measurements by the formula:

$$\text{Area} = (Pi)(\text{Diameter}^2)/4.$$

For calculation of vasoconstriction, baseline values were used to represent the maximum area of the artery and percent vasoconstriction was calculated as:

% Vasoconstriction={(Baseline area−Later time point area)/Baseline area}×100.

4. Statistical Methods

All values are expressed as mean ±1 standard error of the mean. The time course of vasomotor response in control arteries was assessed using one way analysis of variance with correction for repeated measures. Post hoc comparison of data between specific time points was performed using the Scheffe test. Test solution treated arteries were compared to saline treated arteries at specified locations in the iliac arteries and at specified time points using multiple analysis of variance (MANOVA). To compensate for the absence of a single a priori hypothesis, a p value <0.01 was considered significant. Statistics were performed using Statistica for Windows, version 4.5, (Statsoft, Tulsa, Okla.).

5. Results

Eight arteries in 4 animals received saline solution and 13 arteries in seven animals received test solution. In each artery, regardless of the solution used, rotational atherectomy was performed with the rotating burr passing from the distal aorta to the mid-portion of the iliac artery. Thus, the proximal iliac artery segment and the segment designated as the site of maximal vasoconstriction were subjected to the rotating burr. The guide wire for the rotational atherectomy catheter passed through the distal segment, but the rotating burr of the rotational atherectomy catheter itself did not enter the distal segment.

Iliac artery diameters in saline treated arteries at the three specified segments are summarized in Table 37. In the proximal segment, there was no significant change in the diameter of the artery over the time course of the experiment (p=0.88, ANOVA). In the mid-iliac artery at the site of maximal vasoconstriction, there was a significant reduction in diameter with the largest reduction occurring at the 15 minute post-rotational atherectomy time point (p<0.0001, ANOVA comparing measurements at all 5 time points). The distal segment diameter did not significantly change over the time course of the experiment (p=0. 19, ANOVA comparing all time points) although there was a trend towards a smaller diameter at the immediate post- and 15 minute post-rotational atherectomy time points.

TABLE 37

Iliac artery lumen diameters at specified time points in saline treated arteries.

| Segment | Baseline N = 8 | 5 Minutes into Infusion N = 8 | Immediate Post RA N = 8 | 15 Minute after RA N = 8 | 30 Minutes after RA N = 8 |
|---|---|---|---|---|---|
| Proximal[1] | 2.40 ± .18 | 2.32 ± .14 | 2.32 ± 0.13 | 2.38 ± .13 | 2.34 ± .07* |
| Mid[2] | 2.01 ± .08 | 1.84 ± .09 | 1.57 ± .15 | 1.24 ± .13 | 1.87 ± .06** |
| Distal[3] | 2.01 ± .10 | 1.86 ± .08 | 1.79 ± .08 | 1.81 ± .09 | 1.96 ± .06*** |

RA = rotational atherectomy
[1]Proximal iliac artery measurement site, proximal to the first deep femoral branch
[2]Mid iliac artery at the site of maximal vasospasm
[3]Distal iliac artery measurement site, near or distal to the second deep femoral branch
*p = 0.88 by ANOVA comparing diameters in the proximal segment at the five time points.
**p = 0.000007 by ANOVA comparing diameters at site of maximal vasospasm at the five time points.
***p = 0.19 by ANOVA comparing diameters in the distal segment at the five time points.

The diameters of iliac arteries treated with the test solution are shown in Table 38. Angiograms were not recorded in three of these arteries at the 5 minute post-initiation of the infusion time point and angiographic data were excluded from two arteries (one animal) at the 30 minute post-rotational atherectomy time point because the animal received an air embolus at the 15 minute angiogram that resulted in hemodynamic instability. Because there are a variable number of observations at the five time points, no ANOVA statistic was applied to this data. Still, it is apparent that the magnitude of change in the diameter measurements within segments in the test solution treated arteries over the time course of the experiment is less than was seen in the saline treated arteries.

TABLE 38

Iliac artery lumen diameters at specified time points in Test Solution treated arteries.

| Segment | Baseline N = 13 | 5 Minutes into Infusion N = 10 | Immediate Post RA N = 13 | 15 Minute after RA N = 13 | 30 Minutes after RA N = 11 |
|---|---|---|---|---|---|
| Proximal[1] | 2.28 ± .06 | 2.07 ± .07 | 2.22 ± .05 | 2.42 ± .06 | 2.39 ± .08 |
| Mid[2] | 1.97 ± .06 | 1.79 ± .06 | 1.74 ± .04 | 1.95 ± .07 | 1.93 ± .08 |
| Distal[3] | 2.00 ± .06 | 1.92 ± .04 | 1.90 ± .04 | 2.00 ± .06 | 2.01 ± .07 |

RA = rotational atherectomy
[1]Proximal iliac artery measurement site, proximal to the first deep femoral branch
[2]Mid iliac artery at the site of maximal vasospasm
[3]Distal iliac artery measurement site, near or distal to the second deep femoral branch Because of the different number of observations at the various time points, ANOVA was not performed to determine the statistical similarity/difference in diameters within specific segments.

The primary endpoint for this study was the comparison of the amounts of vasoconstriction in saline treated and test solution treated arteries. Vasoconstriction was based on arterial lumen areas derived from artery diameter measurements. Area values at the 5 minute, immediate post-rotational atherectomy and later time points were compared to the baseline area values to calculate the relative change in area. The results were termed "vasoconstriction" if the lumen area was smaller at the later time point than at baseline, and "vasodilatation" if the lumen area was larger at the later time point compared to the baseline area (Tables 39 and 40). To facilitate statistical analysis with the largest number of observations possible in both treatment groups, the test solution and saline treated artery data were compared at the immediate post- and at the 15 minute postrotational atherectomy time points.

In the proximal segment (FIG. 13), there was essentially no change in lumen area with either treatment at the immediate post-rotational atherectomy time point, but there was some vasodilatation in this segment by the 15 minute post-rotational rotational atherectomy time point. Test solution did not alter the results of rotational atherectomy compared to saline treatment in this segment. In the mid-vessel (FIG. 14) at the site of maximal vasoconstriction, however, test solution significantly blunted the vasoconstriction caused by rotational atherectomy in the saline treated arteries (p=0.0004, MANOVA corrected for repeated measures). In the distal segment (FIG. 15), there was little vasoconstriction in the saline treated arteries and test solution did not significantly alter the response to rotational atherectomy.

TABLE 39

Amount of vasoconstriction (negative values) or vasodilatation (positive values) at specified time points in saline treated arteries.

| Segment | 5 Minutes into Infusion N = 8 | Immediate Post RA N = 8 | 15 Minute after RA N = 8 | 30 Minutes after RA N = 8 |
|---|---|---|---|---|
| Proximal[1] | −3% ± .8% | −1% ± 10% | 3% ± 8% | 3% ± 13% |
| Mid[2] | −14% ± 7% | −35% ± 10% | −58% ± 7% | −11% ± .9% |
| Distal[3] | −9% ± .10% | −14% ± .14% | −14% ± 10% | 2% ± .12% |

[1]Proximal iliac artery measurement site, proximal to the first deep femoral branch
[2]Mid iliac artery at the site of maximal vasospasm
[3]Distal iliac artery measurement site, near or distal to the second deep femoral branch

TABLE 40

Amount of vasoconstriction (negative values) or vasodilatation (positive values) at specified time points in Test Solution treated arteries.

| Segment | 5 Minutes into Infusion N = 10 | Immediate Post RA N = 13 | 15 Minute after RA N = 13 | 30 Minutes after RA N = 11 |
|---|---|---|---|---|
| Proximal[1] | −17% ± .5% | −4% ± 3% | 14% ± 6% | 7% ± 9% |
| Mid[2] | −14% ± 5% | −20% ± 5% | 0.3% ± 7% | −5% ± .5% |
| Distal[3] | −8% ± .4% | −9% ± .4% | 1% ± 4% | 3% ± .6% |

[1]Proximal iliac artery measurement site, proximal to the first deep femoral branch
[2]Mid iliac artery at the site of maximal vasospasm
[3]Distal iliac artery measurement site, near or distal to the second deep femoral branch The hemodynamic response in the saline and test solution treated arteries is summarized in Table 41. Compared to saline treated animals, test solution treated animals sustained substantial hypotension and significant tachycardia during the solution infusion. By 15 minutes after completion of the infusion (or at the 30 minute postrotational atherectomy time point), test solution treated animals showed some partial, but not complete, return of blood pressure towards baseline.

TABLE 41

Blood pressure and heart rates during the protocol.

| Group | Baseline (N) | 5 Minute (N) | 15 Minute (N) | 30 Minute (N) |
|---|---|---|---|---|
| Systolic Blood Pressure | | | | |
| Saline | 83 ± 9 (4) | 93 ± 6 (3) | 92 ± 11 (4) | 83 ± 10 (4)* |
| Test Solution | 92 ± 5 (7) | 35 ± 5 (7) | 35 ± 5 (7) | 46 ± 5 (7)** |
| Heart Rate | | | | |
| Saline | 202 ± 16 (3) | 204 ± 3 (3) | 198 ± 22 (3) | 193 ± 29 (3)* |
| Test Solution | 187 ± 111 (7) | 246 ± 11 (7) | 240 ± 5 (7) | 247 ± 16 (7)** |

*There was no significant change in systolic blood pressure or heart rate in this group (p = 0.37 for systolic blood pressure and p = 0.94 for heart rate, ANOVA).
**There was a highly significant change in systolic blood pressure and heart rate in this group (p < 0.0001 for systolic blood pressure and p = 0.002 for heart rate, ANOVA).

6. Summary of Study

1. Rotational atherectomy in hypercholesterolemic New Zealand white rabbits results in prominent vasospasm in the mid-portion of iliac arteries subjected to the rotating burr. The vasospasm is most apparent 15 minutes after rotational atherectomy treatment and has almost completely resolved without pharmacologic intervention by 30 minutes after rotational atherectomy.

2. Under the conditions of rotational atherectomy treatment studied in this protocol, test solution treatment in accordance with the present invention almost completely abolishes the vasospasm seen after the mid-iliac artery is subjected to the rotating burr.

3. Treatment with test solution of the present invention, given the concentration of components used in this protocol, results in profound hypotension during the infusion of the solution. The attenuation of vasospasm after rotational atherectomy by test solution occurred in the presence of severe hypotension.

While the preferred embodiment of the invention has been illustrated and described, it will be appreciated that various changes to the disclosed solutions and methods can be made therein without departing from the spirit and scope of the invention. For example, alternate pain inhibitors and anti-inflammation and anti-spasm and anti-restenosis agents may be discovered that may augment or replace the disclosed agents in accordance with the disclosure contained herein. It is therefore intended that the scope of letters patent granted hereon be limited only by the definitions of the appended claims.

The embodiments of the invention in which an exclusive property or privilege is claimed are defined as follows:

1. A method of inhibiting pain and inflammation during an arthroscopic procedure at an operative site within a joint, comprising:
    delivering to a joint during an arthroscopic procedure a solution including a plurality of pain/inflammation inhibitory agents in a liquid carrier, the plurality of agents being selected to act on a plurality of differing molecular targets, wherein the solution is applied locally and perioperatively to the arthroscopic operative site and the agents are collectively effective for inhibiting pain and inflammation at the arthroscopic operative site during the procedure.

2. The method of claim 1, comprising continuously applying the solution to the arthroscopic operative site.

3. The method of claim 2, comprising continuously irrigating the arthroscopic operative site with the solution.

4. The method of claim 1, wherein the solution is applied by irrigation of the arthroscopic operative site.

5. The method of claim 1, wherein the perioperative application of the solution comprises intraprocedural application together with preprocedural or postprocedural application of the solution.

6. The method of claim 5, wherein the perioperative application of the solution comprises preprocedural, intraprocedural and postprocedural application of the solution.

7. The method of claim 6, wherein the solution is continuously applied to the arthroscopic operative site.

8. The method of claim 1, wherein each of the plurality of agents in the solution is delivered locally at a concentration of no greater than 100,000 nanomolar.

9. The method of claim 8, wherein each of the plurality of agents in the solution is delivered locally at a concentration of no greater than 10,000 nanomolar.

10. The method of claim 1, wherein each agent is included at a concentration or dosage that is sufficient to provide a level of inhibitory effect at the arthroscopic operative site when delivered locally to the arthroscopic operative site and that results in a plasma concentration that is less than a plasma concentration that would be required to achieve the same level of inhibitory effect at the arthroscopic operative site when delivered systemically.

11. The method of claim 1, wherein each of the plurality of agents in the solution applied is included at a concentration that is sufficient to provide a predetermined level of pain/inflammation inhibitory effect at the arthroscopic operative site, when locally applied, in the absence of metabolic transformation occurring prior to delivery to the arthroscopic operative site, and that is less than a concentration which would be required to provide the same predetermined level of inhibitory effect at the arthroscopic operative site if applied in a manner which would entail metabolic transformation of the agents occurring prior to delivery to the arthroscopic operative site.

12. The method of claim 1, wherein the pain/inflammation inhibitory agents are selected from the group consisting of: serotonin receptor antagonists; serotonin receptor agonists; histamine receptor antagonists; bradykinin receptor antagonists; kallikrein inhibitors; tachykinin receptor antagonists including neurokinin$_1$ receptor subtype antagonists and neurokinin$_2$ receptor subtype antagonists; calcitonin gene-related peptide receptor antagonists; interleukin receptor antagonists; phospholipase inhibitors including PLA$_2$ isoform inhibitors and PLC$_\gamma$ isoform inhibitors; cyclooxygenase inhibitors; lipooxygenase inhibitors; prostanoid receptor antagonists including eicosanoid EP-1 receptor subtype antagonists and eicosanoid EP-4 receptor subtype antagonists and thromboxane receptor subtype antagonists; leukotriene receptor antagonists including leukotriene B$_4$ receptor subtype antagonists and leukotriene D$_4$ receptor subtype antagonists; opioid receptor agonists including $\mu$-opioid receptor subtype agonists, $\delta$-opioid receptor subtype agonists, and $\kappa$-opioid receptor subtype agonists; purinoceptor agonists and antagonists including P$_{2Y}$ receptor agonists and P$_{2X}$ receptor antagonists; and ATP-sensitive potassium channel openers.

13. The method of claim 12, wherein each of the plurality of agents in the solution is delivered locally at a concentration in nanomolar of from 0.1 to 10,000 times the dissociation constant of the agent.

14. The method of claim 13, wherein each of the plurality of agents in the solution is delivered locally at a concentration in nanomolar of from 1.0 to 1,000 times the dissociation constant of the agent.

15. The method of claim 14, wherein each of the plurality of agents in the solution is delivered locally at a concentration in nanomolar of 100 times the dissociation constant of the agent.

16. The method of claim 12, wherein the pain/inflammation inhibitory agents, if selected, are delivered locally at a concentration of: 0.1 to 10,000 nanomolar for serotonin receptor antagonists; 0.1 to 2,000 nanomolar for serotonin receptor agonists; 0.01 to 1,000 nanomolar for histamine receptor antagonists; 0.1 to 10,000 nanomolar for bradykinin receptor antagonists; 0.1 to 1,000 nanomolar for kallikrein inhibitors; 0.1 to 10,000 nanomolar for neurokinin$_1$ receptor subtype antagonists; 1.0 to 10,000 nanomolar for neurokinin$_2$ receptor subtype antagonists; 1 to 1,000 nanomolar for calcitonin gene-related peptide receptor antagonists; 1 to 1,000 nanomolar for interleukin receptor antagonists; 100 to 100,000 nanomolar for PLA$_2$ isoform inhibitors; 100 to 200,000 nanomolar for cyclooxygenase inhibitors; 100 to 10,000 nanomolar for lipooxygenase inhibitors; 100 to 10,000 nanomolar for eicosanoid EP-1 receptor subtype antagonists; 100 to 10,000 nanomolar for leukotriene B$_4$ receptor subtype antagonists; 0.1 to 500 nanomolar for $\mu$-opioid receptor subtype agonists; 0.1 to 500 nanomolar for $\delta$-opioid receptor subtype agonists; 0.1 to 500 nanomolar for $\kappa$-opioid receptor subtype agonists; 100 to 100,000 nanomolar for purinoceptor antagonists; and 0.1 to 10,000 nanomolar for ATP-sensitive potassium channel openers.

17. The method of claim 1, wherein the solution applied comprises: a serotonin$_2$ receptor subtype antagonist included at a concentration of 50 to 500 nanomolar; a serotonin$_3$ receptor subtype antagonist included at a concentration of 200 to 2,000 nanomolar; a histamine$_1$ receptor subtype antagonist included at a concentration of 5 to 200 nanomolar; a serotonin receptor agonist included at a concentration of 10 to 200 nanomolar; a cyclooxygenase inhibitor included at a concentration of 500 to 5,000 nanomolar; a neurokinin$_1$ receptor subtype antagonist included at a concentration of 10 to 500 nanomolar; a neurokinin$_2$ receptor subtype antagonist included at a concentration of 10 to 500 nanomolar; a purinoceptor antagonist included at a concentration of 10,000 to 100,000 nanomolar; an ATP-sensitive potassium channel opener included at a concentration of 100 to 1,000 nanomolar; a calcium channel antagonist included at a concentration of 100 to 5,000 nanomolar; a bradykinin$_1$ receptor subtype antagonist included at a concentration of 10 to 200 nanomolar; a bradykinin$_2$ receptor subtype antagonist included at a concentration of 50 to 500 nanomolar; and a $\mu$-opioid receptor subtype agonist included at concentration of 10 to 200 nanomolar.

18. The method of claim 1, wherein at least one of the agents in the solution comprises a cyclooxygenase inhibitor and at least one other of the agents comprises a serotonin receptor antagonist and/or a histamine receptor antagonist.

19. The method of claim 1, wherein the solution includes a cyclooxygenase inhibitor and amitriptyline.

20. A method of preemptively inhibiting pain and inflammation during an arthroscopic procedure at an operative site within a joint, comprising:

delivering to a joint during an arthroscopic procedure a solution including a plurality of pain/inflammation inhibitory agents in a liquid carrier, the plurality of agents being selected to act on a plurality of differing molecular targets, wherein the solution is applied locally and perioperatively to the arthroscopic operative site, prior to and during significant local operative trauma, and the agents are collectively effective for inhibiting pain and inflammation at the arthroscopic operative site during the procedure.

21. A method of inhibiting pain and inflammation during an arthroscopic procedure at an operative site within a joint, comprising:

delivering to a joint during an arthroscopic procedure a solution including a plurality of pain/inflammation inhibitory agents in a carrier, the plurality of agents being selected to act on a plurality of differing molecular targets, wherein the solution is applied locally and perioperatively to the arthroscopic operative site to provide a substantially constant concentration of each of the agents at the arthroscopic operative site, and the agents are collectively effective for inhibiting pain and inflammation at the arthroscopic operative site during the procedure.

22. The method of claim 21, wherein the concentration of the agents is maintained substantially constant throughout a majority of the arthroscopic procedure.

23. The method of claim 21, wherein the carrier comprises an irrigation carrier.

24. The method of claim 21, wherein the carrier remains at the site after introduction to the arthroscopic operative site.

25. The method of claim 24, wherein the carrier comprises a gel.

26. A solution for use in the inhibition of pain and inflammation during an arthroscopic procedure at an operative site within a joint, comprising a plurality of pain and inflammation inhibitory agents in a liquid carrier, the plurality of agents being selected to act on a plurality of differing molecular targets, the concentration of each agent within the solution being the concentration of that agent which is desired to be delivered locally to achieve a level of inhibitory effect at the arthroscopic operative site and that results in a plasma concentration that is less than a plasma concentration that would be required to achieve the same level of inhibitory effect at the arthroscopic operative site when delivered systemically, the agents collectively being effective for inhibiting pain and inflammation at the arthroscopic operative site during the procedure.

27. The solution of claim 26, wherein each of the plurality of agents in the solution is included at a concentration of no greater than 100,000 nanomolar, adjusted for dilution upon local delivery at the arthroscopic operative site, in the absence of metabolic transformation occurring prior to delivery to the arthroscopic operative site.

28. The solution of claim 26, wherein each of the plurality of agents in the solution is included at a concentration of no greater than 10,000 nanomolar, adjusted for dilution upon local delivery at the arthroscopic operative site, in the absence of metabolic transformation occurring prior to delivery to the arthroscopic operative site.

29. The solution of claim 26, wherein the pain/inflammation inhibitory agents are selected from the group consisting of: serotonin receptor antagonists; serotonin receptor agonists; histamine receptor antagonists; bradykinin receptor antagonists; kallikrein inhibitors; tachykinin receptor antagonists including neurokinin$_1$ receptor subtype antagonists and neurokinin$_2$ receptor subtype antagonists; calcitonin gene-related peptide receptor antagonists; interleukin receptor antagonists; phospholipase inhibitors including PLA$_2$ isoform inhibitors and PLC$_{65}$ isoform inhibitors; cyclooxygenase inhibitors; lipooxygenase inhibitors; prostanoid receptor antagonists including eicosanoid EP-1 receptor subtype antagonists and eicosanoid EP-4 receptor subtype antagonists and thromboxane receptor subtype antagonists; leukotriene receptor antagonists including leukotriene B$_4$ receptor subtype antagonists and leukotriene D$_4$ receptor subtype antagonists; opioid receptor agonists including $\mu$-opioid receptor subtype agonists, $\delta$-opioid receptor subtype agonists, and $\kappa$-opioid receptor subtype agonists; purinoceptor agonists and antagonists including P$_{2Y}$ receptor agonists and P$_{2X}$ receptor antagonists; and ATP-sensitive potassium channel openers.

30. The solution of claim 29, wherein each of the plurality of agents in the solution is included at a concentration in nanomolar of from 0.1 to 10,000 times the dissociation constant of the agent, adjusted for dilution upon local delivery at the arthroscopic operative site, in the absence of metabolic transformation occurring prior to delivery to the arthroscopic operative site.

31. The solution of claim 30, wherein each of the plurality of agents in the solution is included at a concentration in nanomolar of from 1.0 to 1,000 times the dissociation constant of the agent, adjusted for dilution upon local delivery at the arthroscopic operative site, in the absence of metabolic transformation occurring prior to delivery to the arthroscopic operative site.

32. The solution of claim 31, wherein each of the plurality of agents in the solution is included at a concentration in nanomolar of 100 times the dissociation constant of the agent, adjusted for dilution upon local delivery at the arthroscopic operative site, in the absence of metabolic transformation occurring prior to delivery to the arthroscopic operative site.

33. The solution of claim 29, wherein the selected pain/inflammation inhibitory agents are included at a concentration of: 0.1 to 10,000 nanomolar for serotonin receptor antagonists; 0.1 to 2,000 nanomolar for serotonin receptor agonists; 0.01 to 1,000 nanomolar for histamine receptor antagonists; 0.1 to 10,000 nanomolar for bradykinin receptor antagonists; 0.1 to 1,000 nanomolar for kallikrein inhibitors; 0.1 to 10,000 nanomolar for neurokinin$_1$ receptor subtype antagonists; 1.0 to 10,000 nanomolar for neurokinin$_2$ receptor subtype antagonists; 1 to 1,000 nanomolar for calcitonin gene-related peptide receptor antagonists; 1 to 1,000 nanomolar for interleukin receptor antagonists; 100 to 100,000 nanomolar for PLA$_2$ isoform inhibitors; 100 to 200,000 nanomolar for cyclooxygenase inhibitors; 100 to 10,000 nanomolar for lipooxygenase inhibitors; 100 to 10,000 nanomolar for eicosanoid EP-1 receptor subtype antagonists; 100 to 10,000 nanomolar for leukotriene B$_4$ receptor subtype antagonists; 0.1 to 500 nanomolar for $\mu$-opioid receptor subtype agonists; 0.1 to 500 nanomolar for $\delta$-opioid receptor subtype agonists; 0.1 to 500 nanomolar for $\kappa$-opioid receptor subtype agonists; 100 to 100,000 nanomolar for purinoceptor antagonists; and 0.1 to 10,000 nanomolar for ATP-sensitive potassium channel openers.

34. The solution of claim 26, wherein at least one of the agents in the solution comprises a cyclooxygenase inhibitor and at least one other of the agents comprises a serotonin receptor antagonist and/or a histamine receptor antagonist.

35. The solution of claim 34, wherein the solution includes a cyclooxygenase inhibitor and amitriptyline.

36. A solution for use in the inhibition of pain and inflammation during an arthroscopic procedure at an operative site within a joint, comprising a plurality of pain and inflammation inhibitory agents in a liquid carrier, the plurality of agents being selected to act on a plurality of differing molecular targets, each of the agents included at a concentration that is sufficient to provide a predetermined level of pain/inflammation inhibitory effect at the arthroscopic operative site, when locally applied, in the absence of metabolic transformation occurring prior to delivery to the arthroscopic operative site, and that is less than a concentration which would be required to provide the same predetermined level of inhibitory effect at the arthroscopic operative site if applied in a manner which would entail metabolic transformation of the agents occurring prior to delivery to the arthroscopic operative site, the agents collectively being effective for inhibiting pain and inflammation at the arthroscopic operative site during the procedure.

* * * * *

UNITED STATES PATENT AND TRADEMARK OFFICE
CERTIFICATE OF CORRECTION

PATENT NO. : 6,645,168 B2
DATED : November 11, 2003
INVENTOR(S) : G.A. Demopulos et al.

It is certified that error appears in the above-identified patent and that said Letters Patent is hereby corrected as shown below:

<u>Title page,</u>
Item [56], References Cited, U.S. PATENT DOCUMENTS, insert the following reference: -- 5,624,893  4/1997  Yanni --
OTHER PUBLICATIONS, "Reuben, S. S., et al.," reference, "sugery" should read -- surgery --; and "kerorolac," should read -- ketorolac, --
"Sosnowski, M., et al.,"reference, "Receptor-Seletive" should read -- Receptor-Selective --
"Kuga, T., et al.," reference, "Minature" should read -- Miniature --
"Reifart, et al.," reference, "Cetner," should read -- Center, --
"Talke, P., et al.," reference, "vascualr" should read -- vascular --
"Karczag, et al.," reference, "Combiniation" should read -- Combination --

<u>Column 5,</u>
Line 23, "disphosphate" should read -- diphosphate --

<u>Column 13,</u>
Line 63, "potently" should read -- potentially --

<u>Column 18,</u>
Line 15, "$C_\gamma(PLC_{65})$" should read -- $C_\gamma (PLC_\gamma)$ --

<u>Column 24,</u>
Lines 57-58, "(R)2-([R-2-([(s)-2-([1-hexahydro-1H-azepinyl]-carbonyl]amino-4-methyl-pentanoyl) amino-3-(3[1-methyl-1H-indodyl])propionylamino-3(2-pyridyl) propionic acid" should read -- (R)2-[R-2-[(s)-2-[[1-hexahydro-1H-azepinyl]-carbonyl] amino-4-methyl-pentanoyl] amino-3-[3-(1-methyl-1H-indodyl)propionyl]amino-3(2-pyridyl) propionic acid --

<u>Column 26,</u>
Line 23, "KATP" should read -- $K_{ATP}$ --

<u>Column 35,</u>
Line 50, "$C_\beta$resulting" should read -- $C_\beta$, resulting --

<u>Column 37,</u>
Line 25, "phospholipse" should read -- phospholipase --

<u>Column 46,</u>
Line 67, "$\mu$-opoid" should read -- $\mu$-opioid --

UNITED STATES PATENT AND TRADEMARK OFFICE
CERTIFICATE OF CORRECTION

PATENT NO. : 6,645,168 B2
DATED : November 11, 2003
INVENTOR(S) : G.A. Demopulos et al.

It is certified that error appears in the above-identified patent and that said Letters Patent is hereby corrected as shown below:

Column 47,
Line 49, "Dilatation" should read -- Dilation --

Column 49,
Line 26, "dilatation," should read -- dilation, --
Line 26, "dilatation" should read -- dilation --

Column 50,
Line 22, Table 35, heading line 2, "dilatation" should read -- dilation --
Line 61, "dilatation." should read -- dilation. --
Lines 63 and 64, "dilatation" should read -- dilation --
Line 66, "dilatation)," should read -- dilation), --
Line 66, "vasodilatation" should read -- vasodilation --

Column 51,
Line 50, "(p=0.003." should read -- (p=0.003, --

Column 58,
Line 29, ""vasodilatation"" should read -- "vasodilation" --
Line 39, "vasodilatation" should read -- vasodilation --
Line 41, delete "rotational", second occurrence
Line 53, Table 39 heading line 1, "vasodilatation" should read -- vasodilation Column 59,
Line 3, Table 40 heading line 2, "vasodilatation" should read -- vasodilation --

UNITED STATES PATENT AND TRADEMARK OFFICE
CERTIFICATE OF CORRECTION

PATENT NO.    : 6,645,168 B2
DATED         : November 11, 2003
INVENTOR(S)   : G.A. Demopulos et al.

It is certified that error appears in the above-identified patent and that said Letters Patent is hereby corrected as shown below:

<u>Column 63,</u>
Line 39, "$C_\gamma(PLC_{65})$" should read -- $C_\gamma (PLC_\gamma)$ --

Signed and Sealed this

Twenty-fourth Day of February, 2004

JON W. DUDAS
*Acting Director of the United States Patent and Trademark Office*